US009974573B2

(12) United States Patent
Schell et al.

(10) Patent No.: US 9,974,573 B2
(45) Date of Patent: May 22, 2018

(54) MINIMALLY INVASIVE APPROACHES, METHODS AND APPARATUSES TO ACCOMPLISH SACROILIAC FUSION

(71) Applicant: Quandary Medical, LLC, Denver, CO (US)

(72) Inventors: Gerald R Schell, Bay City, MI (US); Jeffrey R. Schell, Denver, CO (US); David C. Eyvazzadeh, Denver, CO (US); Yuta Okkotsu, Aurora, CO (US)

(73) Assignee: MIS IP HOLDINGS LLC, Denver, CO (US)

(*) Notice: Subject to any disclaimer, the term of this patent is extended or adjusted under 35 U.S.C. 154(b) by 0 days. days.

(21) Appl. No.: 14/923,309

(22) Filed: Oct. 26, 2015

(65) Prior Publication Data

US 2016/0120661 A1   May 5, 2016

Related U.S. Application Data

(60) Provisional application No. 62/068,602, filed on Oct. 24, 2014, provisional application No. 62/105,045, filed on Jan. 19, 2015.

(51) Int. Cl.
| | | |
|---|---|---|
| A61B 17/70 | (2006.01) |
| A61F 2/30 | (2006.01) |
| A61F 2/46 | (2006.01) |
| A61B 17/16 | (2006.01) |
| A61B 17/86 | (2006.01) |

(52) U.S. Cl.
CPC ...... *A61B 17/7055* (2013.01); *A61B 17/1671* (2013.01); *A61B 17/863* (2013.01);
(Continued)

(58) Field of Classification Search
CPC ............... A61F 2/4601; A61F 2/30988; A61F 2002/30996; A61F 2002/4635;
(Continued)

(56) References Cited

U.S. PATENT DOCUMENTS

| 6,921,403 B2 | 7/2005 | Cragg et al. |
| 8,734,462 B2 | 5/2014 | Reiley et al. |

(Continued)

FOREIGN PATENT DOCUMENTS

| WO | 2013/033205 | 3/2013 |
| WO | 2014/158419 | 10/2014 |

*Primary Examiner* — Pedro Philogene
(74) *Attorney, Agent, or Firm* — Rocky Mountain Patent LLC

(57) ABSTRACT

The present disclosure presents novel methods, procedures associated steps, and apparatuses to accomplish SI joint fusion in a minimally invasive manner. The preferred embodiment of the invention incorporates improved methods, procedures and apparatuses to facilitate a SI joint fusion providing a generally safer, more minimally invasive SI joint stabilization. In the method associated with the preferred embodiment of the invention, in one aspect, a path or a plurality of paths through an ilium to the sacrum is established, wherein a stabilizer device allows the securement of the sacrum to the ilium. In another aspect, a path or a plurality of paths to the SI joint is established, where bone fusion material allows fusion of the articular surface of the ilium and the articular surface of the sacrum of an SI joint.

14 Claims, 34 Drawing Sheets

(52) U.S. Cl.
CPC ...... *A61B 17/8605* (2013.01); *A61B 17/8685* (2013.01); *A61B 17/8695* (2013.01); *A61F 2002/30995* (2013.01)

(58) Field of Classification Search
CPC ............ A61B 17/7055; A61B 17/8695; A61B 17/1671; A61B 17/8685
USPC ......... 623/17.11–17.16; 606/246–279, 86 A, 606/86 R, 907, 908, 304
See application file for complete search history.

(56) References Cited

U.S. PATENT DOCUMENTS

| | | | |
|---|---|---|---|
| 9,649,138 B2* | 5/2017 | Altarac | A61B 17/7064 |
| 2009/0216238 A1* | 8/2009 | Stark | A61B 17/025 606/96 |
| 2009/0259261 A1 | 10/2009 | Reiley | |
| 2011/0230966 A1* | 9/2011 | Trieu | A61B 17/562 623/17.12 |
| 2011/0238181 A1* | 9/2011 | Trieu | A61B 17/1735 623/17.11 |
| 2012/0191191 A1 | 7/2012 | Trien | |
| 2013/0218215 A1 | 8/2013 | Ginn et al. | |
| 2014/0031935 A1* | 1/2014 | Donner | A61F 2/4455 623/17.11 |
| 2014/0277165 A1 | 9/2014 | Katzman et al. | |
| 2014/0277463 A1* | 9/2014 | Yerby | A61F 2/32 623/17.11 |
| 2015/0080972 A1 | 3/2015 | Chin et al. | |
| 2016/0058475 A1* | 3/2016 | Wanderley | A61B 17/3472 600/584 |

* cited by examiner

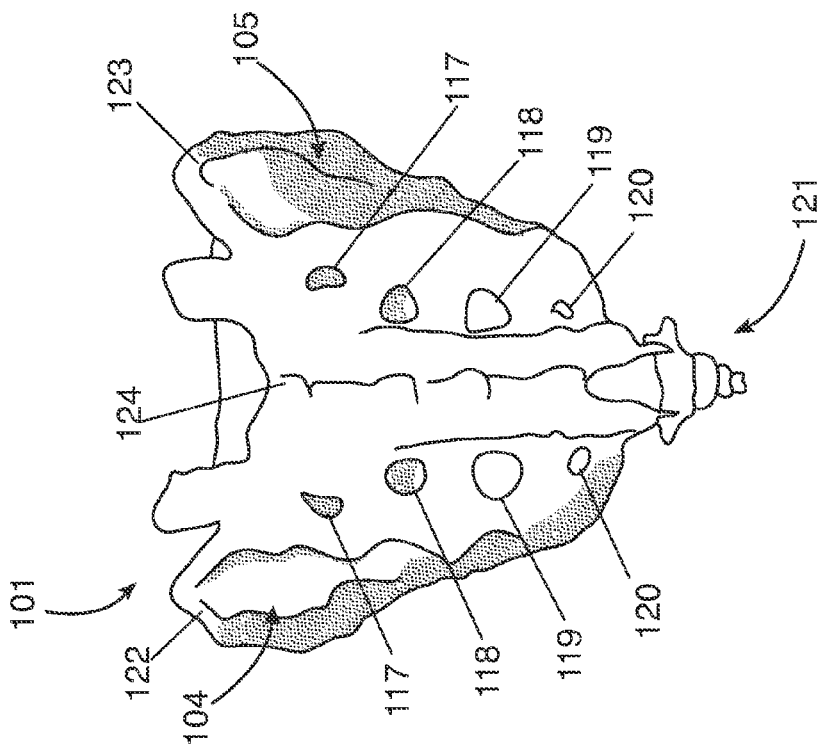
FIG. 1 continued
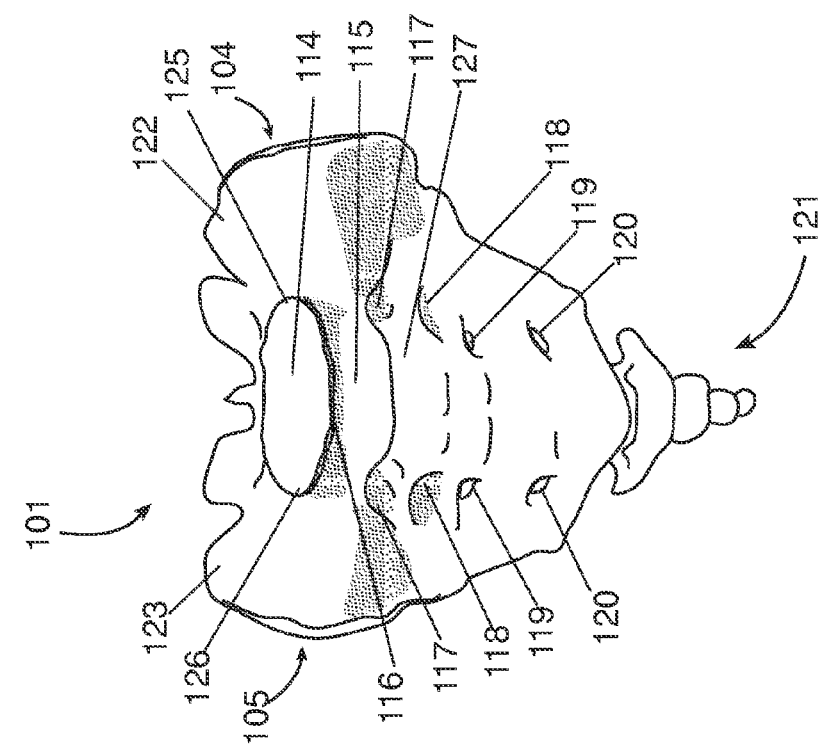

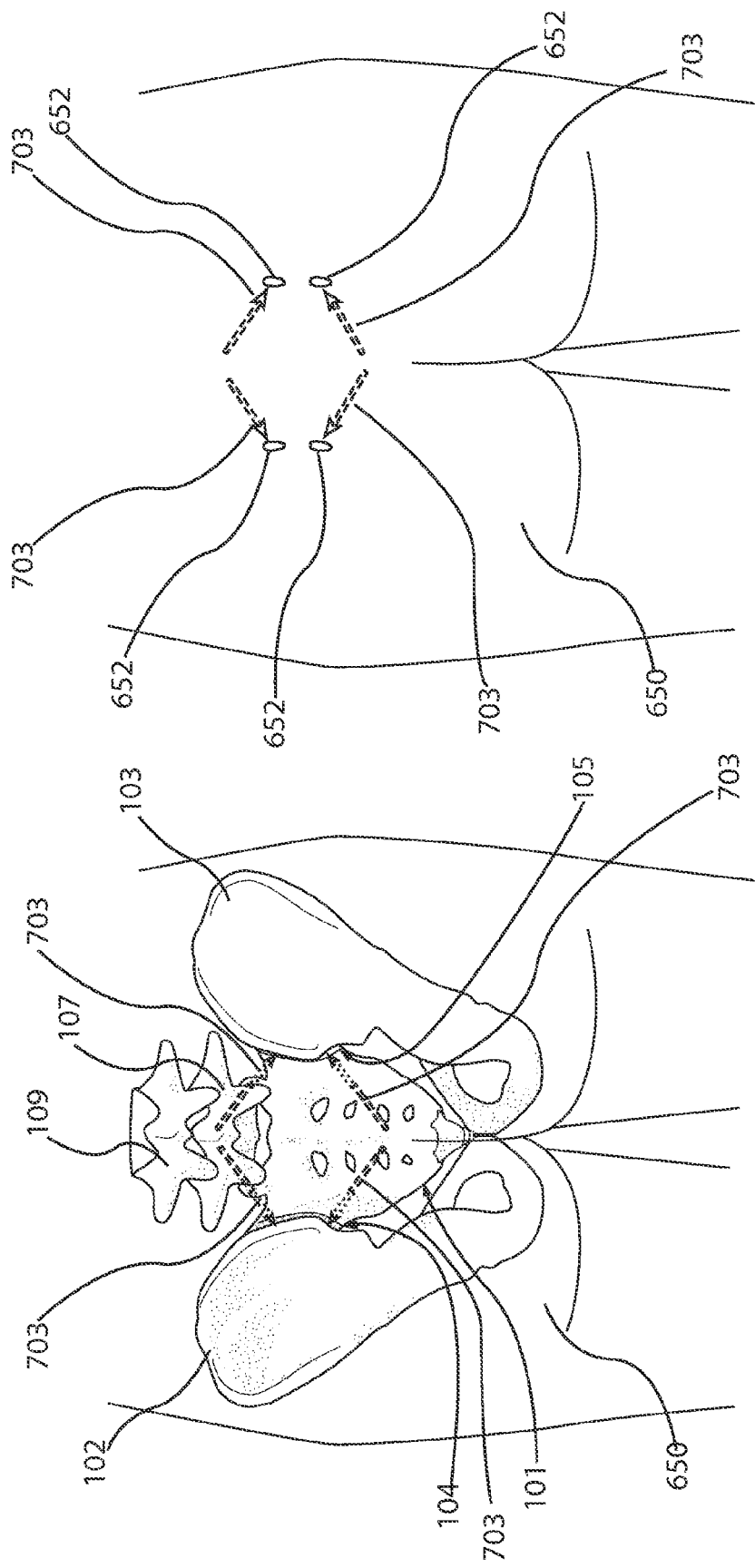

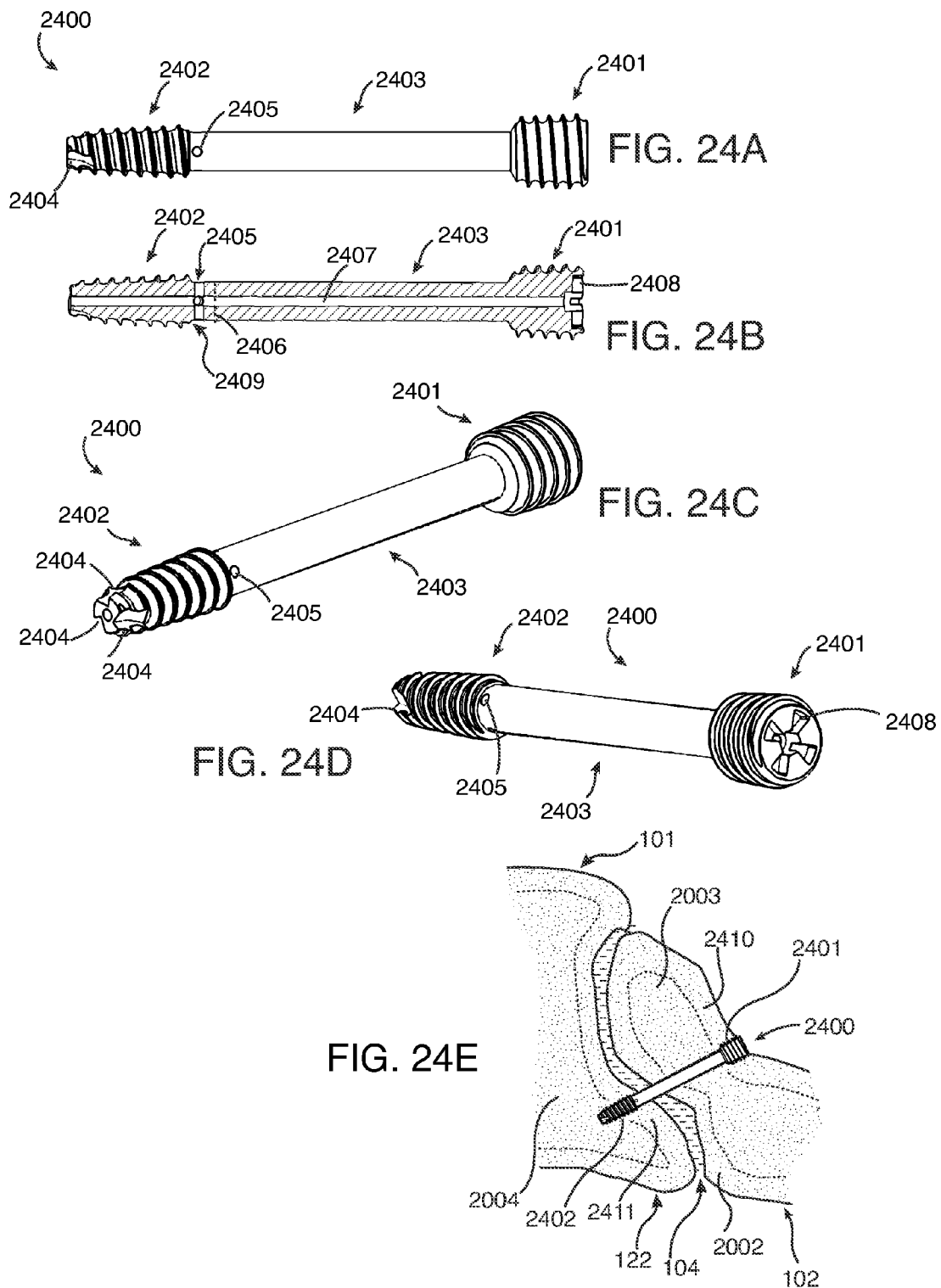

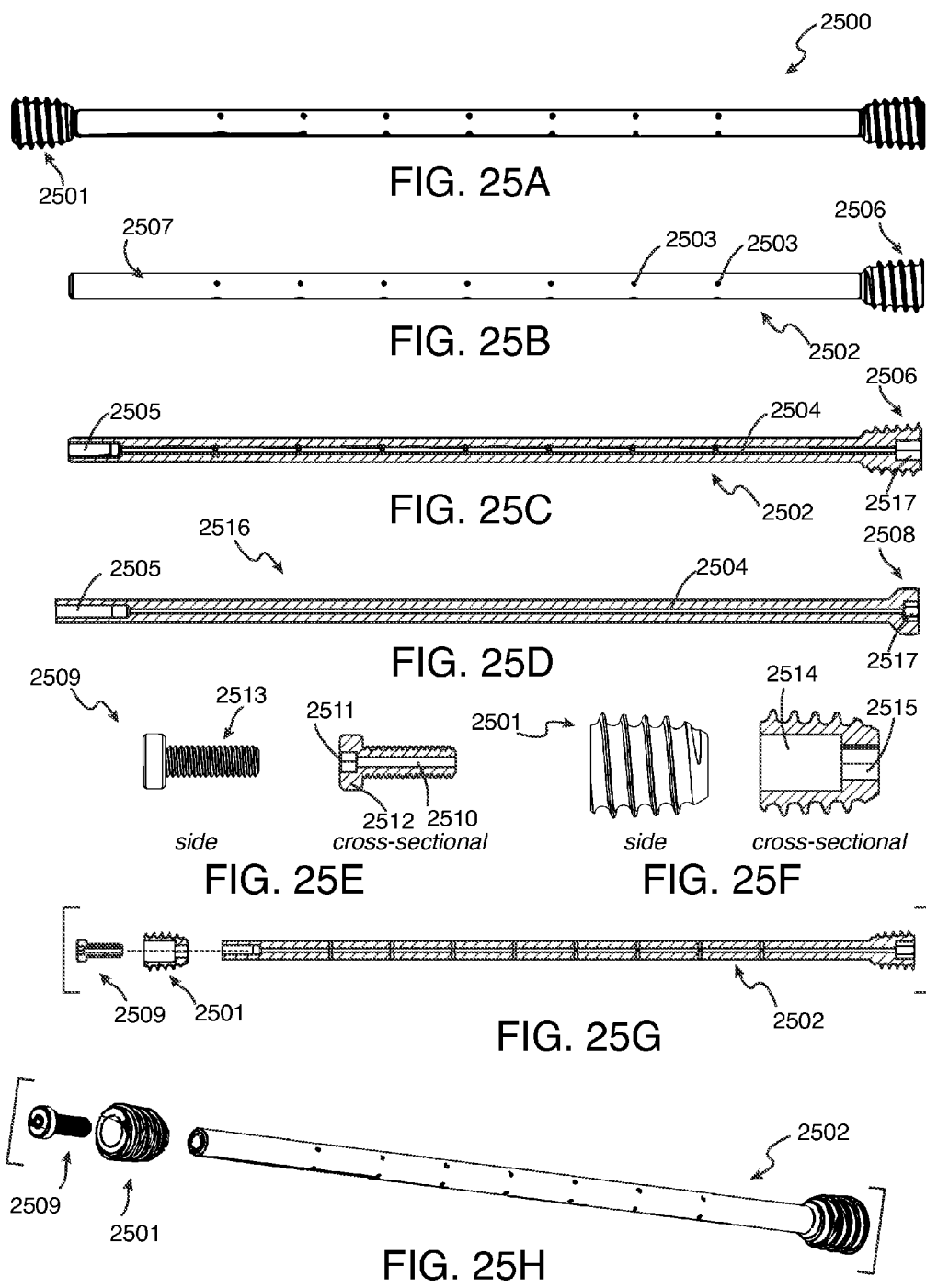

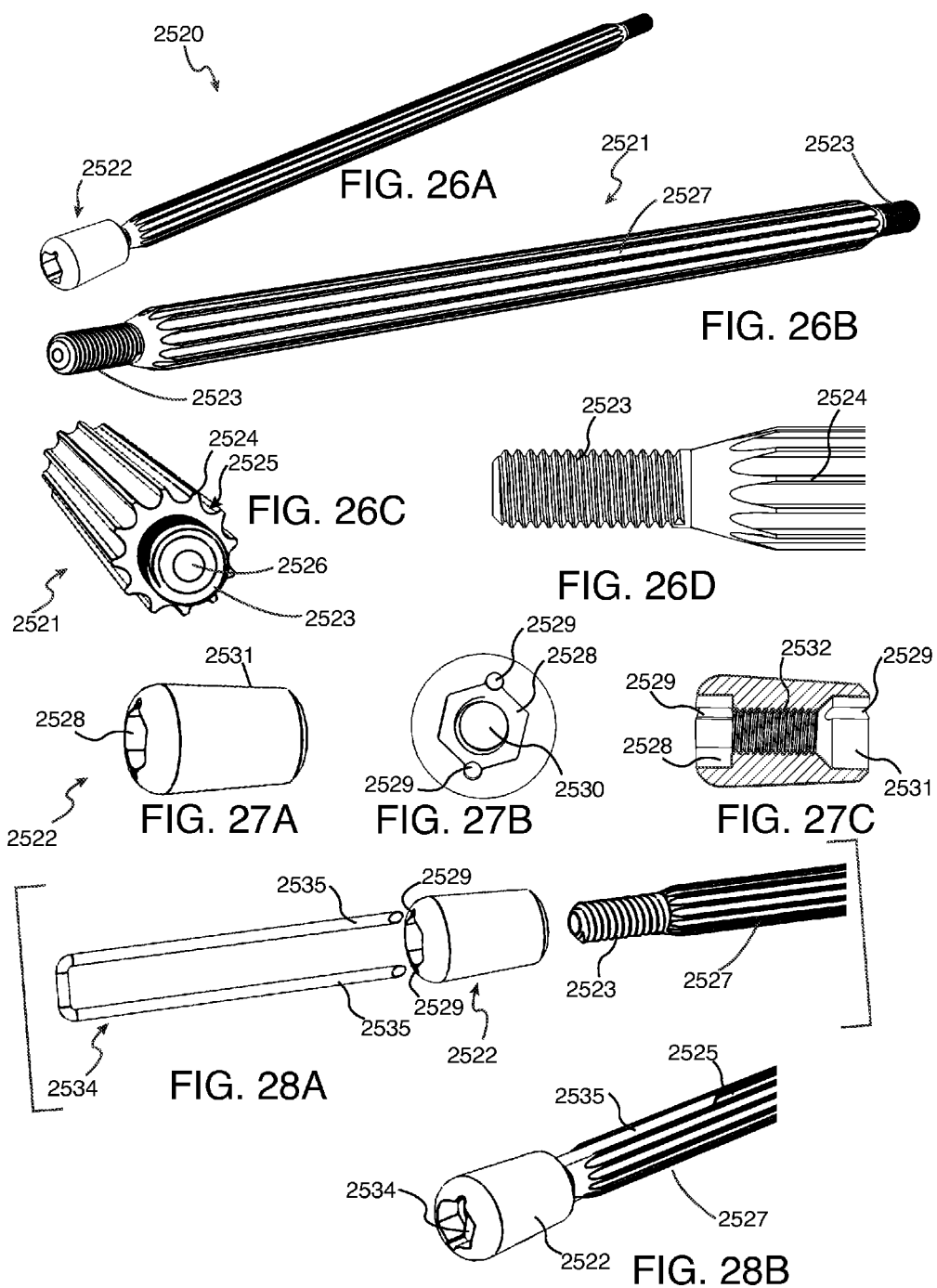

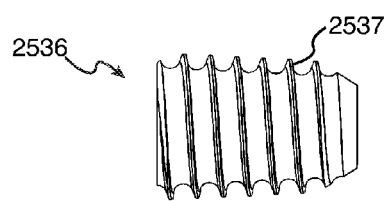 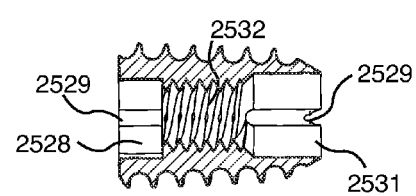
FIG. 29A   FIG. 29B
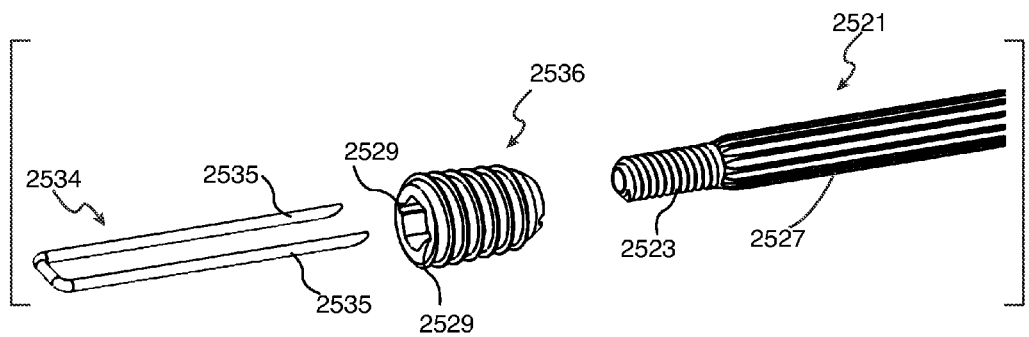
FIG. 29C

MINIMALLY INVASIVE APPROACHES, METHODS AND APPARATUSES TO ACCOMPLISH SACROILIAC FUSION

CROSS REFERENCE TO RELATED APPLICATIONS

The present application claims the benefit of U.S. provisional application 62/068,602, filed Oct. 24, 2014, and provisional application 62/105,045, filed Jan. 19, 2015. The entire disclosures of the above references are incorporated herein by reference in entirety for all purposes.

FIELD OF THE INVENTION

The field relates generally to a medical procedure, and more particularly to a medical process of the sacroiliac joint.

BACKGROUND

Problems associated with the weakening and inflammation of the sacroiliac joint, or "SI joint," are among the most prevalent causes of lower-back pain. Sacroilitis, or sacroiliac joint dysfunction, is inflammation of one or both SI joints that can lead to extensive pain in the lower back region. Causes of sacroilitis include trauma of the lower back from injury, osteoarthritis of the spine, and infection of the SI joint. Additionally, childbirth is a common causative event for sacroilitis, as pelvic widening and expansion of one or both sacroiliac joints associated with vaginal childbirth can lead to spraining of the ligaments associated with the SI joint. Incidentally, the majority of those diagnosed and treated for sacroilitis are women.

The SI joint is the interface between the sacrum and the left ilium or right ilium. The SI joint is a synovial joint having weight-supporting and shock-absorbing properties. The SI joint is further structurally stabilized with a series of ligaments comprising the anterior, interosseous, posterior, sacrospinous, and sacrotuberous ligaments. Pain associated with the SI joint commonly occurs from increased unwanted movement of the joint that increases movement of the sacrum and/or ilium.

According to a study administrating a series of standardized questionnaires to patients undergoing SI joint treatment, sacroilitis contributes to a significant burden on the health status of a patient. Burden on the quality of life associated with sacroilitis is higher than many other disabling medical conditions, including, for example, COPD, coronary heart disease, and angina (Cher D., et. al. 2014. Sacroiliac joint pain: burden of disease. *Med. Devices: Evidence and Res.* 7:73-81). The economic impact in the U.S. of annual expenditures associated with chronic back pain is also significant, with approximate costs ranging from $12 billion to $90 billion in direct costs, and $7.4 billion-$13.9 billion in indirect costs (Dagenais, S., et. al. 2008. A systematic review of low back pain cost of illness studies in the United States and internationally. *Spine J.* 8: 8-20). The prevalence of SI joint pain varies from 15% to 30% of patients having lower back pain (Szadek K M. et. al. 2009. Diagnostic Validity of Criteria for Sacroiliac Joint Pain: A Systematic Review. *J Pain.* 10(4): 354-368). In some cases, fusion of the SI joint is an important option for patients with lower back pain.

In some cases, fusion of the SI joint is an important option for those suffering lower back pain. Fusion of the SI joint can effectively treat SI joint dysfunction that directly results from SI joint disruptions and degenerative sacroilitis. Methods and procedures to surgically accomplish a SI joint fusion are regularly performed as needed to stabilize the SI joint and relieve painful symptoms caused by SI joint disruptions or degenerative sacroilitis.

Furthermore, there is generally a demand for surgical procedures that are minimally invasive. As evidenced by retroactive studies comparing the minimal clinically important difference (MCID) measurements, recipients of a minimally invasive SI joint fusion procedure statistically had greater improvements in lower back pain alleviation (as measured by Oswestry Disability Index (ODI)), less blood loss, decreased operation time, and decreased length of hospital stay as compared to recipients of open anterior SI joint fusion procedures (Ledonio C G, et. al. 2014. Comparative effectiveness of open versus minimally invasive sacroiliac joint fusion. *Med. Devices: Evidence and Res.* 7: 187-193; Ledonio C G., et. al. 2014. Minimally invasive versus open sacroiliac joint fusion: are they similarly safe and effective? *Clin. Orthop. Relat. Res.* 472(6): 1831-1838). However, no surgical intervention adequately and securely fuses the SI joint without problems associated with prior art procedures, such problems including a substantial level of trauma, pain and a long recovery time. Many traditional methods and procedures associated with SI joint fusion require open, non-minimally invasive procedures, often causing an elevated level of trauma, greater pain and a longer recovery time for the subjects of such methods and procedures.

A variety of forces impact the hip area. For instance, the SI joint is responsible for supporting the weight of a person's body. Moreover, anatomical features associated with and located within and near the hip area must facilitate a great deal of movement. Traditional methods often involve the placement of instrumentation in the lumbar spine medial to lateral to the sacral iliac joint. The reliance upon a single screw to secure the SI joint, as associated with several prior art procedures, is often insufficient to effectively stabilize the SI joint. Although a plurality of anchoring implants have also been used within the SI joint area, as disclosed in U.S. Pat. No. 8,734,462 and elsewhere, the weight and movement forces that the various anatomical structures related to and near the hip area must face can potentially lead to a loosening of the screws and/or anchoring implants associated with such prior art surgeries.

Often, the failure of a SI fusion results from the utilization of previously known methods where devices placed in association with such methods will break. Such breakage occurs because of the excessive forces associated with the sacral iliac joint and anatomical structures located near the hip area. Previously known methods fail to adequately and effectively address these forces.

Because of the excessive forces the SI joint experiences, inadequate SI joint fusions deriving from previously known methods can lead to a variety of problems. After a typical previously known surgical procedure intended to address problems associated with the SI joint, mechanical stress on the bone surrounding the SI joint and anchoring implants placed during such procedure may further degrade the bone surrounding the anchoring implants, leading to pseudoarthrosis, costly and risky return surgery, complications, and failed clinical outcome. Such problems also include without limitation the failure of associated instrumentation, the breakage of associated instrumentation, and continued undesirable motion of the SI joint.

The anatomical structure of the SI joint, bone structure, spacing in association with the SI joint and resultant accessibility to the SI joint may vary among differing patients.

Several previously known minimally invasive methods and procedures require the placement of an implant. However, in some cases, the SI joint space may not be sufficiently accessible to accommodate such an implant given the anatomical structure of a patient.

The more recent laterally-placed procedures allow for implants to be placed across the joint space. Recent developments in technology associated with bone fusing materials including bone graft and bone graft substitutes, enable the strengthening of two pieces of bone. Many such procedures involve the full decortication of the articular surfaces of a joint prior to filling the joint space with bone graft and bone graft substitutes. However, many previously known methods and procedures related to the SI joint fail to take advantage of such recent developments in technology. Such methods and procedures often fail to effectively and adequately accomplish bony fusion using allograft, auto graft or structural implants within the joint space. Some prior art procedures and methods fail to effectively incorporate the use of bone or bone substitutes placed deep within the joint, and thereby often result in suboptimal bone fusion, breakage of instrumentation and pseudoarthrosis. Some methods and procedures involve the placement of bone grating through or in the region of the sacral iliac joint, however a related problem is that the placement of the bone generally does not take place deep into the joint. As a result, poor sacral iliac fusions thereby result from the suboptimal placement of bone.

For example, a United States patent (U.S. Pat. No. 8,734, 462) specifically discloses the use of anchoring implants comprising porous plasma coated titanium to facilitate the fusion adjacent to the anchoring implants within the embedded bone. Yet, in such prior art, the problem of potential movement between the sacrum and ilium after the surgery remains unsolved. Such previously known methods and apparatuses fail to take advantage of the benefits associated with the cleaning and decortication of the articular surfaces and the addition of bone graft materials within the joint space. A previously unsolved problem therefore is a failure to effectively combine the use of biological grafts within the SI joint with mechanical compression of such joint.

Further, some previously known methods and procedures associated with the SI joint lack the percutaneous placement of screws, where open placement of screws is more common. The trauma associated with open placement of screws associated with prior art procedures causes an elevated risk of nerve, abdominal, and vascular injuries, excessive tissue trauma, hematomas, and infections of soft tissues.

Additionally, some of the more recent techniques do not allow for the direct visualization of the bony joint surface, which is considered a preferred method of surgery in some cases and often a requirement mandated by insurance companies to receive reimbursement for fusion procedures. Moreover, there is a risk that prior art procedures and methods leading to a high incidence of pseudoarthrosis, instrumentation failure, and poor clinical outcomes.

While improvements have been made in decreasing the invasiveness of the minimally invasive SI joint surgeries, previously known techniques and methods associated with minimally invasive SI joint surgeries still pose a significant risk for complications. For example, depending on the site of the incision, the chance of hematoma (collection of blood outside of blood vessels) and/or infection increases with the size of the surgical incision. While previously known minimally invasive SI joint procedures have smaller incision sites than open anterior SI joint fusion procedures, the incisions associated with such minimally invasive SI joint procedures still feature lengths between 3 cm and 5 cm or longer. Therefore, such incisions and associated instrumentation related to previously known minimally invasive SI joint procedures have a significant potential to cause damage to tissue, nerves, and bone structures. These also lead to a substantial risk of hematoma and/or infections during and after surgery. Furthermore, by creating a larger incision site, the larger incision site becomes more problematic in cases where the entry site for the corresponding implant needs to be changed during the surgery.

More recently, there has been progress in the field of unilateral SI joint fusion procedures wherein either the left SI joint or right SI joint is stabilized one at a time or in conjunction during the same operation. Progress made in minimally invasive SI joint fusion approaches, as described in the provisional U.S. patent application, U.S. 62/068,602, in general, provide vast improvements as compared to typical prior art unilateral SI fusion procedures. For example, in U.S. patent application, U.S. 62/068,602, the creation of a small incision (approximately 1 to 2 cm), and corresponding instruments that are able to access the SI joint through said small incision aperture, generally reduces nerve/tissue/blood vessel damage, hematoma and/or infections during and after surgery, as compared to prior art inventions that require larger incision openings. Moreover, the decortication of SI joint material, and further filling the decorticated SI joint space with bone fusion material prior to mechanically securing the sacrum and ilium with a stabilizing device, enable added stability to the SI joint. Therefore, U.S. patent application, U.S. 62/068,602, in general, reduces the number of steps, reduces the number of instruments, decreases the size of the surgical wounds, and increases the stability of the SI joint as compared to typical prior art SI Fusion procedures.

In some cases, a patient, insurance provider, and/or doctor may elect to perform a single unilateral SI joint fusion, on just one side of the hip. However, it has been observed that approximately one in five patients have complained of bilateral pain, or pain in both the left and right SI joints. In such cases, doctors elect to perform SI joint stabilization of both SI joints. Of patients that have undergone single unilateral SI joint fusion, some patients post-operatively complain of discomfort and/or pain related to the SI joint on the other side. This additional discomfort and/or pain may occur because of the imbalance of the stabilization when only one SI joint is secured. In typical cases, patients may require further surgery to stabilize the SI joint located on the other side to reduce said discomfort and/or pain.

Prior art SI joint fusions that aim to simultaneously secure both the left and right SI joints, wherein both SI joints are stabilized simultaneously during a single operation, has been described. The Dorsal Bilateral Interlocking Technique stabilizes the SI joints by placing an external fixator between the anterior-superior iliac spine of both ilia such that said fixator secures both ilia on the posterior side of the hip. The SI joints are further stabilized by placing lag screws to secure an ilium to the sacrum in a posterior-lateral to an anterior-medial direction. The process of securing both the left and right SI joints, has been previously reported to be ineffective. In one particular retroactive analysis of a cohort of patients that have undergone a Dorsal Bilateral Interlocking SI joint Fusion, the majority of the patients of the cohort did not have clear or any SI joint fusion, and only temporary or no improvements in symptoms or activities of daily living (Schutz, U and D. Grob. 2006. Poor outcome following bilateral sacroiliac joint fusion for degenerative sacroiliac joint syndrome. Acta. Orthop. Belg. 72: 296-308.). Furthermore, the Dorsal Bilateral Interlocking Technique and other prior art procedures are generally invasive and require a large surgical wound (typically a 10 to 15 cm incision) of the posterior region of the body, wherein the large surgical wound has significant potential to cause damage to tissue, muscle, nerves, and bone structures, and access to the appropriate spinal structures to achieve fusion further requires temporary displacement and/or removal of tissue, muscle, nerves, and other bodily structures. An obvious side-effect to these invasive procedures is that they have substantial risk of causing hematoma and/or infections during and after surgery due to the large size and great impact to the surgical site. Therefore, there is a need for a minimally invasive procedure that simplifies stabilization of both the left and right SI joint, and associated devices that enable said stabilization.

BRIEF DESCRIPTION

Certain embodiments and variations of the invention relate to a medical procedure and apparatuses for SI joint stabilization and fusion. The present disclosure presents novel methods, procedures associated steps, and apparatuses to accomplish SI joint fusion in a minimally invasive manner. The preferred embodiment of the invention incorporates improved methods, procedures and apparatuses to facilitate a SI joint fusion providing a generally safer, more minimally invasive SI joint stabilization.

BRIEF DESCRIPTION OF THE DRAWINGS

FIG. 1B. Representative anterior view of a sacrum.
FIG. 1C. Representative posterior view of a sacrum.

FIG. 18A. Posterior view of a patient's pelvic region showing an embodiment of the oblique paths in relation to associated bone structures.

FIG. 18B. Posterior view showing an embodiment of the oblique paths and incisions in relation to a patient's posterior.

FIG. 24A. A side view of an embodiment of a stabilizer device.

FIG. 24B. A side, cross-sectional view of an embodiment of a stabilizer device.

FIG. 24C. A perspective view of an embodiment of a stabilizer device.

FIG. 24D. A perspective view of an embodiment of a stabilizer device.

FIG. 24E. A cross sectional view of the left sacrum, left ilium, and left SI Joint from the superior-inferior view with an embodiment of a stabilizer device used to secure the SI joint.

FIG. 25A. A side view of an embodiment of a bilateral device.

FIG. 25B. A side view of an embodiment of a bilateral device component.

FIG. 25C. A side, cross-sectional view of an embodiment of a bilateral device component.

FIG. 25D. A side, cross-sectional view of an embodiment of a bilateral device component.

FIG. 25E. A side view, and a cross-sectional view of an embodiment of an end screw.

FIG. 25F. A side view, and a cross-sectional view of an embodiment of a floating screw.

FIG. 25G. An exploded, cross-sectional view of an embodiment of a bilateral device.

FIG. 25H. An exploded, perspective view of an embodiment of a bilateral device.

FIG. 26A. A perspective view of an embodiment of a stabilizer device, where one wedge end screw is removed.

FIG. 26B. A perspective view of an embodiment of a stabilizer device component.

FIG. 26C. A perspective view of an embodiment of a stabilizer device component showing splines and grooves.

FIG. 26D. A close-up view of an embodiment of a stabilizer device component's end.

FIG. 27A. A perspective view of an embodiment of a wedge end screw.

FIG. 27B. A top view of an embodiment of a wedge end screw.

FIG. 27C. A side cross-sectional view of an embodiment of a wedge end screw.

FIG. 28A. An exploded view of an embodiment of a bilateral device having a locking pin.

FIG. 28B. A perspective view of an embodiment of a bilateral device having a locking pin in place.

FIG. 29A. A side view of an embodiment of an end screw.

FIG. 29B. A side cross-sectional view of an embodiment of an end screw.

FIG. 29C. An exploded view of an embodiment of a bilateral device having a locking pin.

DETAILED DESCRIPTION

Overview

The present invention relates to improved methods, procedures and apparatuses associated with the fusion of the sacrum and an ilium, and the sacrum and both ilia. As associated with embodiments of the invention, a "sacroiliac fusion approach", and a "transsacral bilateral sacroiliac fusion approach" generally relate to a medical procedure intended to address undesirable movement associated with articular surfaces of the sacrum and an ilium.

In the method associated with the preferred embodiment of the invention, in one aspect, a path or a plurality of paths through an ilium to the sacrum is established, wherein a stabilizer device allows the securement of the sacrum to the ilium. In another aspect, a path or a plurality of paths to the SI joint is established, where bone fusion material allows fusion of the articular surface of the ilium and the articular surface of the sacrum of an SI joint.

Figure 1A:
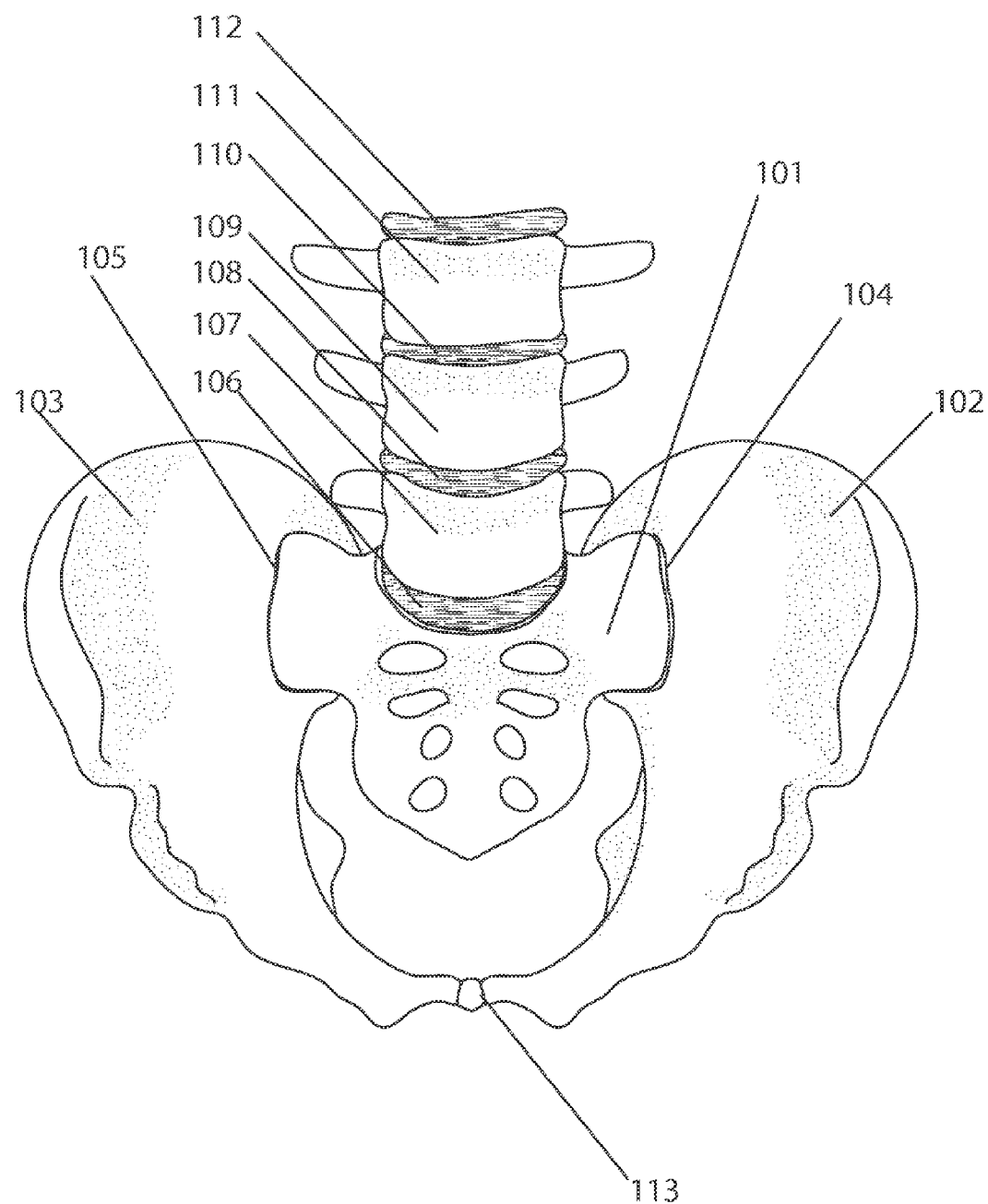
FIG. 1A. Anterior view of certain bones in a pelvic region.

In certain embodiments of the invention, a procedure is performed in the general vicinity of the pelvis. In certain embodiments of the invention, a procedure can be performed either on the left sacroiliac joint 104 and/or the right sacroiliac joint 105 to stabilize such joints. In certain embodiments, a procedure is performed in and near the left sacroiliac joint 104 and the right sacroiliac joint 105 to stabilize said joints. In general, the left sacroiliac joint 104 includes the sacrum 101 and the left ilium 102, and the right sacroiliac joint 105 includes the sacrum 101 and the right ilium 103. Other vertebral structures in the vicinity of a representative pelvis are shown in FIG. 1A, such as the L5-S1 intervertebral disc 106, the L5 Vertebra 107, the L4-L5 intervertebral disc 108, L4 Vertebra 109, L3-L4 intervertebral disc 110, L3 Vertebra 111, L2-L3 intervertebral disc 112, and the pubic symphysis 113. In certain embodiments, a procedure is performed in association with other structures located in or around a pelvis. For example, as illustrated in an anterior to posterior view of an exemplary sacrum in FIG. 1B, and a posterior to anterior view of a sacrum in FIG. 1C, other typical anatomical structures of the sacrum are shown, for instance, the S1 superior endplate 114, S1 vertebral body 115, the sacral promontory 116, S1 foramen 117, S2 foramen 118, S3 foramen 119, S4 foramen 120, coccyx 121, left sacral ala 122, right sacral ala 123, and the sacral canal 124.

The general process of embodiments of a sacroiliac fusion approach and a transsacral bilateral sacroiliac fusion approach occurs after anesthesia, disinfection, and other standard procedures and practices related to surgery and/or spinal surgeries known to persons having ordinary skill in the art. In certain embodiments, a patient is placed under general anesthesia, or optionally remain conscious, and/or otherwise be placed under a general or local analgesic for the duration of the methods and procedures described herein. In certain embodiments of the invention, a sacroiliac fusion approach and a transsacral bilateral sacroiliac fusion approach is performed on a patient placed in a prone position.

A Unilateral Sacroiliac Fusion Approach

General Steps

Figure 2A:
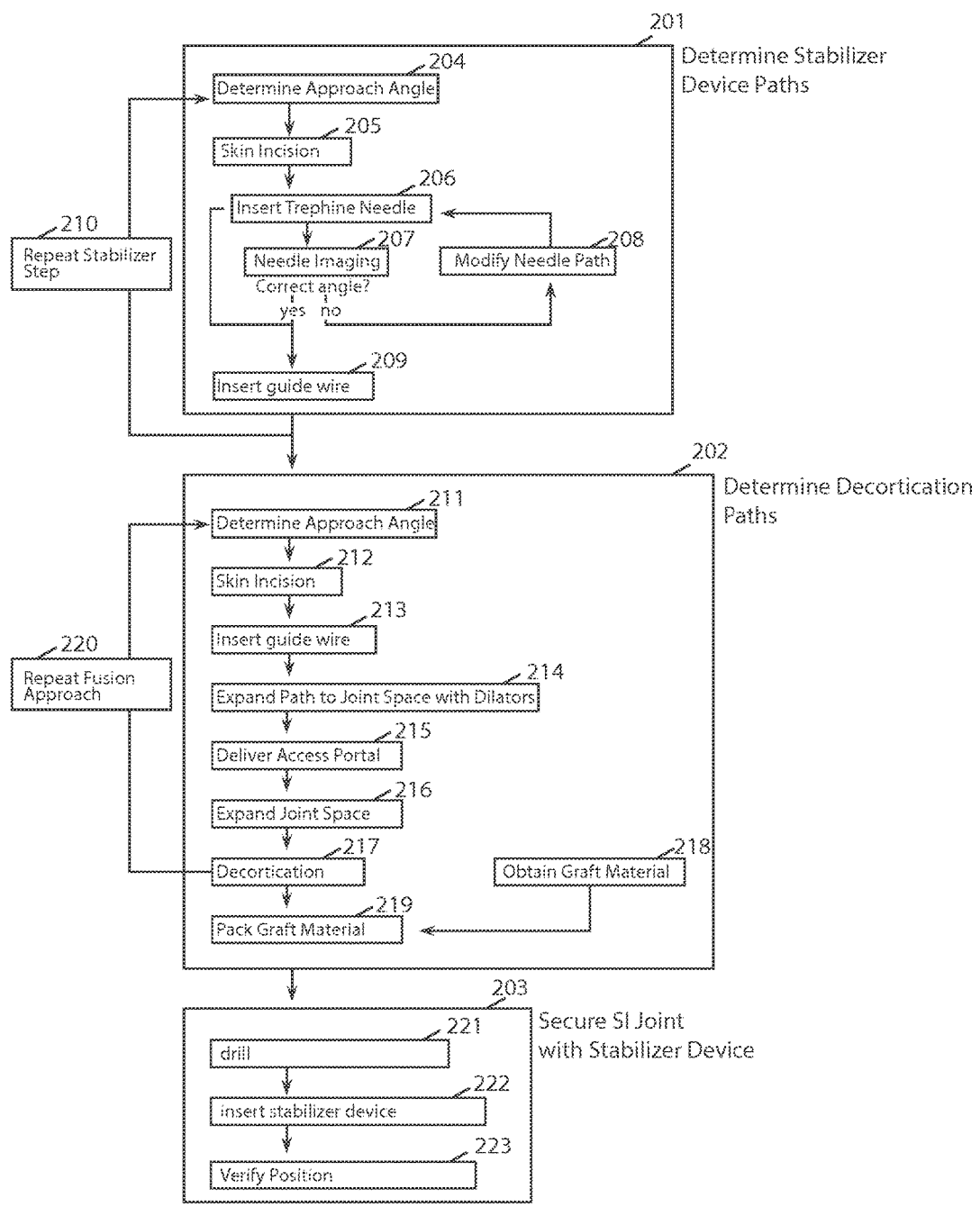
FIG. 2A. Flow diagram of the general procedure of the sacroiliac fusion approach in certain embodiments of the invention.

The general procedure for a unilateral sacroiliac fusion approach associated with certain embodiments is illustrated in a flow diagram in FIG. 2A. The flow diagram, as represented in FIG. 2A, is shown for demonstrative purposes as a general outline of a sacroiliac fusion approach and is meant to be encompassing rather than limiting. After anesthesia, disinfection, and other standard procedures and practices related to surgery and/or spinal fusions known to persons having ordinary skill in the art, a medical practitioner performs steps represented in embodiments of the invention described in FIG. 2A.

As represented in FIG. 2A, certain embodiments of the sacroiliac fusion approach has the following steps: 1) determine stabilizer device paths step 201; 2) determine decortication paths step 202; and 3) secure SI joint with stabilizer device step 203. In embodiments of the invention, there are two general approaches for entry per each SI joint. Such approaches, herein referred to as a "stabilizer device approach" and a "decortication approach," are distinguished by the general purpose and location of entry into the anatomical structures within a pelvic region. Furthermore, in certain embodiments, a number of surgical devices related to orthopedic surgery, including, but not limited to syringes, trephine needles such as Jamshidi® needles, cannulae, endoscopes, guide wires, drills, dilators, tubes, curettes, are used for access and entry into the pelvic region through the two general approaches. A variety of medical instruments, including those described below may be used in association with certain embodiments of the decortication approach.

Stabilizer Device Approach

Figure 3A:
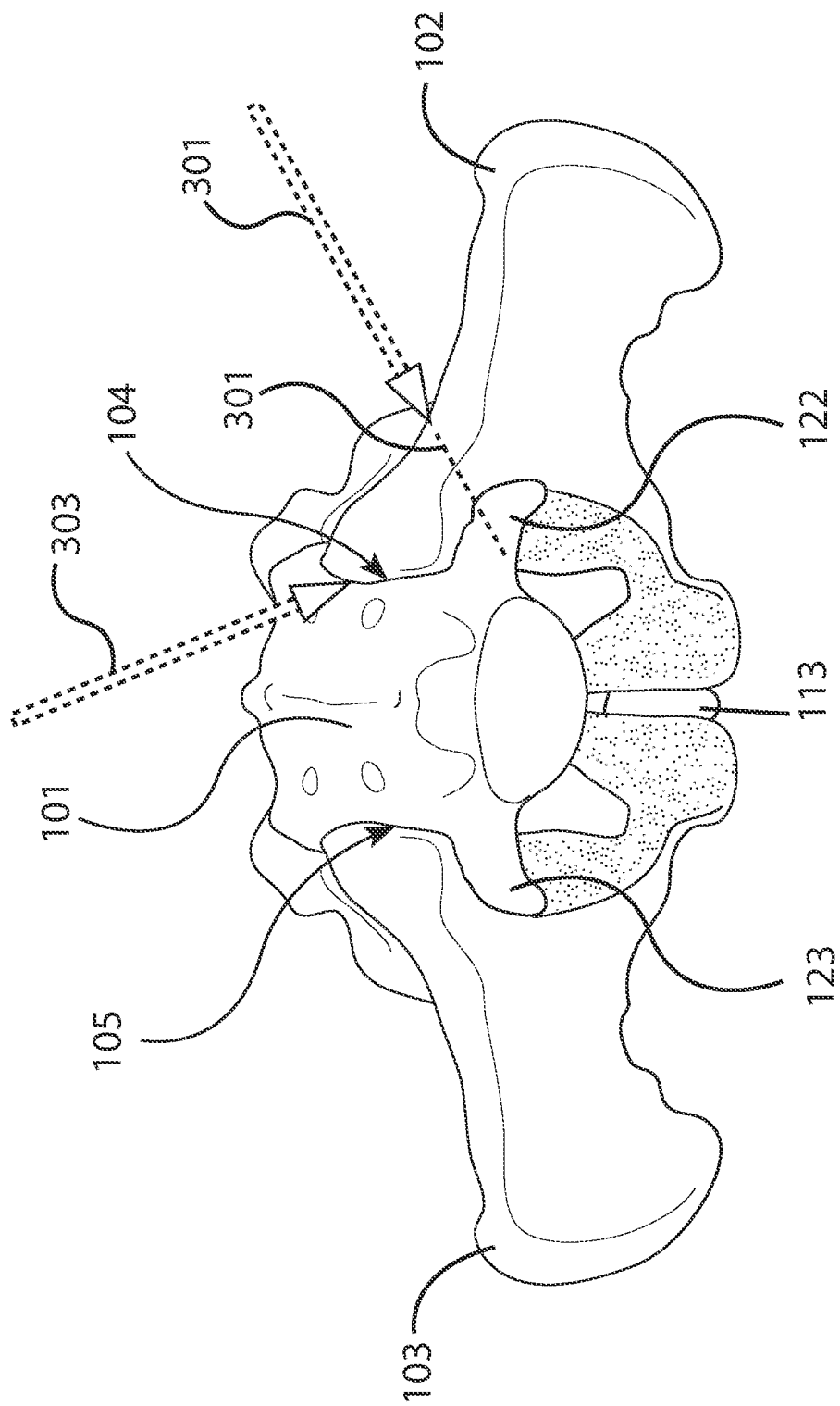
FIG. 3A. The stabilizer device approach and decortication approach viewed from a superior-inferior angle of a pelvis in certain embodiments of the invention.

In certain embodiments of the invention, the stabilizer device approach 301 is a general pathway that allows compression and stabilization of the sacrum and ilium during the sacroiliac fusion approach. As illustrated in a representative example for the left SI joint in FIG. 3A, a stabilizer device approach 301, in general, traverses through an ilium 102 to reach the sacrum 101, generally passing through a cortical bone layer of such sacrum. The angle of approach of a stabilizer device approach 301 to the sacrum 101 is in general more lateral and posterior, as shown in FIG. 3A of a superior-inferior view of the pelvis. It will be appreciated that in certain embodiments, an approach 301 is preferably orthogonal or close to orthogonal (for instance approximately 90°, 85°, 80°, 75°, 70°, 65°, 60°, 55°) to a plane of an SI joint. In certain embodiments, such approach 301 may be orthogonal or close to orthogonal to a plane of a surface of an ilium. In embodiments of the invention, a plurality of the stabilizer device paths 701, as shown for example in FIG. 4A and FIG. 4B, may follow a stabilizer device approach 301.

Decortication Approach

Figures 4A, 4B:
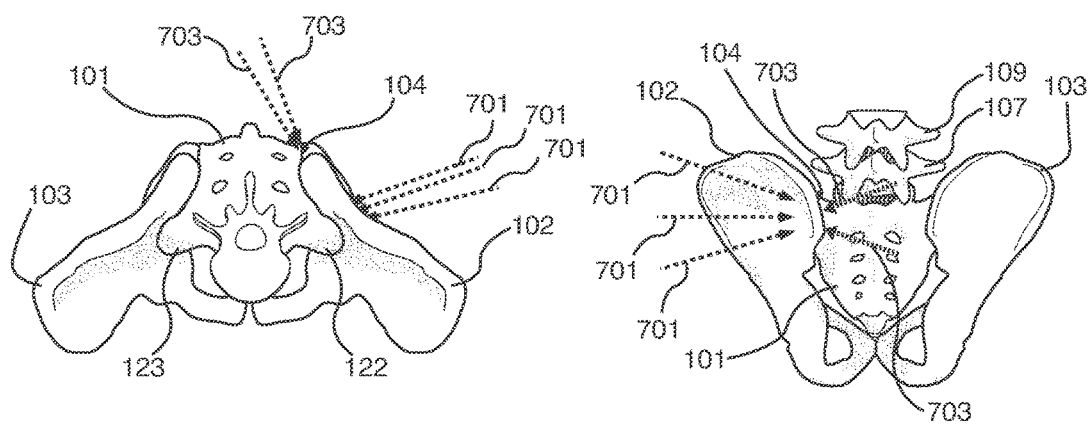
FIG. 4A. Stabilizer device paths and oblique paths viewed from a superior-inferior angle of a pelvis in certain embodiments of the invention.
FIG. 4B. Stabilizer device paths and oblique paths viewed from a posterior view of a pelvis in certain embodiments of the invention.

A decortication approach 303, as shown in FIG. 3A, advances towards the SI joint at an oblique angle, and at an angle that is in general more posterior and lateral. A decortication approach 303 is a pathway that allows access to and removal of SI joint material, for instance, cartilage, or portions of cortical bone, and through which a medical practitioner may add bone fusion material for bony fusion of the sacrum and ilium. A decortication approach 303 is in a plane that is, in general, parallel to the plane of the SI joint, or extends from a posterior-medial point to an anterior-lateral point of the patient. In certain embodiments, a plurality of oblique paths 703, as shown in FIG. 4A and FIG. 4B, may be on a similar plane as a decortication approach 303, shown in FIG. 3A. Together, in certain embodiments of the invention, a medical practitioner accesses an SI joint with two general trajectories, including, but not limited to a stabilizer device approach 301 and a decortication approach 303.

Steps Associated with Establishing Stabilizer Device Paths

In certain embodiments of the invention, as shown in FIG. 2A, a determine stabilizer device paths 201, has a number of sub-steps, including, but not limited to: 1) determine approach angle step 204; 2) skin incision step 205; 3) insert trephine needle step 206; 4) needle imaging step 207; 5) modify needle path step 208; 6) insert guide wire step 209; and 7) repeat stabilizer step 210. However, other embodiments of the invention are not limited to these sub-steps, and such sub-steps are meant to be exemplary rather than limiting. It will be appreciated that certain steps, procedures, and instruments, related to step 201 have similarities with the determine stabilizer device paths step 251 shown in FIG. 2B.

In general, a determine stabilizer device paths step 201 allows a medical practitioner to establish one or a plurality of stabilizer device paths 701 in a minimally invasive manner. In certain embodiments one or more stabilizer device paths 701 are created for the purpose of stabilizing the sacrum and an ilium, per SI joint (per side of a pelvis). However, in other embodiments of the invention, the sacroiliac fusion approach may include between 1 and 7 stabilizer device paths 701 per SI joint. Referring to FIG. 4B, showing a posterior view of the pelvic region, a plurality of stabilizer device paths 701 are in general, non-parallel, converging towards the sacrum. It will be appreciated that by following a non-parallel path, a plurality of stabilizer devices can traverse a larger surface area of the sacral and iliac bone and the SI joint space, and further help to stabilize the sacrum and ilium, as compared to using stabilizer device paths that are substantially parallel. However, it will be appreciated that in some cases, two or more stabilizer device paths 701 may be parallel, depending on, for example, an anatomical structure of a patient or availability of usable bone for stabilization with a stabilizer device.

During an embodiment of a determine approach angle step 204, a medical practitioner uses a needle as a reference, such needle having a radio-dense property, while viewing images through an imaging device. An imaging device, for example, a biplanar fluoroscopes (also referred to as C-Arm Fluoroscopes), or x-rays, captures images of the patient through various views, including but not limited to the lateral view and oblique view of a patient. In this step 204, a needle is adjusted so that a predicted path and angle of entry of such needle follows the general direction of a stabilizer device approach 301 as shown in FIG. 3A. In certain embodiments, a patient's pelvic region in the lateral view and/or the oblique view are referenced, during such step 204. A relative angle of a needle, or the relative location of a tip of a needle on the outer surface of a patient's skin is adjusted, so that when a potential path of such needle is extrapolated, such needle appears to take a path to reach the sacral ala from an ilium. The adjustments are made and verified by anticipating the path that a needle would take if, for example, a hypothetical straight line were extended from such needle to the sacral ala. The approach angle and/or incision site of the needle is adjusted and verified by referencing lateral-view and/or oblique images taken by a imaging device. It will be appreciated that instruments other than a needle having an oblong shape and being radio-dense may be used to predict a path, including but not limited to, for example, metal rods, and wires.

Figure 6A:
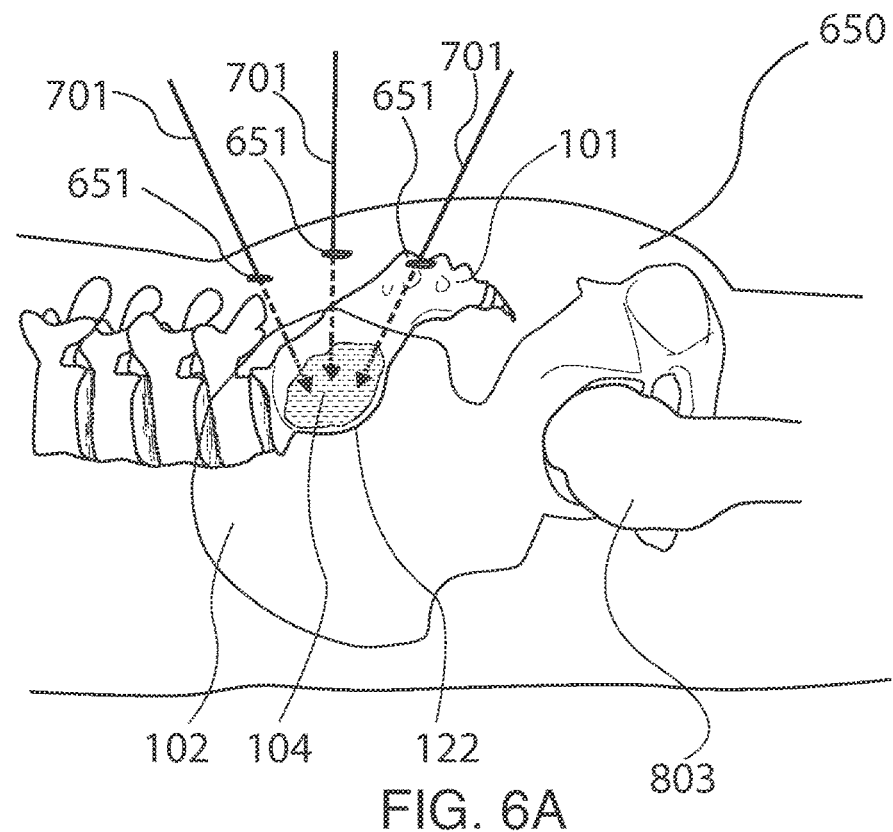
FIG. 6A. A lateral view showing stabilizer device paths towards the left SI joint in an embodiment, where a patient's skin and left ilium are transparently represented.
Figure 6B:
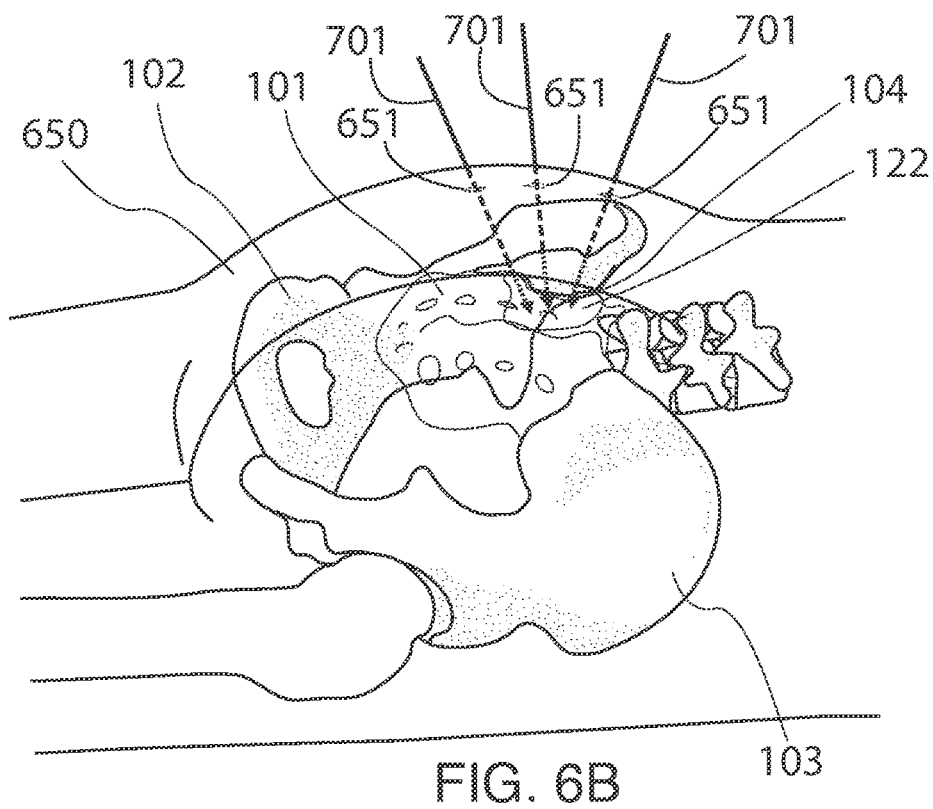
FIG. 6B. An oblique view showing stabilizer device paths towards the left SI joint in an embodiment, where a patient's skin and sacrum are transparently represented.

In one example, a sacroiliac fusion approach on the left SI joint is shown in FIG. 6A and FIG. 6B. A medical practitioner may reference a lateral view of the pelvis as illustrated in FIG. 6A, and/or an oblique view of the pelvis, as illustrated in FIG. 6B. An ideal stabilizer device path 701 would traverse the left ilium 102 and the left SI joint 104 to reach the left sacral ala 122. A medical practitioner would therefore take a plurality of images of a needle in relation to a patient's body, in a lateral view and/or oblique view, and such needle would be adjusted until the position of a needle, and a possible path extrapolated from such needle is ideal for SI joint fusion.

In certain embodiments of the invention, a skin incision step 205 is generally performed after the determine approach angle 204 step. It will be appreciated that an incision may be created with a medical instrument, such as a scalpel, known to those skilled in the art. In a skin incision step 205, an incision 651 that is approximately the size of a stabilizer device and/or size of the instruments utilized during the sacroiliac fusion approach is created, as shown in an example in FIG. 6A and FIG. 6B. In one example, as shown in FIG. 6A and FIG. 6B, an incision 651 is a length between 1 to 2 cm on a buttocks 650 but other sizes smaller or larger may be appropriate. In general, the size of such incision to create the incision 651 is matched to the size of the instruments utilized during the approach so as to minimize the invasiveness of the approach. As compared to some prior art methods that may require significantly larger incisions, certain embodiments of the sacroiliac fusion approach is intended to limit the size of an incision.

In certain embodiments, the insert trephine needle step 206, the needle imaging step 207, and the modify needle path step 208, relate to the establishment an initial path through the ilium and to the sacrum. A potential advantage of these steps is that it allows carefully refining an approach angle and/or approach path for each stabilizer device path 701. By carefully refining the approach angle and/or approach path while entering an ilium and sacrum, potential damage or non-ideal entry through an SI joint are avoided. Additionally, by carefully refining the approach angle and/or approach path using radiographic guidance, penetration of any of the instruments to the peritoneum beyond a distal cortical bone of a sacrum is avoided. By avoiding unnecessary drilling, the insert trephine needle step 206, the needle imaging step 207, and the modify needle path step 208 in certain embodiments have the advantage of increasing safety, reducing the time, and reducing the overall invasiveness of the sacroiliac fusion approach.

The insert trephine needle step 206 may include inserting a piercing tool or a trephine needle, such as a Jamshidi® needle or other device, that allows penetration through a bone structure. In certain embodiments, in the insert trephine needle step 206, the medical practitioner places a piercing tool typically having a sharpened tip to penetrate bone, at an approach path and approach angle as ascertained during the determine the approach angle step 204. The medical practitioner further taps such piercing tool or other related device to penetrate bone.

Following the insert trephine needle step 206, a needle imaging step 207 is performed to validate the approach angle and/or approach path of such tool, while the tool traverses an ilium. In the needle imaging step 207, the medical practitioner views the location and predicted trajectory of a piercing tool using images obtained from a imaging device. A medical practitioner refers to a lateral view and/or oblique view of the approach area, such as for example, x-ray images of both a lateral view and/or oblique view. If a piercing tool has an ideal or near ideal trajectory within the ilium that will traverse the SI joint and enter the sacrum, the medical practitioner returns to the insert trephine needle step 206. If a piercing tool does not have the trajectory to traverse the SI joint and enter the sacrum, or if the trajectory potentially causes damage to nearby nerves, the approach angle and/or approach path of a piercing tool are subsequently altered during the modify needle path step 208. An example of such alteration may include partially removing the tool and adjusting an angle of the tool. Once an alteration to a piercing tool is made during the modify needle path step 208, a medical practitioner continues with the insert trephine needle 206 step, where a medical practitioner may further tap a piercing tool through the iliac bone. In this manner, a medical practitioner adjusts the approach path and the approach angle of a piercing tool as it is placed through an ilium, an SI joint, and a sacrum. A medical practitioner continues with the insert trephine needle step 206, the needle imaging step 207, and modify needle path step 208 such that a piercing tool enters and traverses the SI joint, and further enters the sacrum. In certain embodiments, the insert trephine needle step 206, the needle imaging step 207, and modify needle path step 208 are completed once a piercing tool or other related device follows a stabilizer device path.

Figure 8A:
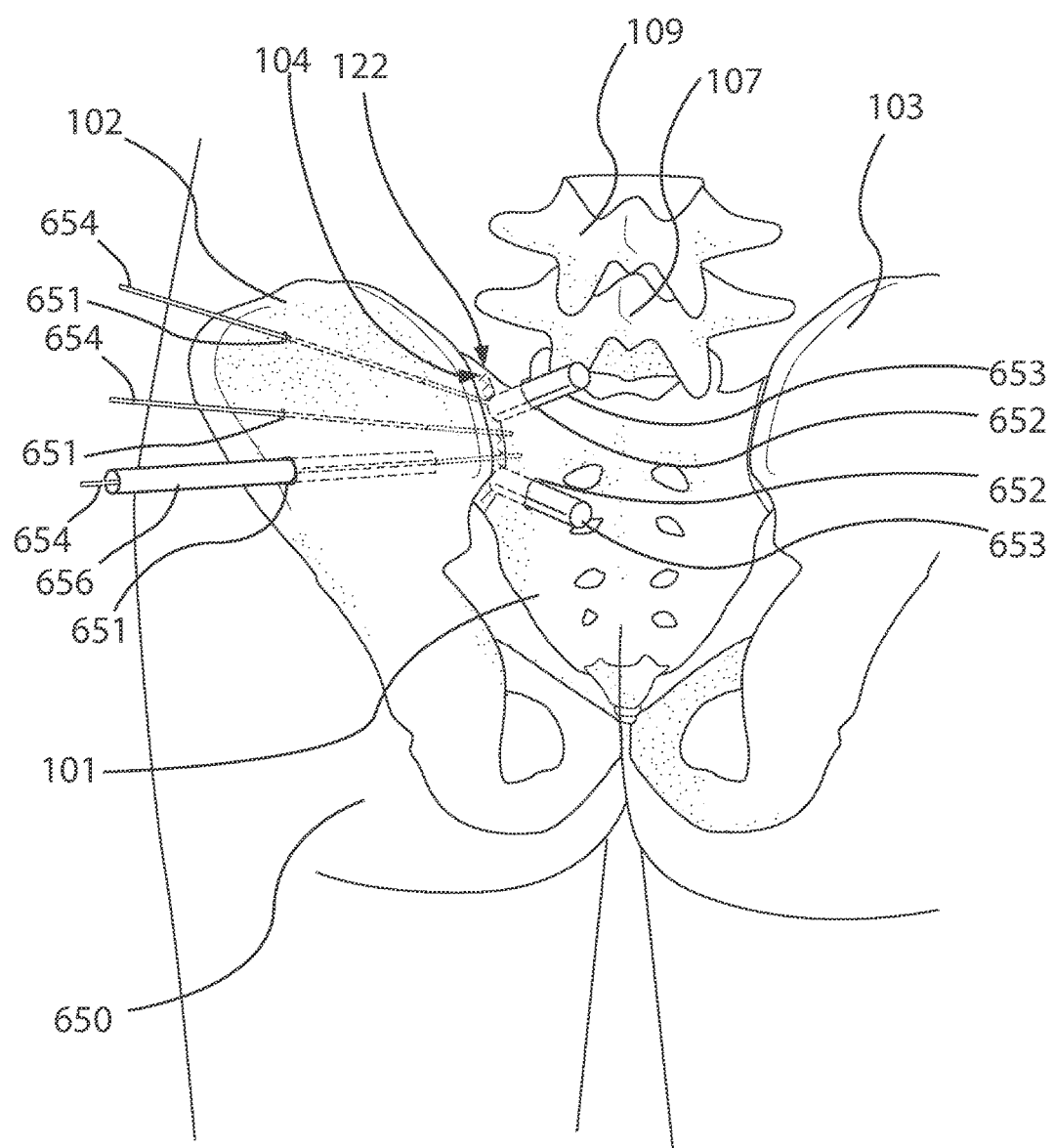
FIG. 8A. A posterior view of a patient's pelvis showing access portals following oblique paths towards the left SI joint, and guide wires following a stabilizer device path in an embodiment where the patient's skin and ilium are transparently represented to show the path of a guide wire and access portal.
Figures 8, 8B:
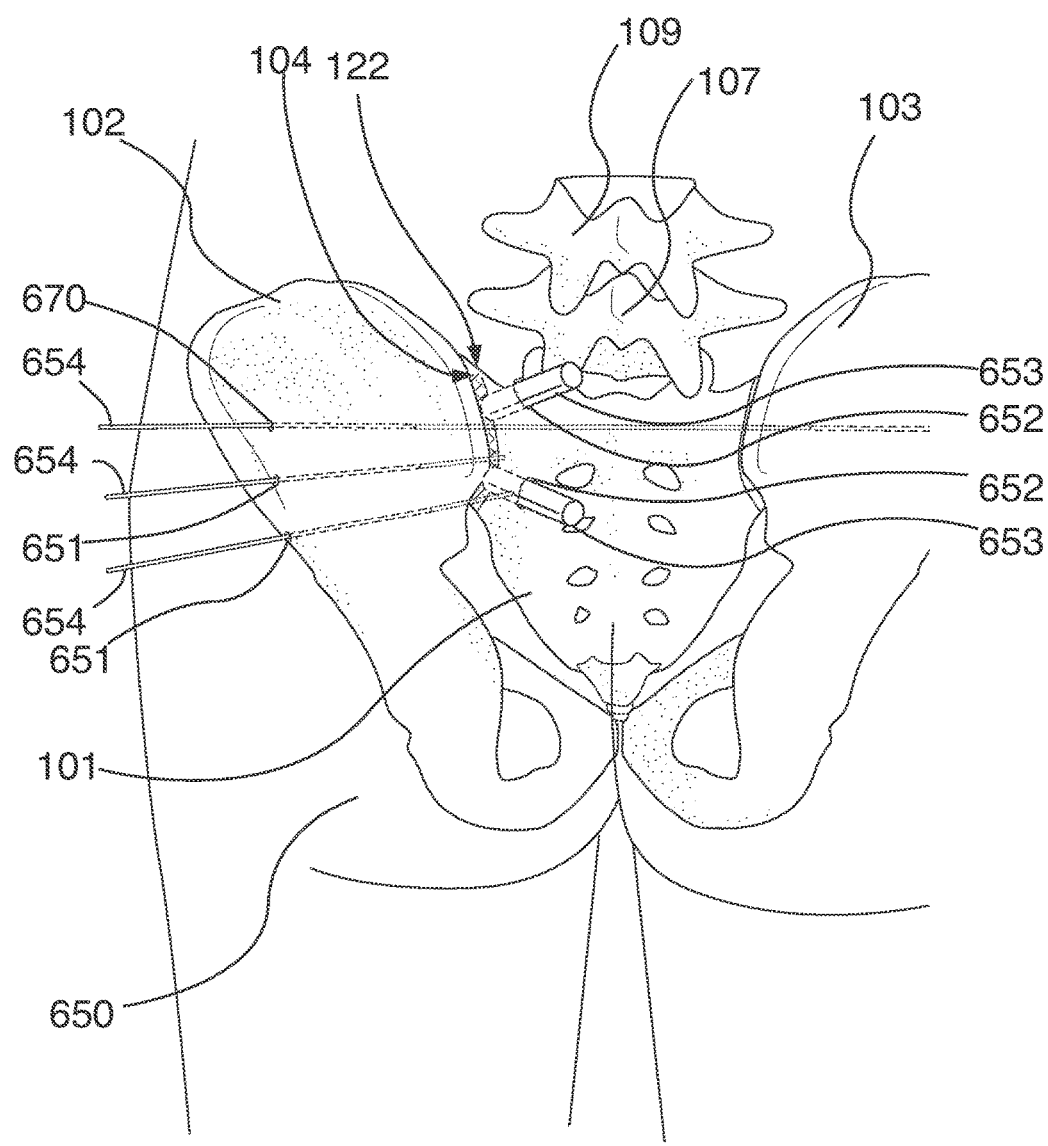
FIG. 8B. A posterior view of a patient's pelvis showing access portals following oblique paths towards the left SI joint, and guide wires following a stabilizer device path and a guide wire following a bilateral device path in an embodiment where the patient's skin and ilium are transparently represented to show the path of a guide wire and access portal.

Once a portion of a piercing tool reaches the sacrum through a stabilizer device path 701, in certain embodiments, during the insert guide wire step 209, as shown in FIG. 2A, a guide wire is inserted through a trephine needle. A trephine needle such as a Jamshidi® needle, typically has an opening, in which instruments with a smaller diameter may fit through. In one use case, a guide wire is used as a placeholder, where larger medical instruments can access the surgical site by following such guide wire, ensuring that such larger medical instruments do not stray from a distinct path; a potential benefit of using a guide wire is that potential damage to nerves, organs, and other regions of the body may be reduced by following the guide wire. During the insert guide wire step 209, a guide wire is fed through a trephine needle, and subsequently, the trephine needle is removed leaving a guide wire in place. For example, as shown in FIG. 8A, a guide wire 654 is placed through an incision 651, through an SI joint 104, and into a sacral ala 122. Such action effectively establishes a path from an exterior portion of a patient's body to an end point within the sacrum, such path occupied by a guide wire.

During the repeat stabilizer step 210, shown in FIG. 2A, a medical practitioner further creates another stabilizer device path 701 to effectively repeat the determine stabilizer device paths 201 step, which, in certain embodiments, include, but is not limited to sub-steps 204, 205, 206, 207, 208, and 209. In certain embodiments, one stabilizer device path 701 is established per SI joint. In certain embodiments of the invention, one, two, three, four, five, or six stabilizer device paths 701 are established per SI joint. It will be appreciated that the number of stabilizer device paths established during certain embodiments of the invention depends on several variables, such variables include but is not limited to, for example, the size of a stabilizer device, the anatomical structure of a patient, or the presence of a bilateral device.

Steps Associated with Establishing Decortication Paths

In certain embodiments, a determine decortication paths step 202, shown in FIG. 2A, allows effective decortication of an SI joint such that the articular surfaces of the sacrum and ilium are prepared for bone fusion. In one aspect of certain embodiments of the invention, one or a plurality of stabilizer devices mechanically secures an ilium and sacrum. In another aspect of certain embodiments of the invention, graft material biologically fuses an ilium and a sacrum. In certain embodiments, the combination of approaching an SI joint from both a stabilizer device approach 301 and a decortication approach 303, as shown in FIG. 3A, is advantageous for stabilizing the SI joint of a patient using bone graft material. In certain embodiments, the determine decortication paths step 202 is intended to access an SI joint through a decortication approach 303, as shown in FIG. 3A. In certain embodiments, as shown in FIG. 4A and FIG. 4B, one or more oblique paths 703 are created to an SI joint.

Referring to a flow diagram in FIG. 2A, the determine decortication paths step 202 includes but is not limited to a number of sub-steps, such as 1) determine approach angle step 211; 2) skin incision step 212; 3) insert guide wire step 213; 4) expand path to joint with dilators step 214; 5) deliver access portal step 215; 6) expand joint space step 216; 7) decortication step 217; 8) obtain graft material step 218; 9) pack graft material step 219; and 10) repeat fusion approach step 220. However, embodiments of the invention are not limited to these sub-steps, as such sub-steps are meant to be exemplary rather than limiting. It will be appreciated that certain steps, procedures, techniques, and/or instruments related to step 202 have similarities with the determine decortication paths step 253 shown in FIG. 2B, including sub-steps such as 1) determine approach angle step 271; 2) skin incision step 272; 3) insert guide wire step 273; 4) expand path to joint with dilators step 274; 5) deliver access portal step 275; 6) expand joint space step 276; 7) decortication step 277; 8) obtain graft material step 278; 9) pack graft material step 279; and 10) repeat fusion approach step 280.

Figure 2B:
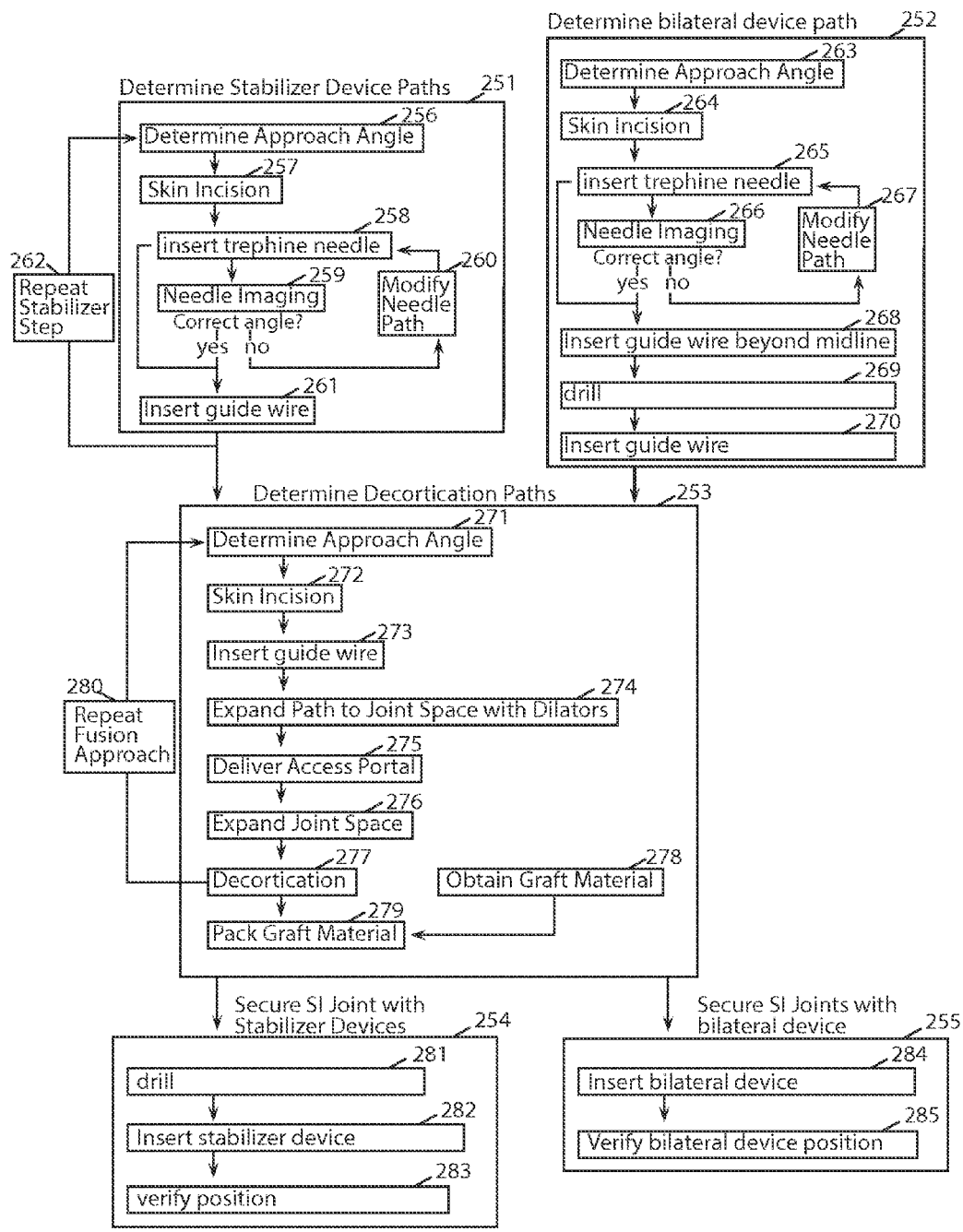
FIG. 2B. Flow diagram of the general procedure for a transsacral bilateral sacroiliac fusion approach associated with certain embodiments of the invention.

In certain embodiments of the invention, a determine decortication paths step 202, 253, shown in FIG. 2A, and FIG. 2B allows one to establish one or more oblique paths 703 to access an SI joint. In certain embodiments, one or more oblique paths 703 are established to an SI joint, as illustrated in FIG. 4A, FIG. 4B, FIG. 7A, FIG. 7B, FIG. 18A, and FIG. 18B. In embodiments of the invention, one or more oblique paths 703 may be established per SI joint. An oblique path 703, in general, follows an angle shown by a decortication approach 303 in FIG. 3A. Referring to FIG. 4B, a plurality of oblique paths 703 are in general, convergent towards an SI joint 104 in certain embodiments. By following more than one distinct path, certain areas of an SI joint 104 may be decorticated. In certain embodiments, oblique paths 703 may be substantially parallel or non-parallel, depending on, the anatomical structure of a patient or accessibility of such SI joint.

Figure 7A:
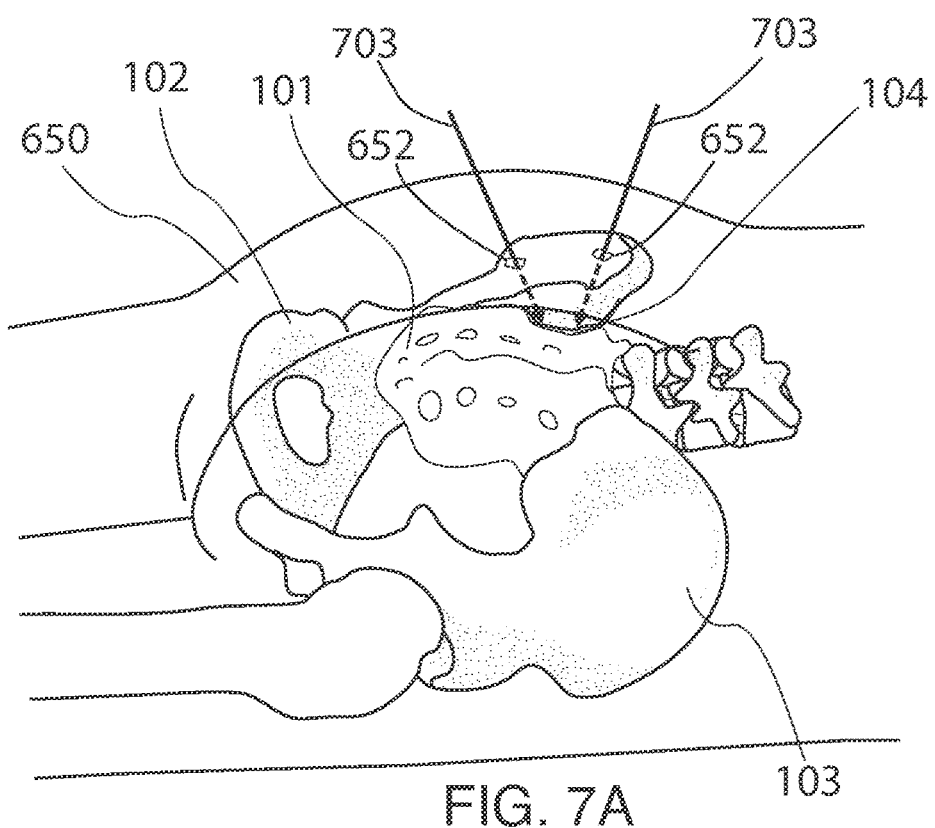
FIG. 7A. An oblique view showing oblique paths towards the left SI joint in an embodiment, where a patient's skin is transparently represented.
Figure 7B:
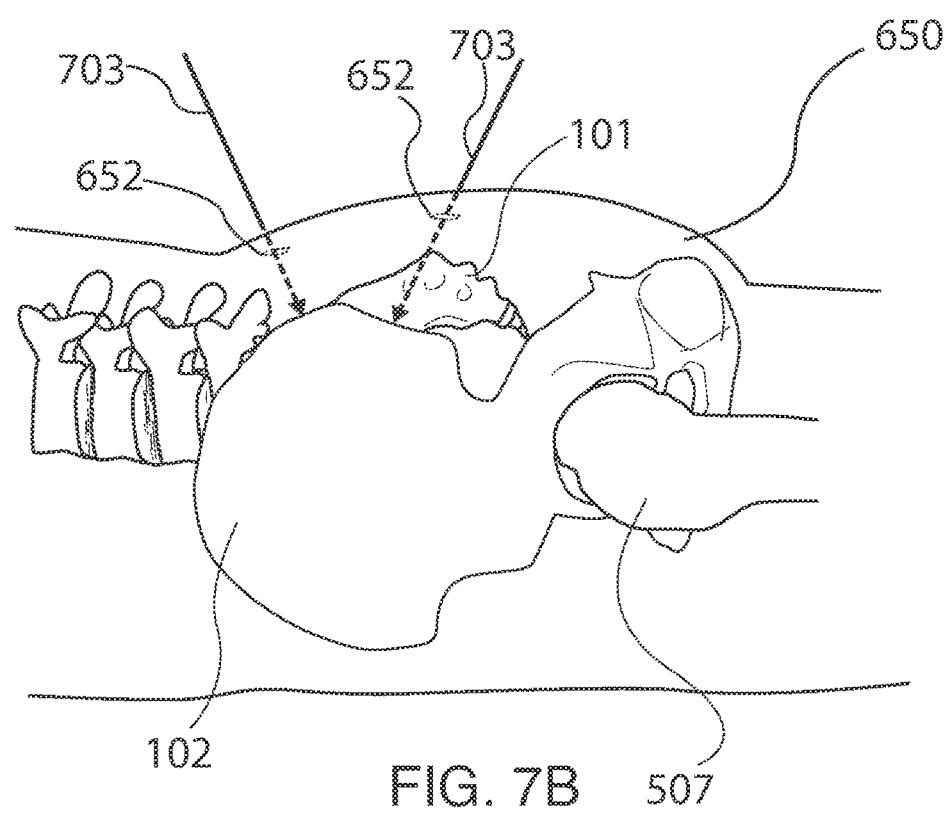
FIG. 7B. A lateral view showing oblique paths towards the left SI joint in an embodiment, where a patient's skin is transparently represented.
Figure 19A:
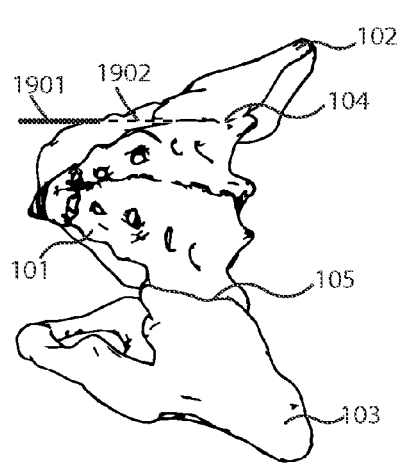
FIG. 19A. An oblique view of a pelvis showing a needle used to predict and determine an oblique path, in certain embodiments.
Figure 19B:
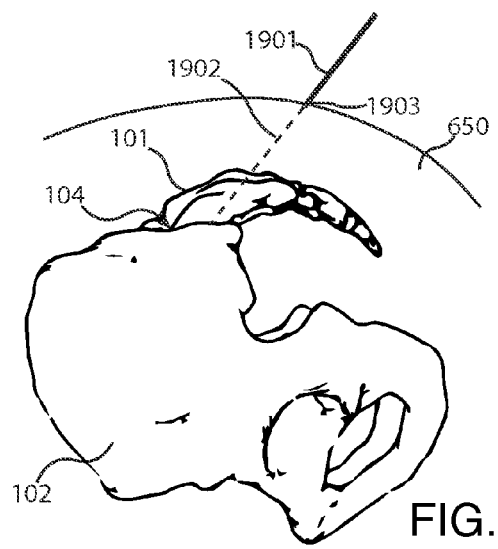
FIG. 19B. A lateral view of a pelvis showing a needle used to predict and determine an oblique path, in certain embodiments.

During the determine approach angle step 211, 271 shown in FIG. 2A, FIG. 2B, a medical practitioner adjusts the approach angle and/or potential incision site of a needle such that the angle of entry of such needle is at an angle similar to a decortication approach 303 shown in FIG. 3A. In certain embodiments, an initial entry point of a needle is empirically determined. For instance, a patient's pelvic region in an oblique view and/or the lateral view are referenced during step 211, 271; by referencing those views, it allows determining an approach angle that enters the SI joint that is generally parallel to a plane of an SI joint. For example, for a left SI joint 104, an imaging device is used to capture an oblique view of the pelvis as represented in FIG. 7A and FIG. 19A, and/or a lateral view of the pelvis as represented in FIG. 7B and FIG. 19B. It will be appreciated that certain steps can be performed for a right SI joint 105. In certain embodiments, a needle having a radio-dense property is used as a reference—a needle is adjusted and its position is verified by referencing oblique view and/or lateral-view images taken by an imaging device. It will also be appreciated that a needle, may also be used to refer to an oblong instrument having a radio-dense property. In one example, a medical practitioner references an oblique view, as exemplified in FIG. 19A, where such oblique view is generally in a plane that is parallel to an SI joint (e.g. left SI joint 104). In another example, a medical practitioner references a lateral view, as exemplified in FIG. 19B. A number of radiographic images may be taken and referenced until a needle 1901, being radio-dense, is oriented to align with a left SI joint 104. In certain embodiments, a hypothetical straight line 1902 extrapolated from a needle 1901 is extended to the SI joint 104, as shown in FIG. 19A and FIG. 19B. If such line 1902 allows entry into an SI joint, such path is used, and considered to be a path 703. An end 1903 of a needle 1901 is used to mark the surface of the skin (e.g. buttocks 650) as the location of an incision.

In certain embodiments of the invention, a skin incision step 212, 272 shown in FIG. 2A and FIG. 2B is performed after the determine approach angle step 211, 271. In general, a skin incision step 212, 272 creates the initial incision 652 for the oblique paths 703, as shown in example FIG. 7A, where such incision 652 is approximately the size of the instruments utilized during the sacroiliac fusion approach. In one example, an incision 652 is between 0.5 cm to 2 cm on the patient's buttocks 650, in another example, an incision 652 is 1 cm to 5 cm on the patient's buttocks 650, but other sizes smaller or larger may be appropriate. In general, the size of such incision to create the incision 652 is matched to the size of the instruments utilized during the determine decortication paths steps 202, 253 (shown for example in FIG. 2A and FIG. 2B) as to minimize the size of such incision and/or minimize the invasiveness of such sacroiliac fusion approach. Due to the relatively thin tissue layer of the area at and surrounding the oblique paths, a SI joint may be visualized from the exterior of the patient's body by inserting an endoscope through the oblique paths, or visually inspecting (i.e. direct visualization) the SI joint by further increasing the size of an incision 652 and subsequently expanding the skin with appropriate instruments, for example, tissue retractors. In some cases, inspection of an SI joint may be beneficial, for example, as to follow comply with Centers for Medicare and Medicaid Services (CMS) guidelines or insurance guidelines associated with policies for approval and reimbursement. The preferred embodiment of the sacroiliac fusion approach in general, is performed in a minimally invasive manner by referencing radiographic images using bone-scanning or imaging devices. In this manner, in an embodiment, the medical practitioner may place the stabilizer devices percutaneously without necessitating the exposure of the bone to the exterior.

Figure 19C:
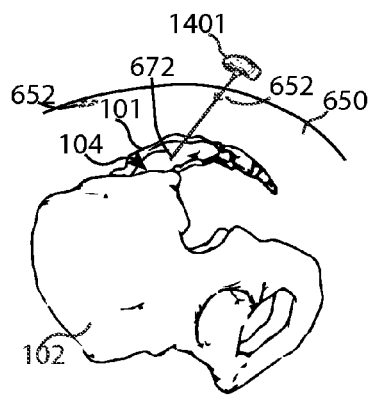
FIG. 19C. A lateral view of a pelvis showing a trephine needle used to access an SI joint through an oblique path, in certain embodiments.
Figure 19D:
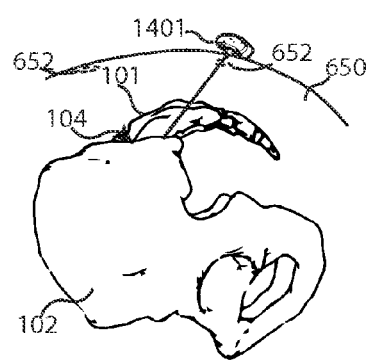
FIG. 19D. A lateral view of a pelvis showing a trephine needle further inserted into an SI joint through an oblique path, in certain embodiments.
Figure 19E:
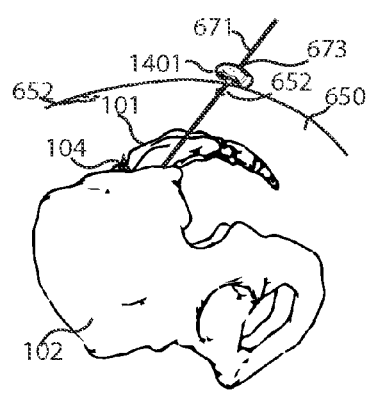
FIG. 19E. A lateral view of a pelvis showing a guide wire further inserted into a trephine needle in certain embodiments.
Figure 19F:
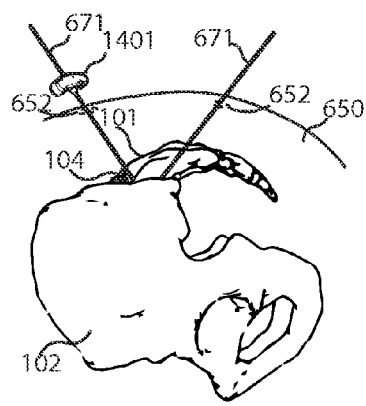
FIG. 19F. A lateral view of a pelvis showing a first guide wire inserted through an oblique path, and a second path being prepared, in certain embodiments.

In certain embodiments, radiographic images in an oblique view, for example, in FIG. 7A, or a lateral view, for example, in FIG. 7B, are referenced to advance a guide wire through the buttocks tissue to reach an SI joint during the insert guide wire step 213, 273, shown in FIG. 2A, FIG. 2B. The guide wire may establish an initial pathway for each oblique path 703 from the exterior of the body to the SI joint 104. While performing certain embodiments of an insert guide wire step 213, 273, as shown in FIG. 2A, FIG. 2B, radiographic images in an oblique view as exemplified in FIG. 19A, and a lateral view as exemplified in FIG. 19B are referenced to advance a guide wire through the buttocks tissue to reach the SI joint. In certain embodiments, a guide wire 671 establishes a physical path from the exterior of the body to the left SI joint 104 or right SI joint 105. In certain embodiments of an insert guide wire step 213, 273, a trephine needle 1401 is placed through an incision 652, as shown in FIG. 19C, and further tapped into an SI joint 104, as shown in FIG. 19D. Once a tip 672 of such trephine needle 1401 is tapped into an SI joint 104, as shown in FIG. 19D, a guide wire 671 may be placed through an opening 673 of a trephine needle 1401, until the tip of such guide wire reaches such SI joint, as shown in FIG. 19E. A trephine needle is then removed, leaving a guide wire, as shown in FIG. 19F. It will be appreciated that more than one path 703 to an SI joint may be established, where such paths are established during a repeat fusion approach 220, 280 as shown in FIG. 2A and FIG. 2B. As represented in FIG. 19F, one or more guide wires 671 may be used to access an SI joint with an oblique path 703.

This pathway is further expanded in diameter using a series of dilators. Typical dilators have an opening that allows such dilator to slide over a guide wire or other dilators, so that so as to expand an opening of the stabilizer device paths 701, bilateral device paths 702, and/or oblique paths 703. In certain embodiments, using successively larger dilators through the stabilizer device paths 701, bilateral device paths 702, and/or oblique paths 703 stretches tissue surrounding a guide wire, and allows larger instruments, devices, or materials to enter. For instance, in certain embodiments, a series of successively larger dilators have diameters that are 2.5 mm, 4.5 mm, 6.5 mm, and 10 mm, but it will be appreciated that dilators are not restricted to these sizes. It will be appreciated that the number of dilators used during the expand path step 214, 274 shown in FIG. 2A and FIG. 2B can vary between two to five or more. In certain embodiments, a size of the oblique paths 703 is expanded to 10 mm in diameter, or more, (for example, 11 mm, 12 mm, 13 mm, 14 mm, 15 mm, 16 mm, 17 mm, etc) so as to expand the SI joint and allow entry of appropriate medical instruments used during the expand joint space step 216, 276, decortication step 217, 277, and pack graft material step 219, 279 (as shown for example in FIG. 2A and FIG. 2B). However, it will be appreciated that the size of an oblique path is not restricted to 10 mm, as other sizes, such as less than, or greater than 8 mm, 9 mm, 10 mm, 11 mm, 12 mm, 13 mm, and 14 mm may be used in embodiments of the invention.

During a deliver access portal step 215, 275, shown in FIG. 2A, FIG. 2B, one or more paths from the exterior of the patient's body to the SI joint are established. An access portal may refer to a dilator, or a cannulated tube, or similar device. In certain embodiments, an access portal may have surface features that provide traction on or between bone structures. In one example, an access portal embodiment may be tapped (i.e. struck) by a blunt instrument as to fit within an SI joint. In certain embodiments, an access portal 653 allows stable placement of an accessible path from an exterior of a body to a SI joint, as shown in FIG. 8A. An access portal 653 may be tapped in, such that a distal end of an access portal 653 is secured, by compression of the access portal 653 between a left sacral ala 122 and a left ilium 102, as exemplified in FIG. 8A. In general, an access portal allows guiding, maneuvering, or otherwise utilizing medical instruments (for example, disc cutters, etc) during the expand joint space step 216, 276, decortication step 217, 277, and pack graft material step 219, 279. In certain embodiments of the invention, tissue, muscle, bone, and/or the SI joint is expanded with instruments, including, for example, specula and retractors through one or more paths 703.

Instruments typically related to the removal of material from joints are used to expand an SI joint and remove material (for example, cartilage, cortical bone, etc) found on articular surfaces of an ilium and sacrum. In certain embodiments, such instruments include, but are not limited to scalpels, chisels, curettes, retractors, dissectors, choppers, rasps, knives, probes, burrs, rongeurs, forceps, separators, endoscopes, disc cutters. During the expand joint space step 216, 276 and the decortication step 217, 277, shown in FIG. 2A, FIG. 2B, an SI joint space is expanded, and fibrocartilage and hyaline cartilage located in the SI joint are removed. In certain embodiments, portions of cortical bone, such as an outer layer, or an ilium and sacrum are scraped and bled. The effective removal of cartilage, and bleeding of cortical layer of bone are important, as such techniques further promote bone fusion. Such steps are preferably performed prior to the pack graft material 219, 279 step, as shown in FIG. 2A and FIG. 2B. In certain embodiments, a guide wire that generally takes a path 302 and 301 is kept within an SI joint 104 (after completing step 209, 261, or 270, as shown in FIG. 2A and FIG. 2B), therefore, surfaces of an SI joint may be prepared by working around such guide wire. In other embodiments of the invention, a guide wire may be partially pulled out of the SI joint space by the medical practitioner prior to or during decortication.

During a pack graft material step 219, 279, shown in FIG. 2A and FIG. 2B, graft material is placed into an SI joint. In certain embodiments, graft material, as referred to herein, refers to morselized autograft or allograft bone matter, and may also include other substances biological or chemical that help in bone fusion, including, but not limited to bone marrow, plasma, calcium phosphates, xeongraft bone, bone cement, human growth factors. In certain embodiments, graft material may be acquired during the graft material preparation step 218, 278, as shown in FIG. 2A and FIG. 2B. In an embodiment of the invention, autograft material is obtained from a patient during the determine decortication paths step 202, 253 shown in FIG. 2A, FIG. 2B by scraping bone material from articular surfaces associated with an SI joint, or during the secure SI joint with stabilizer device step 203, 254, or from other parts of the patient's body such as the iliac crest. It will be appreciated that in certain embodiments, any number of autograft bone sources may be used, by acquiring such bone from any number of methods known to those skilled in the art. During step 218, 278, bone is further prepared, for example, by grinding or morselization of such bone. In certain embodiments of the pack graft material step 219, 279, shown in FIG. 2A, FIG. 2B, graft material is filled within an SI joint space to allow the graft material to fuse iliac and sacral bone surfaces. In certain embodiments, graft material is pushed through an access portal into the SI joint space. In certain embodiments, an implant in combination with graft material may be inserted into an SI joint while performing step 219, 279.

During the repeat fusion approach step 220, 280 shown in FIG. 2A and FIG. 2B, more than one oblique path 703, as shown in FIG. 4B, FIG. 18A, and FIG. 18B, may be established. In certain embodiments, more than one oblique path 703 could be advantages, as to better access surfaces of an SI joint and further decorticate such surfaces. In certain embodiments of the invention, a plurality of oblique paths 703 is established concurrently, so as to decorticate the articular surfaces of the ilium and sacrum from a plurality of angles using a plurality of access portals 653 as shown in FIG. 8A.

Steps Associated with Securing an SI Joint with a Stabilizer Device

In certain embodiments, a secure SI joint with stabilizer device step 203 shown in FIG. 2A includes steps to secure one or more stabilizer devices through an ilium and sacrum. In certain embodiments, a stabilizer device mechanically secures the two bones. Graft material placed within an SI joint during step 202, shown in FIG. 2A, additionally allows fusion of the articular surfaces of the ilium and sacrum. In certain embodiments, a secure SI joint with stabilizer device step 203 includes, but is not limited to the following sub-steps: 1) drill step 221; 2) Insert stabilizer device step 222; and 3) verify position step 223. It will be appreciated that the procedure, methods, instruments, techniques used in step 203 may also be used for step 254 shown in FIG. 2B to perform certain embodiments of a transsacral bilateral sacroiliac fusion approach, where such step 254 include, but is not limited to the following sub-steps: 1) drill step 281; 2) insert stabilizer device step 282; and 3) verify position step 283.

Figure 9:
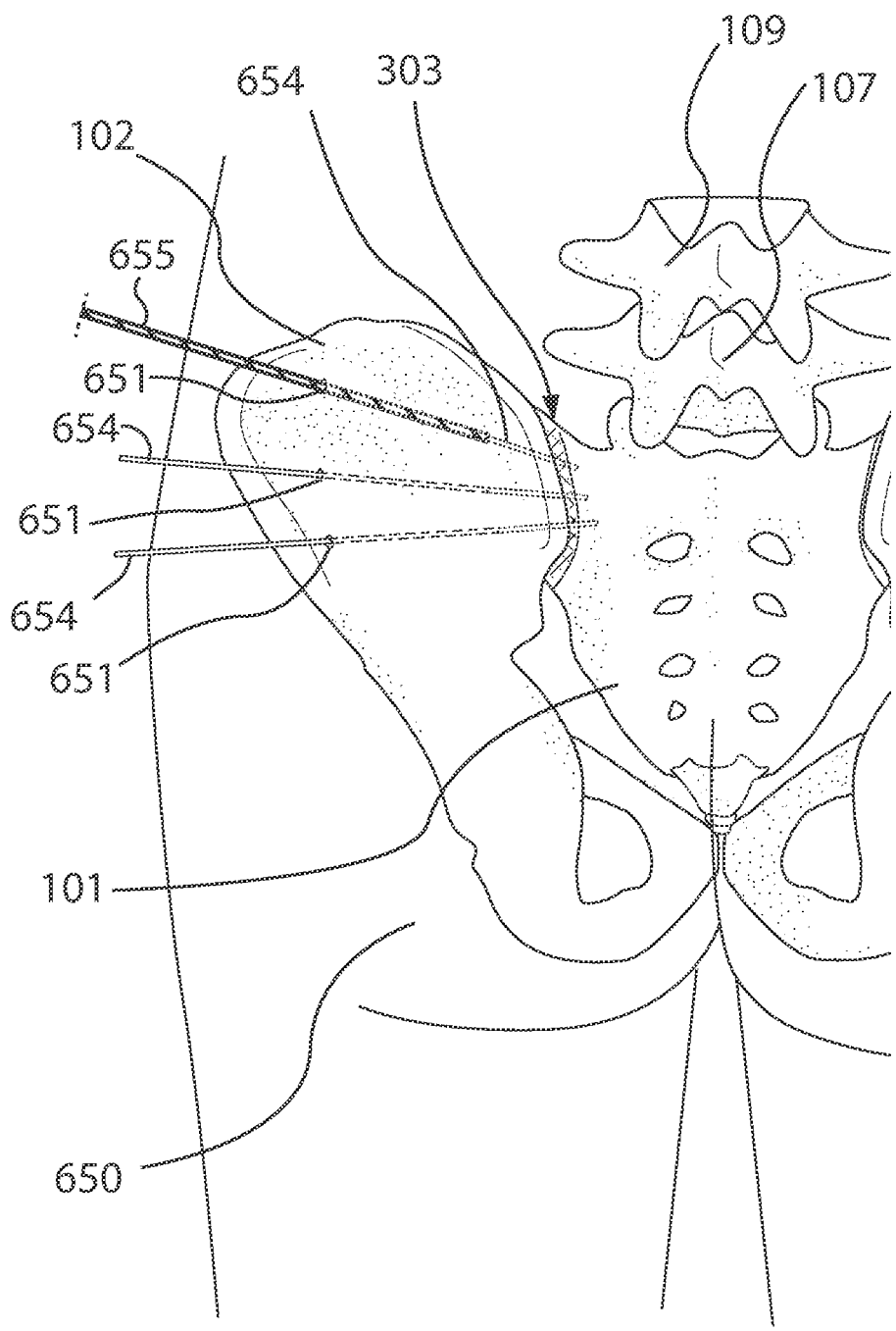
FIG. 9. A posterior view of a patient's pelvis showing a drill following a guide wire in an embodiment of the invention.
Figure 20A:
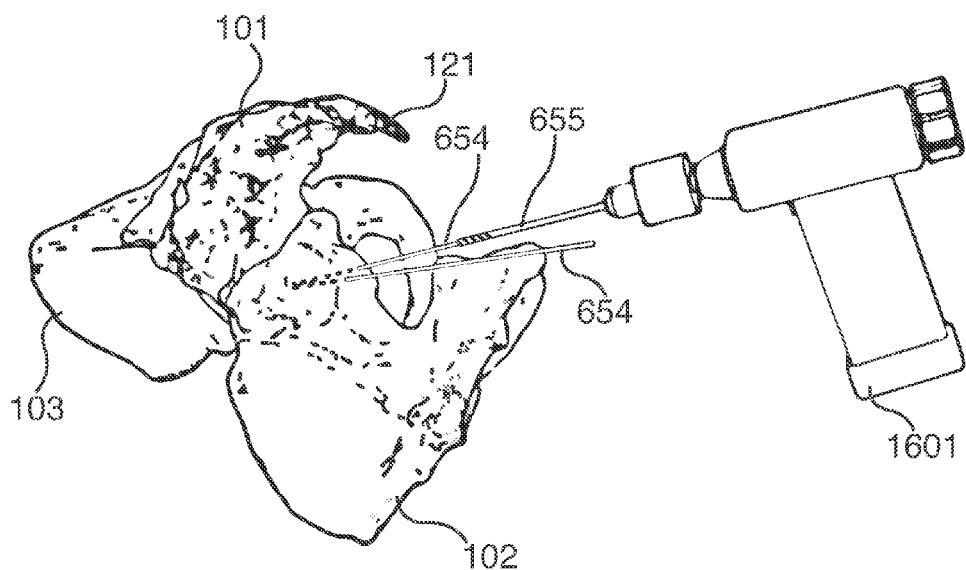
FIG. 20A. Representative perspective view of a pelvis, where a guide wire is inserted in a stabilizer device path, and a drill is used to follow a guide wire of a second stabilizer device path, further expanding the path, in certain embodiments.

During certain embodiments of the drill step 221, 281 shown in FIG. 2A, FIG. 2B a drill bit is placed over a guide wire, where a guide wire was established during an insert guide wire step 209, 261. In certain embodiments, a dilator 656 may be placed over a guide wire 654, as shown in FIG. 8A as to create a pathway to the ilium. In certain embodiments, a drill bit with an opening along its longitudinal axis that allows placement of such drill over a guide wire is used. In certain embodiments, a drill bit is between 1.5 and 4 mm in diameter, with an opening extending the length of such drill bit to accommodate the diameter of a guide wire 654. It will be appreciated that certain embodiments of the invention may utilize a drill bit that is between 0.5 mm and 10 mm in diameter, or other sizes smaller or larger. As shown in an example in FIG. 9, a drill bit 655 follows a path of the guide wire 654 to drill through an ilium 102, through an SI joint, and into the sacral ala 122, and as further shown in FIG. 20A. During the drill step 221, 281, an imaging device capturing a lateral view and/or the oblique view is used. By using these views, it ensures that a drill bit 655 does not surpass the anterior edge of the sacrum 101, thereby ensuring that such drill does not enter the peritoneum of the patient and avoiding nerves and tissue located anterior to the sacrum.

Figure 10A:
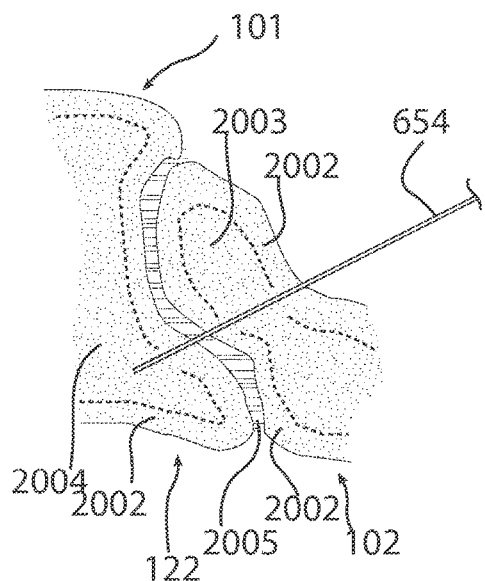
FIG. 10A. A guide wire across a portion of a sacrum, left ilium, and left SI joint, in a cross sectional superior-inferior view.
Figure 10B:
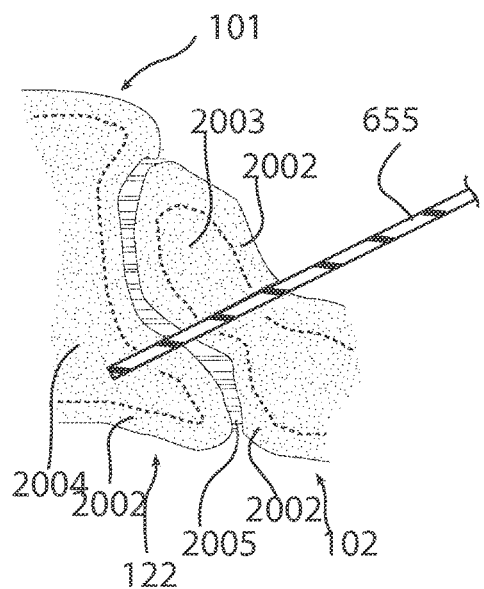
FIG. 10B. A drill bit across a portion of a sacrum, left ilium, and left SI joint, in a cross sectional superior-inferior view.
Figure 10C:
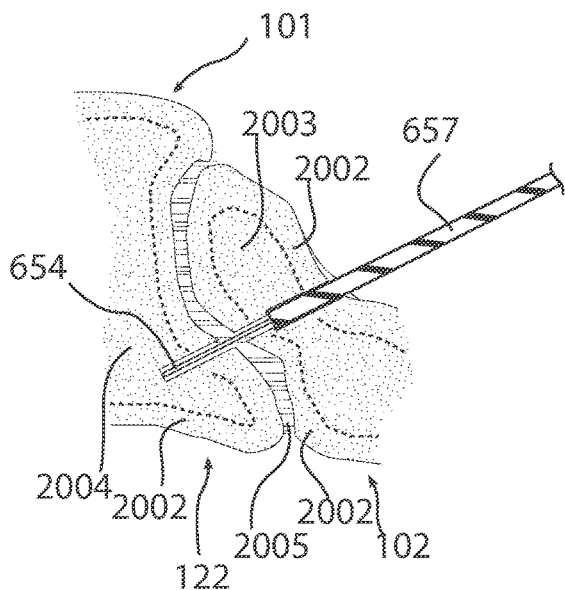
FIG. 10C. A drill bit across a portion of a left ilium, in a cross sectional superior-inferior view.
Figure 10D:
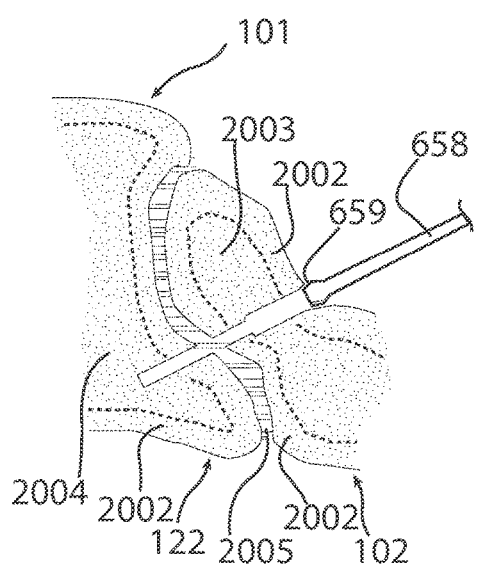
FIG. 10D. A step drill across a portion of a left ilium, in a cross sectional superior-inferior view.

In certain embodiments, more than one drill bit may be used during a drill step 221, 281 shown in FIG. 2A, FIG. 2B. For instance, as illustrated in the cross-sectional view of a left SI joint and surrounding bone in FIG. 10A, FIG. 10B, FIG. 10C, and FIG. 10D, a drill 655 shown in FIG. 10B enlarges the diameter of a stabilizer device path by drilling over the previously established guide wire 654 shown in FIG. 10A. Furthermore, a drill 657 having a larger diameter, as shown in an example in FIG. 10C, may be used to further expand the diameter of the stabilizer device path or certain sections of the stabilizer device path, such as for example, specifically through iliac bone 102. In certain embodiments of the invention, a drill step 221, 281 shown in FIG. 2A, FIG. 2B may use other drills having a larger diameter, and/or tips having various shapes. For instance, as illustrated in FIG. 10D, an embodiment of a step drill 658 may have an edge 659 that further expands an opening. In certain embodiments, such opening may accommodate a lip 2202 of a sheath 2201, as shown for example in FIG. 20C and FIG. 22D.

A drill 655, 657, or step drill 658 are intended to provide examples of certain embodiments to drill an opening through an ilium and the sacrum such as to secure an ilium and sacrum with a stabilizer device and/or sheath. In embodiments of the invention, the drill step 221, 281 shown in FIG. 2A, FIG. 2B, may include other drilling devices known to those having skill in the art. In embodiments of the invention, a stabilizer device 2101 is used to secure an ilium and the sacrum as well as to drill such stabilizer device through the stabilizer device path. However, in general, the purpose of the drill step 221, 281 is to create a path so that the stabilizer device and/or sheath is placed within a stabilizer device path.

Figure 20B:
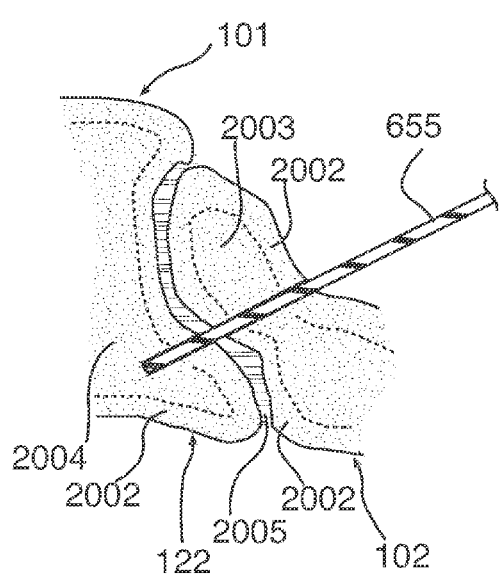
FIG. 20B. An illustration of a drill through a left sacrum, left ilium, and left SI Joint, in a cross sectional superior-inferior view of an SI joint, in an embodiment of the invention.
Figure 20C:
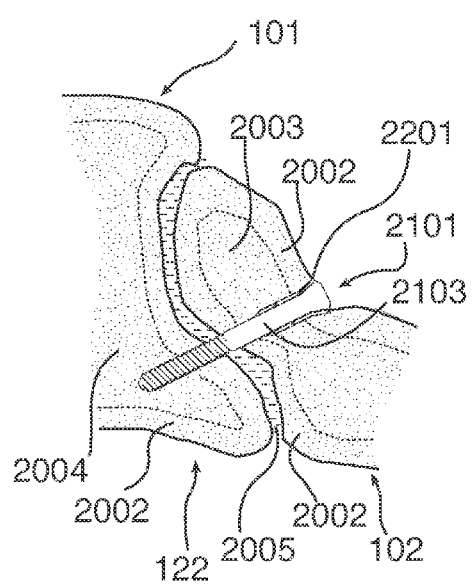
FIG. 20C. A cross sectional view of the left sacrum, left ilium, and left SI Joint from the superior-inferior view with an embodiment of a stabilizer device and sheath used to secure the SI joint.

Following the drill step 221, 281 as shown in FIG. 2A, FIG. 2B, a medical practitioner proceeds with the insert stabilizer device step 222, 282. During the insert stabilizer device step 222, 282, one or more stabilizer devices and/or the sheaths are inserted along a stabilizer device paths previously established during the determine stabilizer device paths step 201, or 251. Examples of certain embodiments of a stabilizer device are disclosed herein. In one embodiment, a stabilizer device 2101 referred to in FIG. 21A and FIG. 21B comprises a central opening 2105, where a medical practitioner guides a stabilizer path to the ilium by passing the stabilizer device over a guide wire. In certain embodiments of the invention, a sheath 2201, as shown for example in FIG. 22A, FIG. 22B, FIG. 22C, and FIG. 22D is guided over a guide wire 654, and tamps such sheath 2201 into an opening of the iliac bone 102, as referenced in FIG. 20C. A stabilizer device 2101 is further placed within the opening by following the path of the guide wire 654, as shown in FIG. 20C. In certain embodiments, a driver may be used to secure such stabilizer device. A driver, for instance, is a tool that has a structure with a fit to a drive located on a head 2104 of a stabilizer device 2101, such that turning of a driver engaged to stabilizer device head allows such stabilizer device to enter bone. In one embodiment of the invention, axial rotation of a stabilizer device 2101 advances such stabilizer device through a hole opened by a drill 655 shown for example in FIG. 20B, and FIG. 20C. In various embodiments of the invention, a driver and the corresponding head 2104 of a stabilizer device 2101 has a structure and indentation respectively, that are known to those skilled in the art, including but not limited to for example, square, cross, Philips, Hex, and TTAP. In other embodiments of the invention, such structure and indentation are unique to the stabilizer device as disclosed herein.

Figure 21A:
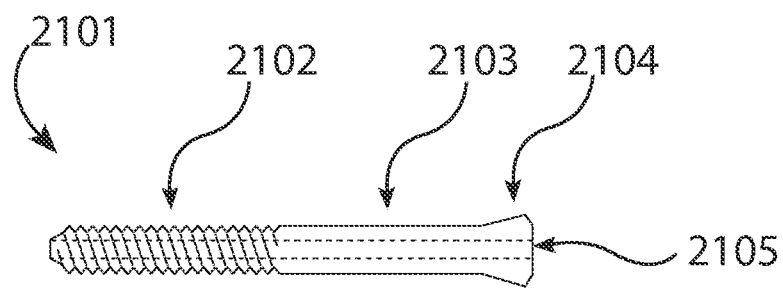
FIG. 21A. A side view of an embodiment of a stabilizer device.
Figure 21B:
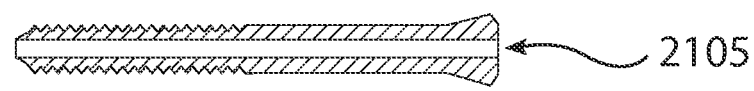
FIG. 21B. A side, cross-sectional view of an embodiment of a stabilizer device.

The inventor has discovered a number of benefits to the design of certain embodiments of a stabilizer device as described. Referring to FIG. 21A, a shank 2103 of the stabilizer device 2101 (a shank may also referred to as a lag) is 20 mm in length in certain embodiments. In other certain embodiments, a shank 2103 is between 15 and 25 mm in length but may be shorter or longer than such lengths. The length of the shank 2103 is, in general, approximately the typical thickness of the iliac bone found in the area that the sacroiliac fusion approach is performed. Various embodiments of the thread 2102 of the stabilizer device 2101 feature a length that is between 20 mm and 60 mm. The length of the thread 2102 corresponds approximately to the thickness of the cortical bone of the sacral ala, or greater than its thickness, where embodiments of the sacroiliac fusion approach is performed. The inventor has discovered that, in certain embodiments, incorporating a shank region to the stabilizer device ensures that the sacral bone and iliac bone are compressed as the stabilizer device 2101 is driven into the sacral ala. Compression of the sacral bone and iliac bone enhances the stability of the SI joint after surgery. Moreover, the compression stabilizes the graft material between the sacral bone and iliac bone such that proper fusion of such bones takes place after surgery. Furthermore, referring to FIG. 22A, FIG. 22B, FIG. 22C, and FIG. 22D, embodiments of a sheath 2201 further enhances the stability of the stabilizer device within the iliac bone. Certain embodiments of a sheath, increases the stability of the stabilizer device by providing an increased surface area within the iliac bone as to provide increased stability of the stabilizer device within the iliac bone. Furthermore, the added integration of the graft material within the SI joint space further increases the stability of the SI joint after completing the surgical procedure and subsequent healing and recover.

Once a plurality of stabilizer devices are secured within each stabilizer device path 701 as in 222, 282, a medical practitioner proceeds with a verify position step 223, 283, as shown in FIG. 2A and FIG. 2B. By viewing a pelvic region with an oblique view and/or lateral view (although not limited to such views) using an imaging device, the position and/or placement of a stabilizer device is verified as to ensure that a stabilizer device is properly inserted in a sacrum, ilium, and SI joint during such step 223, 283. A medical practitioner may further correct a position of the stabilizer device and/or sheath if inconsistencies or errors are found in the position of the stabilizer device and/or sheath in an embodiment of the invention.

General procedures to close the incision previously created during the aforementioned steps are performed, in certain embodiment of the invention. Various incision-closing means are used during the sacroiliac fusion approach, including, for example, sutures, bandages, and staples. Preferably, because the incisions are smaller compared to prior art sacroiliac fusion procedures, the patient has minimal bleeding and decreased recovery time.

Advantages

In the case of a unilateral sacroiliac fusion approach, benefits of approaching an SI joint from two approach trajectories are many fold. Typical prior art procedures, such as that described in U.S. Pat. No. 8,734,462 B2, rely solely on the use of one general approach for the purposes of securing the ilium to the sacrum with, for example, screws, leading to a variety of suboptimal results. While a singular stabilizer device may be used in association with alternative embodiments of the inventive subject matter, certain embodiments of a unilateral sacroiliac fusion approach described here incorporates the use of one or more stabilizer devices. Using one or more stabilizer devices tightly secure the ilium and sacrum in certain embodiments. In certain embodiments, a medical practitioner may stabilize the ilium and the sacrum with bone fusion material. Bone fusion material, or graft material, may include morselized autograft or allograft bone matter that facilitates bone fusion. Bone fusion material may include one or more of other biological substances or chemical substances that aid in bone fusion, including, but not limited to bone marrow, plasma, calcium phosphate. In certain embodiments of the invention, a stabilizer device, is in general, an oblong shape for the purposes of securement of the sacrum 101 and the left ilium 102 by traversing the left SI joint 104, and/or for the securement of the sacrum 101 and the right ilium 103 by traversing the right SI joint 105.

Advantages of creating a relatively smaller incision includes decreased potential healing time and/or faster recovery of the skin. Furthermore, it will be appreciated that small incisions can decrease likelihood of complications associated with surgery, for example, reducing the chances of hematoma and/or bacterial infection of the area, or reducing the risks of slicing or damaging nerves and blood vessels associated with the buttocks. Additionally, the small incision further reduces the time for the general sacroiliac fusion approach procedure, as a smaller area of the buttocks is opened and sutured.

A Transsacral Bilateral Sacroiliac Fusion Approach
General Steps

The general procedure for a transsacral bilateral sacroiliac fusion approach associated with certain embodiments is illustrated in a flow diagram in FIG. 2B. A flow diagram represented in FIG. 2B is shown for demonstrative purposes as a general outline of such approach, and is meant to be exemplary rather than limiting. As represented in FIG. 2B, the transsacral bilateral sacroiliac fusion approach, in general, includes, but is not limited to the following steps: 1) determine stabilizer device paths 251; 2) determine bilateral device paths 252; 3) determine decortication paths 253; 4) secure SI joint with stabilizer devices 254; and 5) secure SI joint with bilateral device 255. However, it will be appreciated certain embodiments are not limited to such steps, and other steps useful to successfully perform a transsacral bilateral SI fusion may be used.

In general, certain embodiments of the invention involves entry into the pelvic space through three general approaches per each SI joint. These approaches, generally referred to as a "stabilizer device approach," a "bilateral device approach," and a "decortication approach," are distinguished by their general purpose and location of entry into the anatomical features within and near the pelvic region. A stabilizer device approach, bilateral device approach, and a decortication approach each further comprises a distinct path. Furthermore, a number of surgical devices known to persons having ordinary skill in the art related to spinal fusions, including, but not limited to syringes, trephine needles such as Jamshidi needles, cannulae, endoscopes, guide wires, drill, drills, dilators, tubes, curettes, etc are used for access and entry into the pelvic space through the approaches and paths found in certain embodiment of the invention. A variety of medical instruments may be used in association with certain embodiments of the transsacral bilateral sacroiliac fusion approach. However, preferably, certain embodiments of the invention use medical instruments that achieve minimally invasive sacroiliac fusion of one, or both the left SI joint and right SI joint.

Stabilizer Device Approach

Figures 3, 3B:
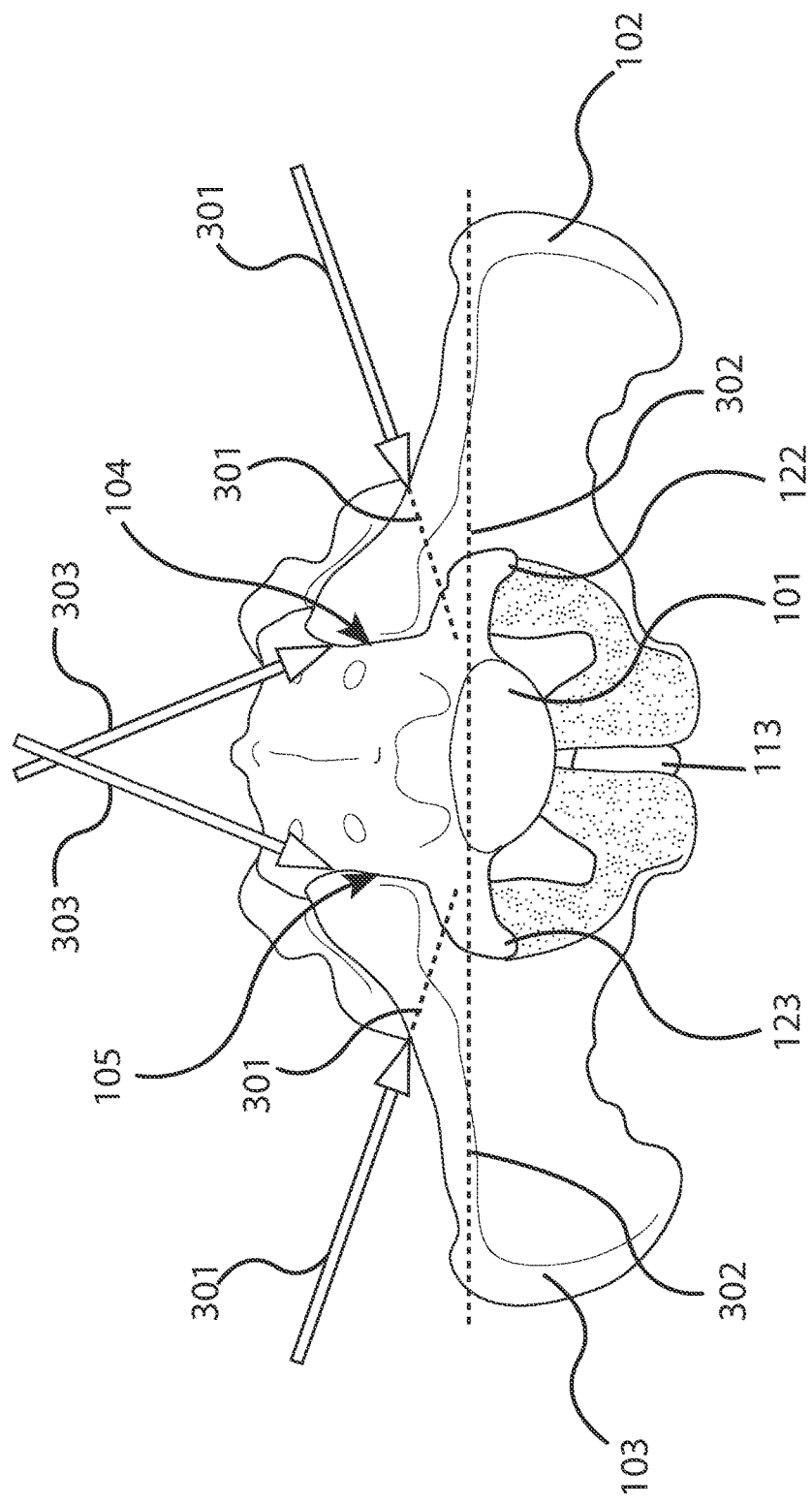
FIG. 3B. The stabilizer device approach, bilateral device approach, and decortication viewed from a superior-inferior angle of a pelvis in certain embodiments of the invention.

As illustrated in a representative example of the superior-inferior view of the pelvis in FIG. 3B, a stabilizer device approach 301 is at an angle that is generally lateral and posterior. Generally, in certain embodiments, a stabilizer device approach 301 is a general approach that traverses an ilium, traverses a SI joint, and enters the sacrum. In certain embodiments, the stabilizer device approach 301 further comprises a defined path, referred to as a stabilizer device path that allows compression and stabilization of the sacrum and an ilium. As illustrated in the posterior view of the hip in FIG. 4C, the left posterior-caudal perspective view of the hip in FIG. 5A, and the left posterior-rostral perspective view of the hip in FIG. 5B, a plurality of stabilizer device paths 701 are established during the certain embodiments of the transsacral bilateral sacroiliac fusion approach (as well as during embodiments of a sacroiliac fusion approach). medical practitioner establish the stabilizer device paths 701, in general, by medical processes related to separating, cutting, boring, drilling, and/or otherwise creating a passageway through bone and bone structures and surrounding tissue, muscle and other anatomic structures. Instruments that are related to create said passageway include, but are not limited to trephine needles such as Jamshidi needles, needles, drills, and drills. In the preferred embodiment of the invention, the stabilizer device paths 701 are established such that the left ilium 102 and/or the right ilium 103 are secured to the sacrum 101 using a plurality of stabilizer devices.

Bilateral Device Approach

Second, as further illustrated in the superior-inferior view of the hip in FIG. 3B, the bilateral device approach 302, in general, traverses through an ilium (for example ilium 103), through the sacrum 101, and through the other ilium (for example ilium 102). The angle of approach of the bilateral device approach 302 to the sacrum 101 and through both the left ilium 102 and right ilium 103, is in general, lateral, as shown in FIG. 3B. In certain embodiments, a bilateral device approach 302 comprises a path 702 passing laterally through those bones, as shown for example in, FIG. 5A, FIG. 5B, FIG. 8B, and FIG. 14A. Such path allows compression and stabilization of both ilia to the sacrum during certain embodiments of the transsacral bilateral sacroiliac fusion approach.

In certain embodiments of the invention, the bilateral device approach 302 further comprises a bilateral device path 702. As illustrated in the posterior view of the hip in FIG. 4C, the left posterior-caudal perspective view of the hip in FIG. 5A, and the left posterior-rostral perspective view of the hip in FIG. 5B, certain embodiments comprise a single bilateral device path 702 for a patient. However, other embodiments of the transsacral bilateral sacroiliac fusion approach may comprise more than one bilateral device path. A medical practitioner establishes a bilateral device path 702, in general, by medical processes related to piercing, puncturing, boring, drilling, and/or otherwise creating a passageway through bone and bone structures, and surrounding tissue, muscle and other anatomic structures. Instruments that are related to create said passageway include, but are not limited to trephine needles such as Jamshidi needles, cannulated needles, tubes, cannulated devices, drills, wire drills, and guide wires.

Decortication Approach

In certain embodiments, a decortication approach 303 advances towards the SI joint at an oblique angle, and at an angle that is in general more posterior than lateral, as illustrated in the superior-inferior view of the hip in FIG. 3B. In certain embodiments, the decortication approach 303 is an approach that allows access to and removal of SI joint material, for instance, cartilage, or portions of cortical bone, and through which a medical practitioner may add bone fusion material for bony fusion of the sacrum and ilium. The decortication approach 303 comprises an oblique path 703, shown in an example in FIG. 4A and FIG. 4B, where an oblique path 703 is a specific pathway to access an SI joint from the exterior of a patient's body. Therefore, preferably, the decortication approach 303 is in a plane that is, in general, parallel to the plane of the SI joint from the posterior-oblique direction of the patient. It will be appreciated that access to the SI joint through an oblique path 703 or a plurality of oblique paths, and using specific steps and/or types of medical instruments disclosed in certain embodiments of the invention, allows a medical practitioner to access one or more SI joint in a minimally invasive manner.

Steps Associated with Establishing Stabilizer Device Paths

As represented in FIG. 2B, in certain embodiments of a determine stabilizer device paths step 251, such step further includes a number of sub-steps, including, but not limited to: 1) determine approach angle step 256; 2) skin incision step 257; 3) insert trephine needle step 258; 4) needle imaging step 259; 5) modify needle path step 260; 6) insert guide wire step 261; and 7) repeat stabilizer step 262. However, other embodiments of the invention are not limited to these sub-steps or in a particular order, and said sub-steps are meant to be exemplary rather than limiting. In preparation for the steps shown in FIG. 2B, a patient may be placed under anesthesia, certain areas disinfected, and other standard procedures and practices related to surgery and/or spinal fusions known to persons having ordinary skill in the art. An imaging device used during certain embodiments of a transsacral bilateral sacroiliac fusion approach may capture images of a patient through a number of different views, including but not limited to the lateral view, oblique view, inlet view, and outlet view of the patient's pelvic region. In certain embodiments, an inlet view may refer to a view that originates from a generally rostral/cranial and posterior location to a generally caudal and anterior location. In certain embodiments, an outlet view may refer to a view that originates from a generally caudal/posterior location to a generally rostral/anterior location.

Figure 11A:
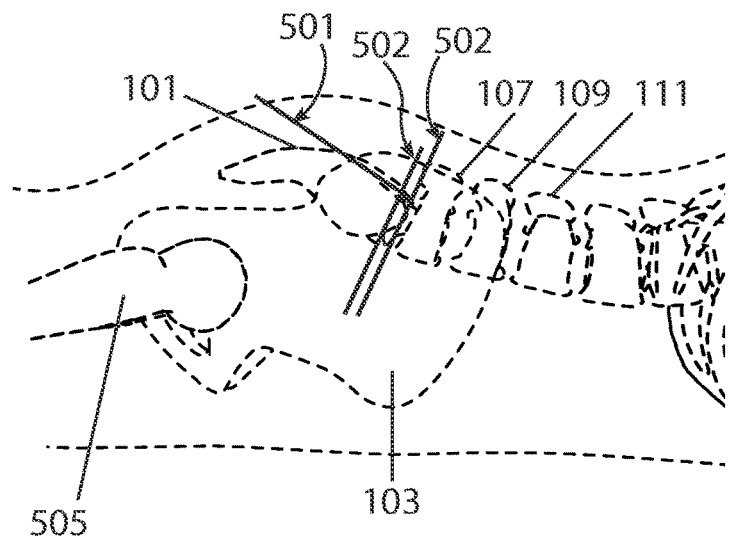
FIG. 11A. An illustrated lateral view of a patient's pelvic region with an imaging device, wherein the general edge lines of the left S1 endplate edge and the right S1 endplate edge do not appear to overlap.
Figure 11B:
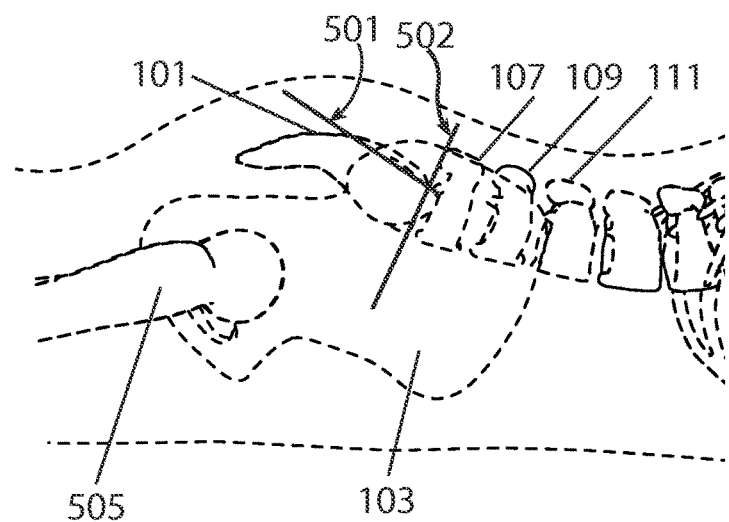
FIG. 11B. An illustrated lateral view of a patient's pelvic region with an imaging device, wherein the general edge lines of the left S1 endplate edge and the right S1 endplate edge appear to overlap.
Figure 11C:
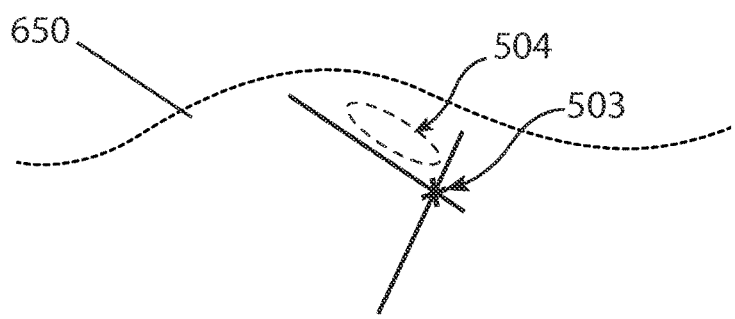
FIG. 11C. An illustrated external lateral view of a patient's pelvic region, wherein the intersection of the general edge lines of the left S1 endplate edge and the right S1 endplate edge and the canal line is marked with an "x".

It will be appreciated that aligning certain anatomical structures of the patient with the view of radiographic images obtained from an imaging device allows one to accurately place a stabilizer device or a bilateral device in subsequent steps. It will be appreciated that in certain embodiments, certain methods described below associated with FIG. 11A, FIG. 11B, and FIG. 11C are performed before or during steps 204, 205 as in FIG. 2A and steps 256, 257, 263, 264 as in FIG. 2B. In a certain embodiment, a medical practitioner views a patient's pelvic region with an imaging device from the lateral view, as illustrated in an example in FIG. 11A. The SI superior endplate 114, as shown in FIG. 1B is generally a flush surface that is located inferior to the L5-SI disc. The left S1 endplate edge 125 and the right S1 endplate edge 126 are regions associated with the S1 superior endplate 114 comprising cortical bone, and thus typically appear as a dense region on images taken by a imaging device.

In one example, as illustrated in FIG. 11A the location of the general edges of the left S endplate edge 125 and/or the right S1 endplate edge 126 may be represented with an edge line 502. If the edge line 502 is non-overlapping, as shown for example in FIG. 11A, a medical practitioner may adjust the patient and/or the imaging device such that in a radiographic image, the general edge lines 502 of the left S1 endplate edge 125 and the right S1 endplate edge 126 appear to overlap, as further exemplified in FIG. 11B. This type of adjustment ensures that the SI superior endplate 114 is parallel to the viewing angle of the bone-imaging device, and further helps to establish accurate stabilizer device path 701 and bilateral device paths 702 in later steps. Moreover, a posterior edge of the sacrum 101, further represented by a posterior edge of an S1 vertebral body 115 and a posterior edge of an S2 vertebral body 127 may be represented by a canal line 501, as shown in FIG. 11A and FIG. 11B. In an embodiment of the invention, an oblong radio-dense objects or a plurality of such objects, (for instance, a wire or a needle) may be placed on the exterior surface of the skin, as to align said objects with the edge line 502 and/or the canal line 501 as it appears on an image from a bone-imaging device, as shown in FIG. 11C. The intersection 503 of the edge line 502 and the canal line 501 may be further marked on the exterior surface of the patient's skin with a pen or marker or other marking tool, by referencing radiographic images from the imaging device comprising the oblong radio-dense objects. The result of the marking on the exterior surface of the patient's skin, as illustrated in FIG. 11C, wherein the intersection 502 is represented with an "x," may be referred to in the proceeding steps.

In certain embodiments, an incision area 504 that is located further posterior (or upwards as shown in FIG. 11C) from the intersection 503, may be marked on a patient's body. Such area, located between 0.5 inches and 3 inches or more posterior and/or inferior from the intersection 503, is a general location for incision sites for one or more stabilizer device paths 701 and bilateral device paths 702 found in the certain embodiments of the invention. In certain other embodiments of the invention, an incision area 504 may further be located up to 6 inches posterior, 6 inches medial, and/or inferior from the intersection 503. Within the incision area 504, a medical practitioner creates one or more incisions to access the hip area from the exterior of a patient's body. An incision, in certain embodiments, is created using instruments related to surgery and/or spinal fusions, such as a scalpel. In general, one or more incisions 652 as shown in FIG. 4C, are created during the skin incision steps 257, 264.

Figure 4C:
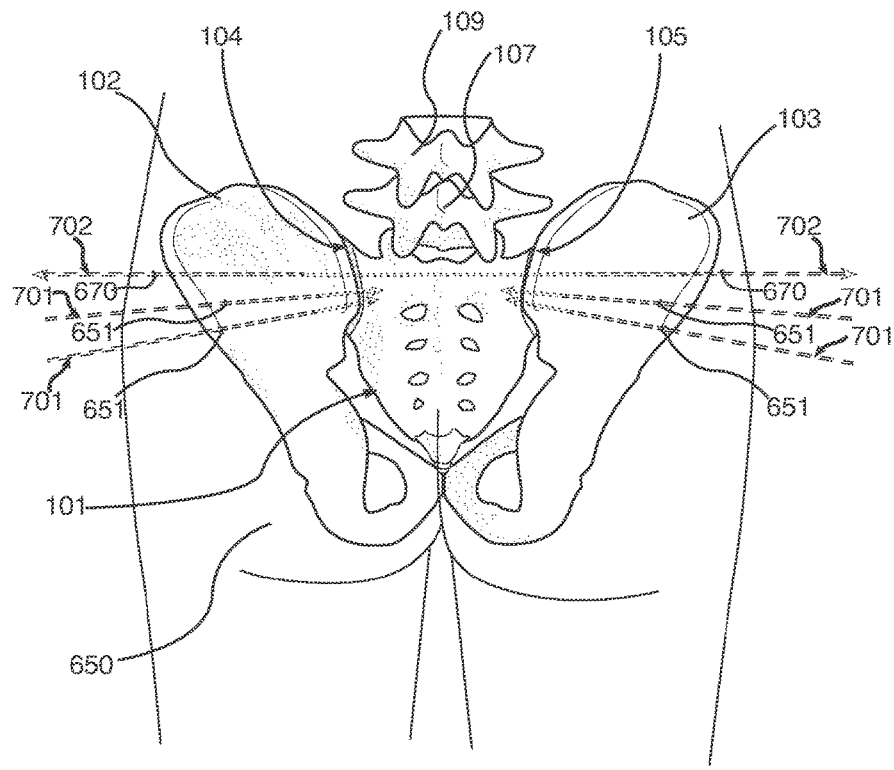
FIG. 4C. Stabilizer device paths and a bilateral device path viewed from a posterior view of a pelvis in certain embodiments of the invention.

Methods related to certain embodiments of the invention use one or more stabilizer device paths 701 on each SI joint, and one bilateral device path 702 across both SI joints, as illustrated in FIG. 4C. Therefore, the location of the one or more other stabilizer device path 701 and bilateral device paths 702 are considered before determining the location of the incision and/or entry point of a needle (e.g. a spinal needle). In certain embodiments, such needle is a trephine needle, for example, a Jamshidi needle having a radio-dense property, and can be referenced in images taken with a imaging device (e.g. radiographic images).

In certain embodiments, a medical practitioner views a patient's pelvic region using a imaging device in the various views, including but not limited to the lateral view, and/or the oblique view during the determine approach angle step 256, shown in FIG. 2B. In certain embodiments, a medical practitioner positions a needle, anticipating the path that a needle would take if, for example, a hypothetical straight line is extrapolated from the needle. Such position of a needle is further visualized with radiographic images. Adjustments to the approach angle and/or potential incision site of a needle are made as needed, until it is confirmed that a needle's path would reach a sacral ala. Such approach angle and/or incision site of a needle are adjusted and verified by referencing lateral-view and/or oblique images taken by an imaging device. In certain embodiments, similar steps are taken during a determine approach angle step 263, as shown in FIG. 2B, associated with determining a bilateral device path 702.

In certain embodiments, one or more incisions 651, 670, as shown in FIG. 4C are created after the determine approach angle steps 256, 263, shown in FIG. 2B. In one example, an incision 651, 670 is a length between 0.5 cm to 2 cm on the patient's buttocks 650, however, the size of the incision 651, 670 is not limited to such size, as it may range from 0.1 cm to 5 cm, or more. In general, the size of said incision to create the incision 651, 670 is matched to the size of the instruments utilized during certain embodiments of the procedure, so as to minimize the size of said incision and/or minimize the invasiveness of the procedure. In one example, as illustrated in the posterior view of a patient in FIG. 8B, a plurality of incisions 651, 670 may be made for the plurality of stabilizer device paths and/or a bilateral device path. It will be appreciated that the incisions can be made on both the left side and right side of a patient. In general, the size and/or shape of the incision may expand, retract, or change based on the elasticity of the skin and tissue of the patient and/or the type of instrument used during embodiments of the invention.

It is the goal and benefit of embodiments of the sacroiliac fusion approach and transsacral bilateral sacroiliac fusion approach, as described here, to not require the opening of a relatively large incision in the skin to access the ilium and sacrum, but rather only require an incision that is preferably between 0.5 cm to 2 cm, or preferably between 0.1 cm to 4 cm, or preferably between 0.05 cm to 6 cm, to allow fusion of a sacrum and an ilium. The advantage of the small incision and the small path created for one or more stabilizer device path 701 or one or more bilateral device path 702 is that healing time and recovery of the skin is dramatically reduced. Furthermore, the small incision may decrease the likelihood of complications associated with surgery, for example, reducing the chances of hematoma and/or bacterial infection of the area, and reducing the risks of slicing or damaging nerves and blood vessels associated with the buttocks and surrounding areas. Additionally, in certain embodiments, a small incision further reduces the time required to perform a sacroiliac fusion approach and/or a transsacral bilateral sacroiliac fusion approach, as a smaller area is opened and sutured.

In general, the certain embodiments of the determine stabilizer device paths step 251 enables a medical practitioner to establish a plurality of stabilizer device paths 701 in a minimally invasive manner. In the preferred embodiment of the invention, the medical practitioner creates two stabilizer device paths 701 to stabilize the sacrum and ilium per SI joint. However, in other embodiments of the invention, the transsacral bilateral sacroiliac fusion approach may comprise between one and four stabilizer device paths 701 per SI joint. Yet in other embodiments of the invention, the transsacral bilateral sacroiliac fusion approach may comprise more than four stabilizer device paths 701 per SI joint. As shown in an example in FIG. 4C, a plurality of stabilizer device paths 701 are in general, non-parallel, or in other words, convergent towards the sacrum. By following convergent paths, a plurality of stabilizer devices can traverse a larger surface area of the sacral and iliac bone and the SI joint space, and further stabilize the sacrum and ilium, as compared to using stabilizer device paths 701 that are parallel. In certain embodiments, a medical practitioner establishes a plurality of stabilizer device paths 701 such that the end of said paths are positioned approximately towards the interior of the sacral ala. However, in some cases, two or more stabilizer device paths 701 may be parallel, or divergent, depending on, for example, the anatomical structure of a patient or availability of usable bone for stabilization with a stabilizer device.

After a skin incision step 257, a medical practitioner performs the insert the trephine needle step 258, needle imaging step 259, and modify needle path step 260 as shown in FIG. 2B in certain embodiments of the invention. The insert trephine needle step 258, the needle imaging step 259, and the modify needle path step 260 relate to the establishment of an initial path through the ilium and to the sacrum. By carefully refining the approach angle and/or approach path using radiographic guidance, the medical practitioner ensures that any unwanted penetration a trephine needle into anatomical structures found exterior of the sacrum, SI joint, and/or ilia are avoided. In certain embodiments, such steps allow careful refinement of the approach angle and/or approach path to establish a path prior to, for example, drilling through bone such as in the drill step 281. Therefore, the insert the trephine needle step 258, needle imaging step 259, and modify needle path step 260 avoid unnecessary drilling in proceeding steps, and can increase the safety, reduce the overall invasiveness of the procedure, and increase the speed at which certain embodiments of the procedure are performed.

The insert the trephine needle step 258 uses the insertion of a piercing tool, such as a trephine needle (e.g. a Jamshidi® Needle or similar device) to penetrate bone, in certain embodiments. In certain embodiments, a piercing tool is placed at an approach path and approach angle as ascertained during the determine the approach angle step 256 and further taps such needle through skin, tissue, onto the surface of an ilium. In the insert the trephine needle step 258, such needle is further tapped into the cortical bone of an ilium.

Following the insert the trephine needle step 258, a radiographic image of the area is taken (during the needle imaging step 259), as to validate the approach angle and/or approach path of such needle as it traverses the ilium. In the needle imaging step 259, the location of the needle, and the predicted trajectory of such needle are evaluated based on images taken from an imaging device, referring to certain views, for example, a lateral view and/or oblique view of the approach area. In one example, a medical practitioner references a lateral view of the pelvis as illustrated in FIG. 6A or FIG. 19B, and/or an oblique view of the pelvis, as illustrated in FIG. 6B or FIG. 19A, such that a potential stabilizer device paths 701 traverse the left ilium 102 and the left SI joint 104 to reach the left sacral ala 122. If a needle has an ideal or near ideal trajectory within the ilium, where its trajectory will traverse the SI joint and enter the sacrum, the medical practitioner may return to the insert the trephine needle step 258, further tapping the needle through the bone. If a needle has a trajectory that may not traverse the SI joint and enter the sacrum, or potentially leads to an area that can cause damage to nearby organs, tissues, nerves, etc, a medical practitioner may alters the approach angle and/or approach path of such needle during the modify needle path step 260. Once such adjustment is made, a medical practitioner may continue with the insert the trephine needle step 258. In certain embodiments, steps 258, 259, and 260 are repeated until a needle enters and traverses the SI joint, and further enters a sacrum. In embodiments of the invention, advancement of a needle is stopped when such needle penetrates a cortical layer of a sacrum.

Figure 14A:
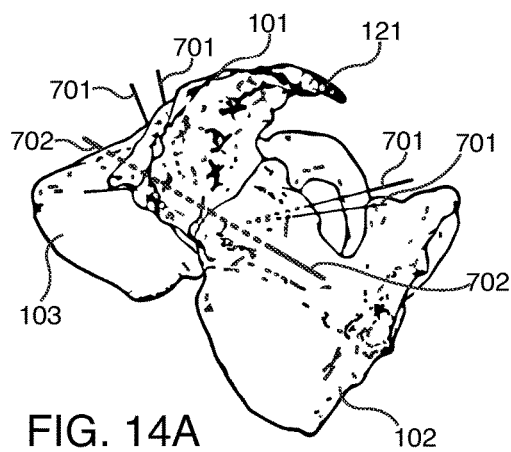
FIG. 14A. Representative perspective view of a pelvis showing stabilizer device paths and a bilateral device path, in one embodiment of the invention.
Figure 14D:
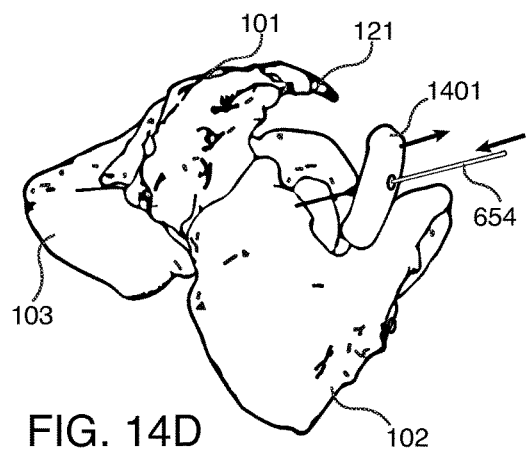
FIG. 14D. Representative perspective view of a pelvis showing insertion of a guide wire through an opening of a trephine needle, in one embodiment of the invention.
Figure 14B:
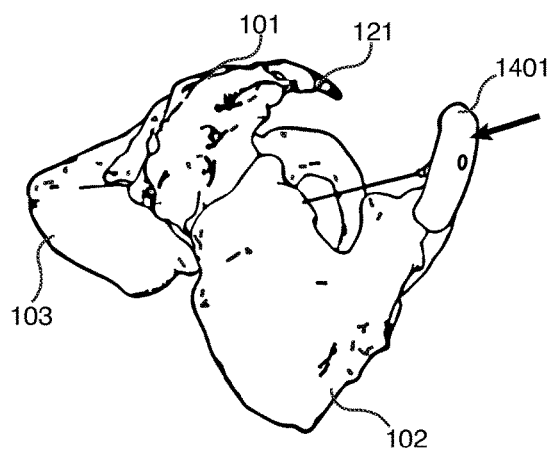
FIG. 14B. Representative perspective view of a pelvis showing insertion of a trephine needle through a stabilizer device path, in one embodiment of the invention.

Referring to FIG. 14, in certain embodiments of the invention, a trephine needle 1401 is inserted through the ilium into the sacrum as shown in FIG. 14B, (during step 206 or 258). Such trephine needle 1401, located on an exterior surface of the ilium 102, follows one of the stabilizer device paths 701 as shown in FIG. 14A. The medical practitioner further inserts such needle 1401, as shown in FIG. 14C, by tapping it through bone and following steps 258, 259, and 260 as in FIG. 2B (which is similar to steps 204, 205, and 206 as in FIG. 2A). During step 259 (or step 207) lateral view and/or oblique view radiographic images taken with an imaging device are used to verify the predicted trajectory of a needle, and the path of a needle may be modified as such needle passes into the sacrum during step 260 (or step 208), as to ensure that a needle 1401 does not penetrate the edges of the ilium or sacrum.

Figure 14E:
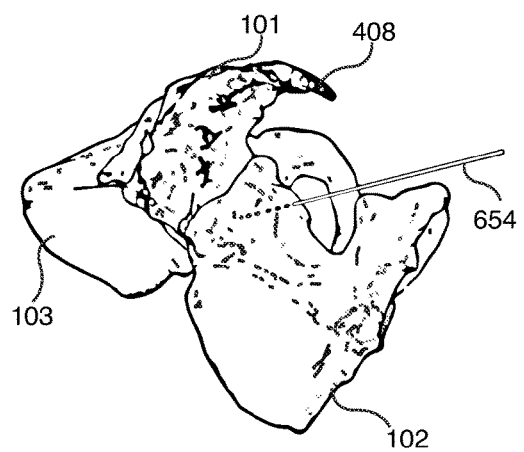
FIG. 14E. Representative perspective view of a pelvis showing placement of guide wire through a stabilizer device path, in one embodiment of the invention.
Figure 14C:
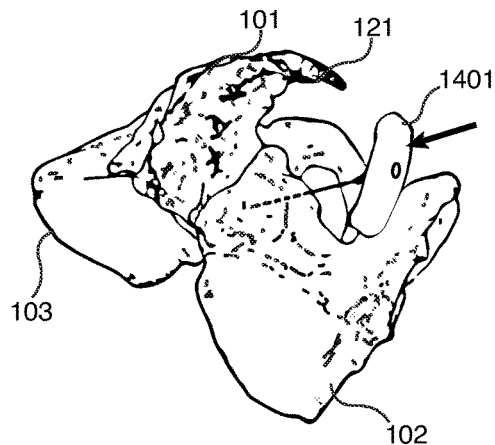
FIG. 14C. Representative perspective view of a pelvis showing further insertion of a trephine needle through the ilium and sacrum following a stabilizer device path, in one embodiment of the invention.
Figure 14F:
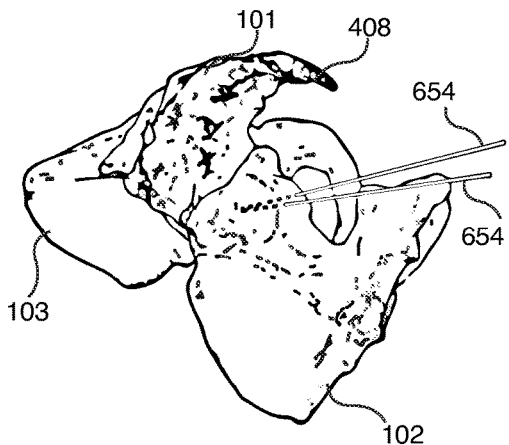
FIG. 14F. Representative left posterior-superior perspective view of a pelvis showing placement of a plurality of guide wires through stabilizer device paths, in one embodiment of the invention.

In certain embodiments, once the trephine needle penetrates a cortical bone of the sacrum, the insert guide wire step 261 is performed. As illustrated in FIG. 14D, a guide wire 654 is inserted through such trephine needle 1401, essentially allowing such guide wire to follow the path of a stabilizer device path 701. Moreover, the medical practitioner may remove such trephine needle from the patient's body, as shown in FIG. 14E, leaving the guide wire 654. In certain embodiments, the insert guide wire step 261 effectively establishes a path from an exterior of the body to an end point within the sacrum. In certain embodiments, one or more paths may be established, and a guide wire 654 may be placed in such paths 701, as illustrated in FIG. 14F. In certain embodiments, one or more stabilizer device paths 701 may be created during the transsacral bilateral sacroiliac fusion approach, and such paths may be establish on the left SI joint, right SI joint, or both joints on a patient's hip.

It will be appreciated that the examples as illustrated in FIG. 14 may also be used to show how steps in certain embodiment of the invention are performed, more specifically those steps disclosed in step 201, as shown in FIG. 2A. It will be appreciated that certain steps, procedures, and instruments, related to step 251 have similarities with the determine stabilizer device paths step 201 shown in FIG. 2A.

Steps Associated with Establishing a Bilateral Device Path

Figure 5A:
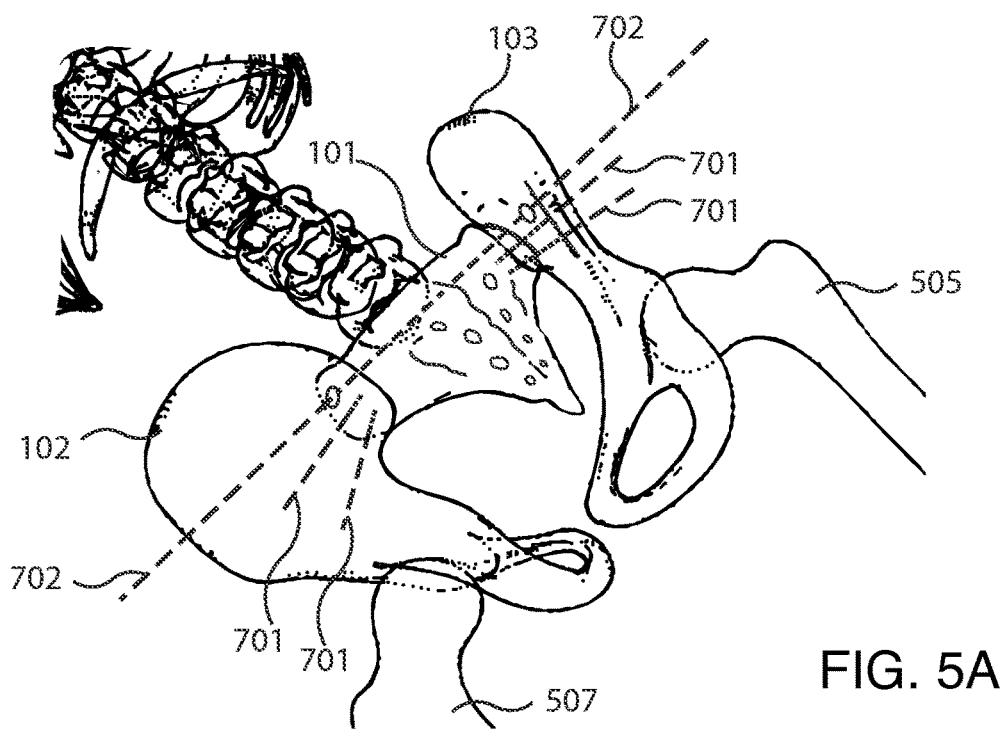
FIG. 5A. Left posterior-caudal perspective view of a pelvis showing stabilizer device paths and a bilateral device path in certain embodiments of the invention.
Figure 5B:
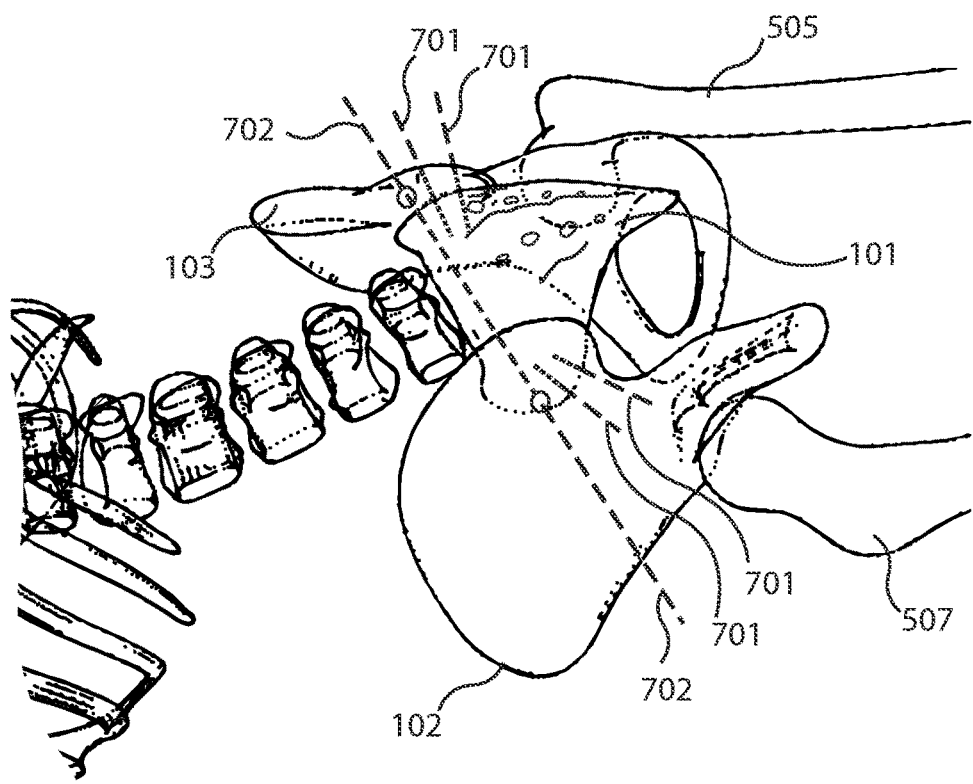
FIG. 5B. Left posterior-rostral perspective view of a pelvis showing stabilizer device paths and a bilateral device path in certain embodiments of the invention.

In certain embodiments of the invention, during a determine bilateral device paths step 252, as shown in FIG. 2B, a bilateral device path 702 is established, as shown in, for example, FIG. 5A and FIG. 5B. Referring to FIG. 2B, a determine bilateral device paths step 252, further includes, but is not limited to a number of sub-steps, for example: 1) determine approach angle step 263; 2) skin incision step 264; 3) insert trephine needle step 265; 4) needle imaging step 266; 5) modify needle path step 267; 6) insert guide wire beyond midline step 268; 7) drill step 269; and 8) insert guide wire step 220. It will be appreciated that other embodiments of the invention are not limited to these sub-steps or in a particular order, for example, variations in the order of the sub-steps may be performed, and such sub-steps are meant to be exemplary rather than limiting.

While performing embodiments of a determine approach angle step 263, a number of different radiographic views of a patient's pelvic region are referenced, such views including but not limited to a lateral view, oblique view, inlet view, outlet view, and AP view. The approach angle and/or potential incision site of a needle are adjusted so that an extrapolated path of the needle appears to take a path 702 across a left ilium 102, a right ilium 103, and through the S1 vertebral body 115, as shown in FIG. 5A and FIG. 5B. An incision 670, as shown in FIG. 4C, to place a bilateral device is approximately the size of a device used during certain embodiments of the invention. In one example, an incision 670 during step 264 is a length between 0.5 to 2 cm on the patient's buttocks 650; however, the size of the such incision 670 is not limited to this size. It will be appreciated that a size and/or shape of the incision 651, 670 may expand, retract, or change based on the elasticity of the skin and tissue of the patient and/or the type of instrument used in associated with certain embodiments of the invention.

Generally, the determine bilateral device path step 252, in certain embodiments of the invention, allows one to establish one or more bilateral device paths 702 in a minimally invasive manner. Preferably, one bilateral device paths 702 is created to stabilize a sacrum, left ilium, and right ilium. However, in other embodiments of the invention, the transsacral bilateral sacroiliac fusion approach may comprise more than one bilateral device paths 702. It will also be appreciated that in certain embodiments, other portions of the sacrum, for example, the S2 vertebral body, or S3 vertebral body may serve as a passageway for a path. As illustrated in FIG. 5A and FIG. 5B, a bilateral device path 702 spans across both the left ilium 102 and right ilium 103 through an S1 vertebral body 115.

Typically, the S1 vertebral body 115 of an adult human is generally in a form resembling a box or cylinder, having a thickness that spans approximately 20 mm to 70 mm. One dimension of a thickness may be measured by the distance between an upper anterior S1 border 1101 and a lower posterior S1 border 1102, as illustrated in an inlet view of a pelvic region in FIG. 12A, and a second dimension of a thickness may be measured by the distance between a upper posterior S1 border 1201 and a lower anterior S1 border 1202, as illustrated in an outlet view of a pelvic region in FIG. 12B. However, it will be recognized that there is variability among patients, and certain patients may have S1 vertebral bodies having thicknesses less than 20 mm or greater than 70 mm. In general, however, concepts related to certain embodiments of the invention are related to creating a path 702 from a left ilium to a right ilium, through an S1 vertebral body, and stabilizing one or more SI joints. It will also be appreciated that in certain embodiments, one or more SI joints are stabilized by establishing a path between the left ilium and right ilium through an S2 vertebral body.

Figure 12A:
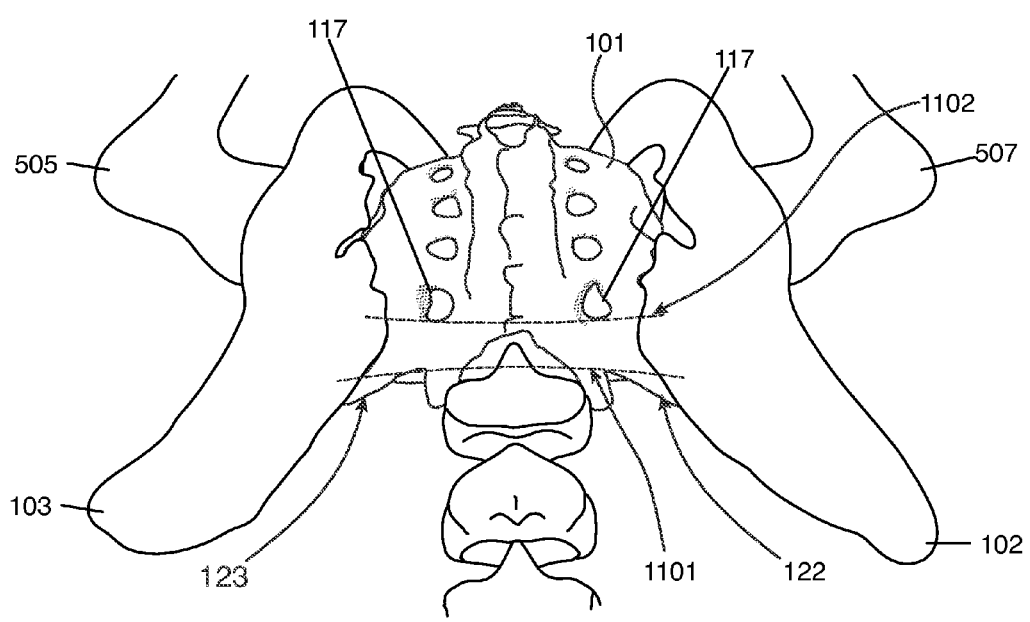
FIG. 12A. Representative inlet x-ray view of a pelvis, showing structural boundaries of the S1 vertebral body.

While performing certain embodiments of the determine bilateral device path step 252, penetration with an object beyond an upper anterior S1 border 1101 is prevented by using an inlet x-ray view of the pelvic region, as exemplified by FIG. 12A. An upper anterior S1 border 1101, in general, is a border that has an S1 superior endplate 114, and the superior cortical edges of a left sacral ala 122 and a right sacral ala 123. Penetration with an object, beyond the cortical bone associated with a lower posterior S1 border 1102 is also prevented with an inlet view, using an inlet view as exemplified in FIG. 12A. Generally, a lower posterior S1 border 1102 further comprise an edge of the S1 foramina 117, further referenced in FIG. 1B and FIG. 1C, where typically the S1 nerve roots and blood vessels traverse such S1 foramina 117. Therefore, it will be appreciated that an inlet view allows one to prevent objects, such as medical instruments, from penetrating the cortical bone associated with the S1 foramina 117.

Figure 12B:
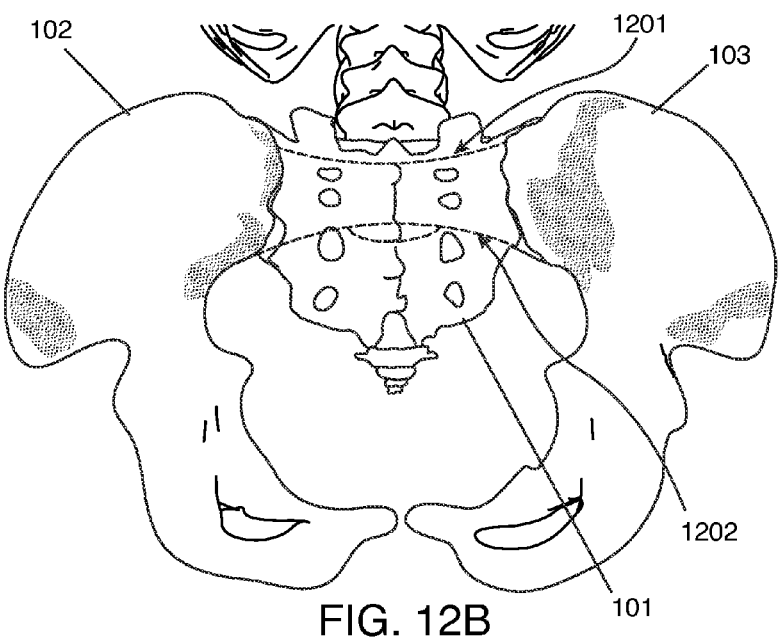
FIG. 12B. Representative outlet x-ray view of a pelvis, showing structural boundaries of the S1 vertebral body.

While performing certain embodiments of the determine bilateral device path step 252, penetration beyond an upper posterior S1 border 1201 and a lower anterior S1 border 1202 are prevented using an outlet view, as exemplified in FIG. 12B. An upper posterior S1 border 1201 further has an anterior cortical border of a sacral canal 124, where typically, S1, S2, S3, S4 and S5 nerve roots, the coccygeal nerves, and blood vessels may pass through such sacral canal 124. A lower anterior S1 border 1202 has a cortical bone edge that is adjacently located to the abdominal cavity. As exemplified in FIG. 12B, an outlet view is referenced in certain embodiments of the invention as to prevent objects, such as medical instruments, from penetrating cortical bone associated with the upper posterior S1 border 1201 and/or Anterior S1 Border 1202.

Moreover, an inlet view and outlet view are important to verify, and ensure that objects used in certain embodiments of the invention traverse the S1 vertebral body 115 relatively through the middle of such body. Traversing relatively through the center of an S1 vertebral body during the insert trephine needle step 265 ensures that other objects, for example, such as a bilateral device, has enough room within the S1 vertebral body 115.

A number of different radiographic views are used for the duration of certain steps associated with embodiments of the invention. For example, during embodiments of performing the determine bilateral device path step 252 and the secure SI joint with bilateral device step 255, the inlet view of the pelvic region as illustrated in FIG. 12A and the outlet view of the pelvic region, as illustrated in FIG. 12B are used. Additionally, an oblique view, a lateral view, and AP view, among others may be used. Such views are not limited to these steps, and it will be appreciated that a number of views can be used for the duration of the procedure. Referencing these views allow medical instruments used during the procedure to stay within the confines of the bone structure, and pass horizontally through the S1 vertebral body 115. In certain embodiments of the invention, it is highly important that any object, such as medical instruments, do not stray from certain embodiments of an intended path 702 (i.e. leave certain bone structures), as progressing beyond an intended path has potential to cause damage to nerves, organs, tissues, blood vessels, and other organic regions surrounding the ilia and sacrum. Therefore, it will be appreciated that referencing radiographic images, including, but not limited to an inlet view, outlet view, lateral view, AP view, and oblique view, and other radiographic views related to certain embodiments of a transsacral bilateral sacroiliac fusion approach ensures that a bilateral device path 702 is created safely, while maximizing the stability of the SI joints for patients having pain or discomfort related to SI joint instability.

The approach angle and/or approach path of a needle are created and refined while performing certain embodiments of the insert needle step 265, the needle imaging step 266, and the modify needle path step 267, as to create a bilateral device path. The insert needle step 265 may include inserting, or tapping a piercing tool, such as a trephine needle (e.g. Jamshidi® needle or similar device), to penetrate through a bone structure. After performing the insert needle step 265, a needle imaging step 266 is performed to validate the approach angle and/or approach path of a needle, as it traverses an ilium, through a sacrum, and through an ilium. In the needle imaging step 266, the location and predicted trajectory of a needle is viewed with images obtained from an imaging device. In certain embodiments, an inlet view, outlet view, lateral view, and/or oblique view, and other views are referenced. In one example, if a trephine needle has a predicted trajectory that stays within the structure of an ilium and sacrum, the insert needle step 265 is continued and a needle is further tapped into the ilium or sacrum. If a needle does not have an ideal trajectory (e.g. has a possibility of hitting nerves, vessels, tissues, organs, etc), the modify needle path step 267 is performed, and the approach angle and/or approach path of such needle is adjusted.

Because radiographic guidance allows avoiding certain structure, such as borders 1101, 1102, 1201, and 1202, the insert needle step 265, the needle imaging step 266, and embodiments of the modify needle path step 267 can increase the safety, reduce the overall invasiveness of the procedure, and increase the speed at which a transsacral bilateral sacroiliac fusion approach is performed, saving time and cost as compared to other procedures.

Figure 15A:
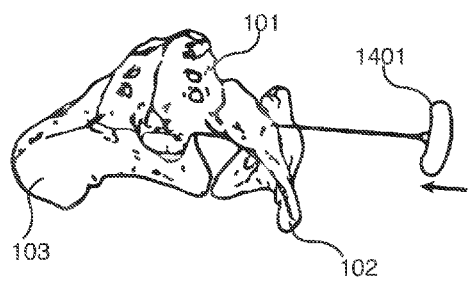
FIG. 15A. Representative perspective view of a pelvis showing insertion of a trephine needle through a bilateral device path, in one embodiment of the invention.
Figure 15D:
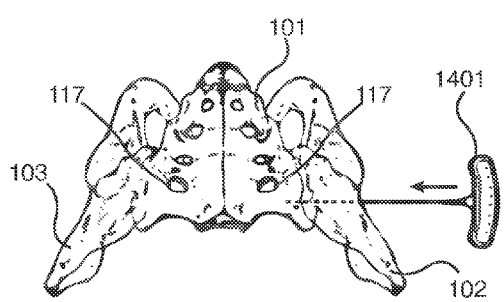
FIG. 15D. Representative inlet view of a pelvis showing passage of a trephine needle through a bilateral device path, in one embodiment of the invention.
Figure 15B:
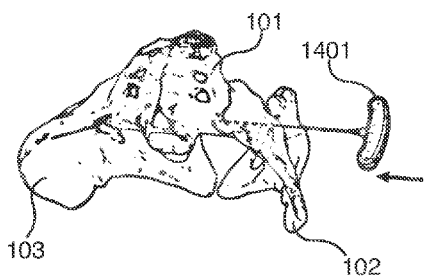
FIG. 15B. Representative perspective view of a pelvis showing further insertion of a trephine needle through an ilium following a bilateral device path, in one embodiment of the invention.

In certain embodiments, a needle is tapped through a first ilium and through a portion of a sacrum, for instance, until the tip of such needle passes a middle of a sacrum. As illustrated in the example in FIG. 15, a trephine needle 1401 is inserted through an ilium into the sacrum. As shown in FIG. 15A a trephine needle 1401 is placed on a path that is substantially on a stabilizer device path. Such trephine needle 1401 is further tapped into the ilium, as shown in FIG. 15B, by referencing radiographic images taken in an inlet view, outlet view lateral view and/or oblique view, or others, of the area. During the modify needle path step 267, the path of a needle may be adjusted to ensure that such needle stays within an S1 vertebral body, and does not penetrate beyond certain borders 1101, 1102, 1201, and 1202. In certain embodiments, an outlet view as exemplified in FIG. 15C may be used as to ensure that a trephine needle or other objects a lower posterior S1 border 1102 and/or the upper posterior S1 border 1201 shown in FIG. 12B. In certain embodiments, an inlet view, as shown in FIG. 15D may be used to ensure that objects do not penetrate the upper anterior S1 border 1101 and/or the lower posterior S1 border 1102, and particularly avoid the S1 foramina 117 containing the S1 nerve root, as shown in FIG. 12A.

Figure 15E:
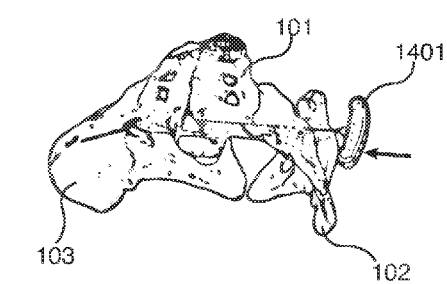
FIG. 15E. Representative perspective view of a pelvis showing further insertion of trephine needle further passing a sacral midline and following a bilateral device path, in one embodiment of the invention.
Figure 15C:
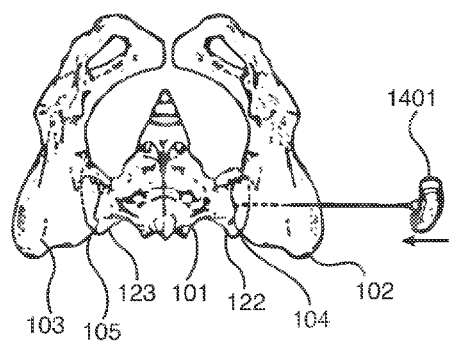
FIG. 15C. Representative outlet view of a pelvis showing passage of a trephine needle through a bilateral device path, in one embodiment of the invention.
Figure 15F:
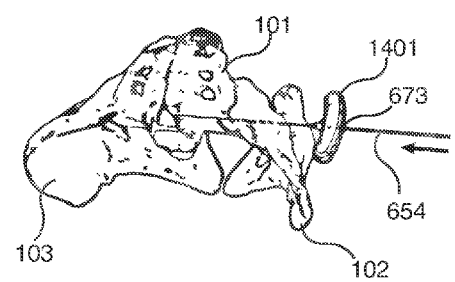
FIG. 15F. Representative perspective view of a pelvis showing a guide wire being inserted through an opening of a trephine needle, and following a bilateral device path, in one embodiment of the invention.
Figure 17A:
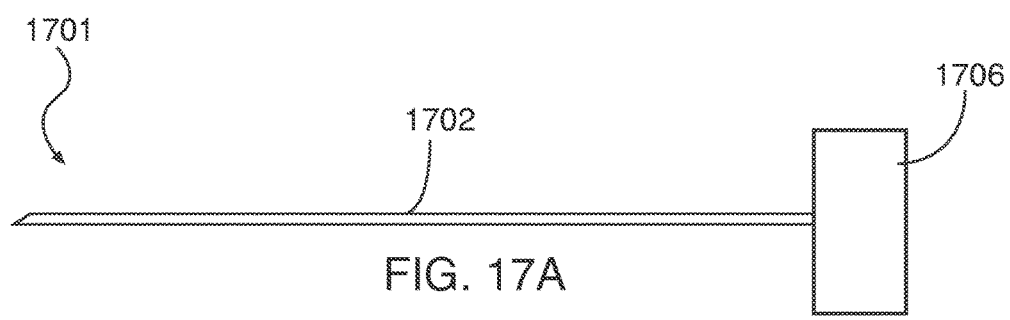
FIG. 17A. An embodiment of the trephine needle.
Figure 17B:
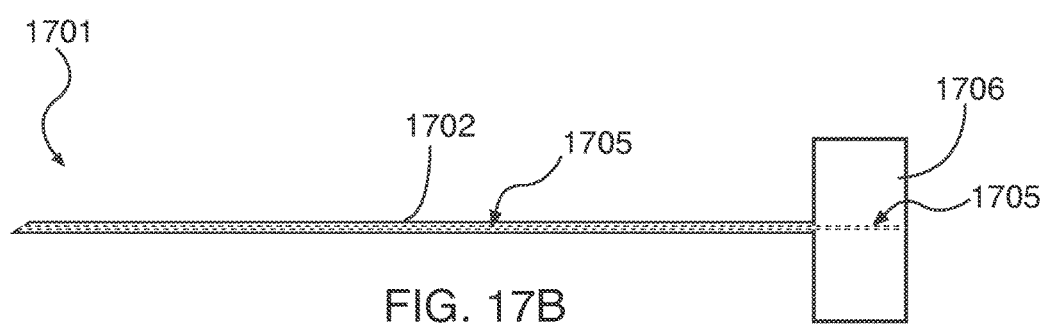
FIG. 17B. A cross-sectional view of an embodiment of a trephine needle.

In certain embodiments, a trephine needle 1401 is advanced until it passes the midline of the sacrum 101, as illustrated in FIG. 15E, during the insert trephine needle step 265 as shown in FIG. 2B. In certain embodiments, a trephine needle is pushed beyond a midline of the sacrum. In certain embodiments, a trephine needle, having a needle portion long enough to traverse such distance may be used. In certain embodiments, during step 268, a trephine needle may be pushed until it hits a distal cortical bone of a sacrum. In certain embodiments, a trephine needle may be used to pierce through a distal cortical bone of a sacrum, and in certain embodiments further past a distal SI joint, and in certain embodiments further past a distal ilium. A trephine needle 1701, as shown for example in FIG. 17A, may have a needle 1702 long enough to reach past the midline of a sacrum from the exterior of the patient's body, and a blunt end 1706 for tapping or pushing such needle through the bone, may be required for certain embodiments of the invention. In certain embodiments, such needle 1702 has a diameter that is between 0.5 mm and 5 mm, and/or further has a length that is preferably between 6 inches (15 cm) and 24 inches (61 cm). In certain other embodiments, such diameter may be between 0.1 mm and 10 cm, and/or having a length that is between 12 inches (30 cm) and 50 inches (127 cm). Such needle 1702 further has an axial opening 1705, as illustrated in a cross sectional view of an embodiment of the invention shown in FIG. 17B, where smaller diameter objects, such as a guide wire, can pass through a needle 1702. While performing embodiments of the insert guide wire beyond midline step 268, a guide wire 654 is inserted through a trephine needle, as illustrated in FIG. 15F. Such trephine needle may be removed, leaving the guide wire 654 within the sacrum. In certain embodiments, step 268 may include using a needle 1702 that penetrates through one ilium, through a sacrum, and through a second ilium.

In certain embodiments, a transsacral path (passing through an ilium, a sacrum, and an ilium) is extended using a drill, during the drill step 269, so that a path or an opening is established laterally from one side of the pelvis to the other side. As illustrated in FIG. 16, a drill 1601 having a drill bit 1602 may be used to expand and extend the aperture of the bilateral device path 702, further through a sacrum 101 and an ilium 103.

A drill 1601, attached to a substantially rigid drill bit 1602 allows further drilling through a sacrum 101, a left ilium 102, and a right ilium 103, as shown in FIG. 16A, FIG. 16B, FIG. 16C, and FIG. 16D. In certain embodiments, a drill bit 1602 is attached to a rotating aspect (e.g. chuck) 1603 of a drill 1601, allowing a drill bit 1602 to axially rotate with the motorized action of a drill 1601, as commonly found in medical drills. In certain embodiments, a drill bit has a cutting end and a shaft. A cutting end further has a flute and/or a plurality of flutes and a cutting edge. Such flute and edge have sharpened features that allow boring or drilling through bone. In certain embodiments, a shaft is a smooth cylindrical feature. In certain embodiments, a flute may span an entire length of a drill bit. In certain embodiments, a guide wire having a sharpened tip may be used to drill a transsacral path.

Figure 16A:
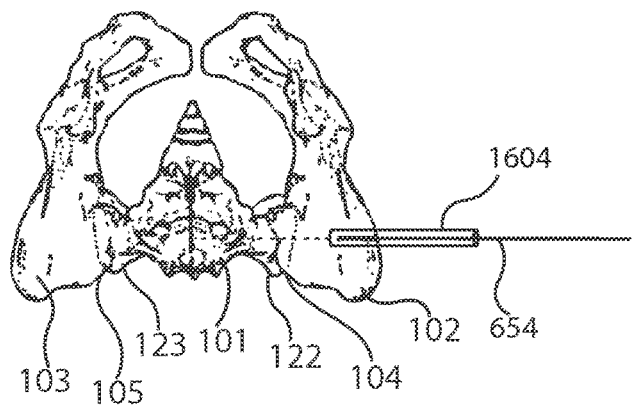
FIG. 16A. Representative outlet view of a pelvis, where a guide wire is placed through a bilateral device path, further showing an access portal, in one embodiment of the invention.
Figure 16B:
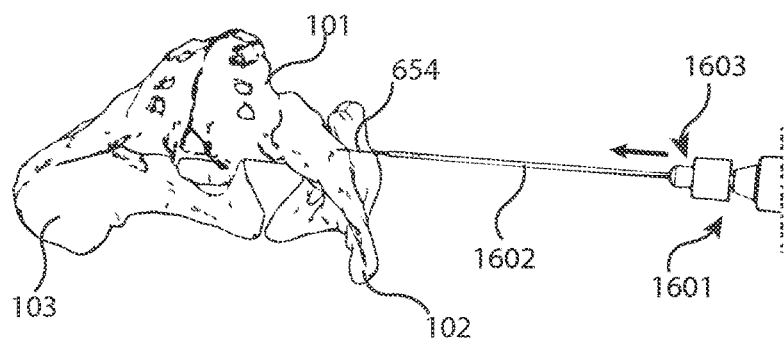
FIG. 16B. Representative perspective view of a pelvis, where a drill follows a path of a guide wire, in one embodiment of the invention.
Figure 16C:
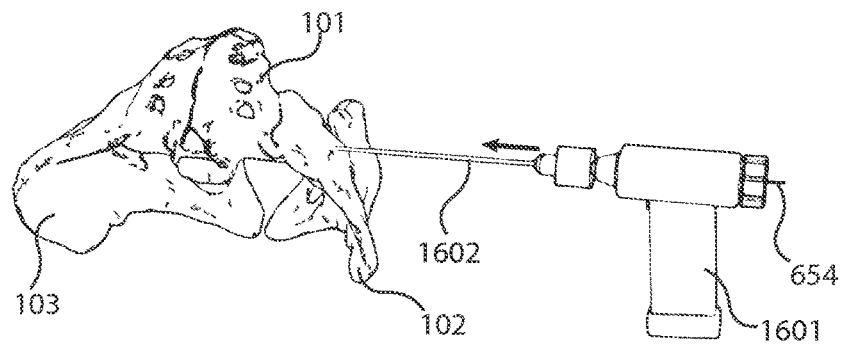
FIG. 16C. Representative perspective view of a pelvis, where a drill follows a path of a guide wire into the ilium and sacrum, which follows a bilateral device path, in one embodiment of the invention.
Figure 16D:
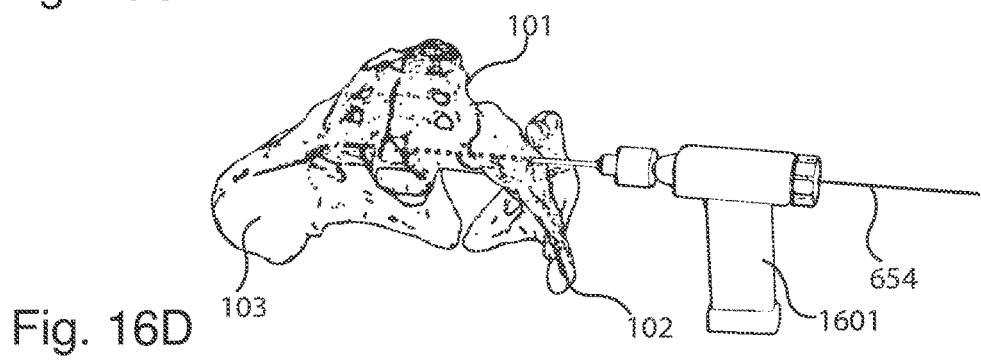
FIG. 16D. Representative perspective view of a pelvis, where a drill further follows a guide wire and passes through a sacrum, in one embodiment of the invention.

Embodiments of a drill bit 1602 preferably have an axial opening 1303, as it allows sliding the drill bit 1602 and associated drill 1601 over a guide wire 654, as illustrated in FIG. 16B. Preferably, certain embodiments of a drill bit 1602 have an outer diameter that allows passage through an S1 vertebral body without penetrating beyond borders 1101, 1102, 1201, and 1202. In certain embodiments, a drill bit 1602 is passed over a guide wire 654, as shown in FIG. 16B, and further used to drill into the bone, for example, an left ilium 102, a sacrum 101, and a right ilium 103, as further shown in FIG. 16C and FIG. 16D.

In certain embodiments of the invention, a drill bit 1602 having a sufficient length to create a continuous passage through the ilia and sacrum is needed. In certain embodiments, a length of a drill bit 1602 is between 10 inches (25 cm) and 50 inches (127 cm), and more preferably, between 12 inches (30.5 cm) and 30 inches (76 cm) in length. Due to the variability in anatomical features of patients, such as a distance between the left and right ilia through an S1 vertebral body, certain embodiments of the invention may require having different length drill bits 1602 for use in their respective situations. A drill bit 1602 having a length greater than typically found in the prior art allows creation of a continuous opening that follows a path 702, through a left ilium, right ilium, and sacrum.

In certain embodiments, a drill 1601 and a drill bit 1602 expands and extends the opening of a path 702 from one side of a patient's ilium to the other side of the other ilium. Inserting a trephine needle, and subsequently a guide wire to at least the midline of a sacrum 101 during the insert trephine needle step 265 and insert guide wire beyond midline step 268, allows a portion of a path 702 to be established prior to drilling. In certain embodiments, a trephine needle or a guide wire may be pushed until such guide wire reaches other features, including, but not limited to a right sacral ala 123, a right SI joint 105, or a right ilium 103, as shown in FIG. 16A. In certain embodiments, a path may be altered while a path is drilled during drill step 269. Additionally, using radiographic images while performing steps 263, 264, 265, 266, 267, 268, 269, and 270 (referring to FIG. 2B) ensures that the trajectory of a path 702 effectively passes through the ilia and sacrum safely, without deviating into anatomical features that have potential to cause harm to a patient. Further, the passing of a drill bit 1602 over a guide wire 654 as described for drill step 269 ensures that a path of such drill bit remains undeviating (i.e. remains on an ideal path) as established during, for example, steps 265, 266, 267. While performing certain embodiments of a drill step 269, an opening through the left ilium, sacrum, and right sacrum is created using a drill bit 1602. Radiographic images may be referenced, for example, an inlet view, outlet view, lateral view, and oblique view, so that the path of said drill bit 1602 reaches the other side.

In certain embodiments, an access portal 1604, such as, but not limited to a tube or dilator, may be used to protect surrounding structures such as tissue, structures related to the circulatory system, structures related to the nervous system, as shown in FIG. 16A as a drill bit 1602 is used to create an opening through bone.

Once a passage from a first ilium (proximal) to a second ilium (distal) is created, a guide wire 654 is passed through a axial opening of the drill bit 1602, during the insert guide wire step 270, as to ensure that other instruments can follow the path of such guide wire. In certain embodiments, a trephine needle 1401, 1701, may be placed along a path, until it passes through and out a patient's body as to ensure that a guide wire following the trephine needle can span across one ilium, through a sacrum, across a second ilium— from one exterior side the other exterior side of the patient. In certain embodiments, an incision on the other side of the body is created, and a trephine needle is guided through that incision to the distal ilium.

Steps Associated with Establishing a Decortication Path

In general, in certain embodiments, the purpose of the determine decortication path step 253, shown in FIG. 2B, is to allow effective decortication of an SI joint such that articular surfaces of a sacrum and ilium are prepared for bone fusion. In one aspect, one or more stabilizer devices, and one (or more) bilateral device mechanically secure one or more ilium and a sacrum. In another aspect, graft material placed in an SI joint space allows bone fusion within an SI joint. In certain embodiments, a combination of approaching the SI joint from a stabilizer device approach 301, bilateral device approach 302, and a decortication approach 303, as shown in FIG. 3B is greatly beneficial for stabilizing at least one, and more preferably both SI joints. In certain embodiments, the determine decortication paths step 253 is intended to access an SI joint through a decortication approach 303, as shown in FIG. 3B. In certain embodiments, as shown in FIG. 4A and FIG. 4B, one or more oblique paths 703 are created.

In certain embodiments, while one performs the determine decortication path step 253 as shown in FIG. 2B, a general pathway of a decortication approach 303, as shown in FIG. 3B, is used as a guide for creating one or more oblique paths 703. As shown in an embodiment in FIG. 2B, a determine decortication paths step 253 further includes, but is not limited to a number of sub-steps, such as: 1) determine approach angle step 271; 2) skin incision step 272; 3) insert guide wire step 273; 4) expand path to joint with dilators step 274; 5) deliver access portal step 275; 6) expand joint space step 276; 7) decortication step 277; 8) obtain graft material step 278; 9) pack graft material step 279; and repeat fusion approach step 280. It will be appreciated that in other embodiments, step 253 is not limited to these sub-steps, and as these sub-steps are meant to be exemplary rather than limiting. It will be appreciated that certain steps, procedures, and instruments, related to step 253 have similarities with the determine decortication path step 202 shown in FIG. 2A, and certain sub-steps of step 202 may be used for the transsacral bilateral sacroiliac fusion approach.

In certain embodiments, performing the determine decortication path step 253 allows one to establish one or more oblique paths to access an SI joint. In certain embodiments, establishing one or more oblique paths 703 into a SI joint, as shown in FIG. 18A, allows effective decortication of the articular surfaces of an SI joint, including the surfaces of an ilium and sacrum. In certain embodiments, one or more oblique paths is established per SI joint. In certain embodiments, two or more paths 703 are established per SI joint. An oblique path 703, generally follows a direction of the decortication approach 303 as illustrated in FIG. 3B. As shown in FIG. 18A showing an illustrated posterior view of a patient, a plurality of oblique paths 703 may be generally, non-parallel, or convergent towards the left SI joint 104, or right SI joint 105. As shown in views FIG. 7A and FIG. 7B, paths 703 are generally parallel to the plane of an SI joint.

In certain embodiments, the determine approach angle step 271 shown in FIG. 2B is performed in a similar manner as described for step 211 shown in FIG. 2A and as disclosed above. While performing the determine approach angle step 271, a needle 1901 is placed on an exterior portion of a potential incision site, and the approach angle and/or potential incision site of such needle is adjusted so that the angle of entry of such needle is in a direction of the decortication approach 303 as illustrated in FIG. 3B. In certain embodiments, the incision points 652 to access either the left SI joint 104 or right SI joint 105, as shown in FIG. 18A and FIG. 18B are empirically determined. In certain embodiments, radiographic images in an oblique view, as exemplified in FIG. 19A and/or the lateral view, as exemplified in FIG. 19B, are used to view a patient while performing the determine approach angle step 271 for a left SI joint 104. It will be appreciated that an oblique view and lateral view for a right SI joint 105 will look differently than illustrated in the examples in FIG. 7A and FIG. 7B.

In one example, a medical practitioner references an oblique view, as exemplified in FIG. 19A, where such oblique view is generally in a plane that is parallel to an SI joint (e.g. left SI joint 104). In another example, a medical practitioner references a lateral view, as exemplified in FIG. 19B. A number of radiographic images may be taken and referenced until a needle 1902 is oriented to align with a plane of a left SI joint 104. In certain embodiments, a hypothetical straight line 1902 extrapolated from a needle 1901 is extended to the SI joint 104, as shown in FIG. 19A and FIG. 19B. If such line 1902 allows entry into an SI joint, such path is used, and considered to be a path 703. An end 1903 of a needle 1901 is used to mark the surface of the skin (e.g. buttocks 650) as the location of an incision.

In certain embodiments of the invention, a skin incision step 272 is generally performed after a determine approach angle step 271. Such skin incision step 272 shown in FIG. 2B is performed in a similar manner as described for step 212 shown in FIG. 2A, and as disclosed above. In general, a skin incision 272 step creates the initial incision 652 for the oblique paths 703, wherein such incision 652 is approximately the size of the instruments utilized during certain embodiments of the invention.

An incision 652, as shown in FIG. 18A and FIG. 18B is approximately the size of the instruments utilized during certain embodiments of the invention. In one example, an incision 652 created during step 272 is between 0.5 to 3 cm on a patient's buttocks 650. In certain embodiments, such incision is between 0.1 cm and 5 cm, or more. As shown in FIG. 18B, an incision 652 allows access the left SI joint 104 or right SI joint 105 in subsequent steps. In general, the size of said incision is approximately the size of certain instruments used during the determine decortication path step 253, allowing one to minimize the invasiveness the approach. An SI joint may be visualized from the exterior of the patient's body by inserting an endoscope, through the oblique paths, or visually inspecting (i.e. direct visualization) the SI joint by further increasing the size of incision 652 and subsequently expanding the skin with appropriate instruments, for example, tissue retractors, access portals, cannula, dilators. In some cases, inspection of an SI joint may be beneficial, for example, as to follow comply with Centers for Medicare and Medicaid Services (CMS) guidelines or insurance guidelines associated with policies for approval and reimbursement.

While performing certain embodiments of an insert guide wire step 273, as shown in FIG. 2B, radiographic images in an oblique view as exemplified in FIG. 19A, and a lateral view as exemplified in FIG. 19B are referenced to advance a guide wire through the buttocks tissue to reach the SI joint. In certain embodiments, a guide wire 671 establishes a physical path 703 from the exterior of the body to the left SI joint 104 or right SI joint 105. In certain embodiments, a trephine needle 1401 is placed through an incision 652, as shown in FIG. 19C, and further tapped into an SI joint 104, as shown in FIG. 19D. Once a tip 672 of such trephine needle 1401 is tapped into an SI joint 104, as shown in FIG. 19D, a guide wire 671 may be placed through an opening 673 of a trephine needle 1401, until the tip of such guide wire reaches such SI joint, as shown in FIG. 19E. A trephine needle is then removed, leaving a guide wire, as shown in FIG. 19F. It will be appreciated that one or more guide wires 671 may be inserted for accessing an SI joint, as represented in FIG. 19F.

After step 273, in certain embodiments, the procedure may be followed with an expand path to joint with dilators step 274, as shown in FIG. 2B. Typical dilators have an opening that allows such dilator to slide over a guide wire or other dilators, so that so as to expand an opening of the stabilizer device paths 701, bilateral device paths 702, and/or oblique paths 703. In certain embodiments, using successively larger dilators through the stabilizer device paths 701, bilateral device paths 702, and/or oblique paths 703 stretches tissue surrounding a guide wire, and allows larger instruments, devices, or materials to enter. For instance, in certain embodiments, a series of successively larger dilators have diameters that are 2.5 mm, 4.5 mm, 6.5 mm, and 10 mm, but it will be appreciated that dilators are not restricted to these sizes. It will be appreciated that the number of dilators used during the expand path step 274, as shown in FIG. 2B, can vary between two to five or more. In certain embodiments, a size of the oblique paths 703 is expanded to 10 mm in diameter, so as to expand the SI joint and allow entry of appropriate medical instruments used during the expand joint space step 276, decortication step 277, and pack graft material step 279, as shown in FIG. 2B. However, it will be appreciated that the size is not restricted to 10 mm, as other sizes, such as less than, or greater than 8 mm, 9 mm, 10 mm, 11 mm, 12 mm, 13 mm, and 14 mm may be used in embodiments of the invention.

In certain embodiments, methods, actions, and instruments associated with a deliver access portal step 275, shown in FIG. 2B, is similar to as described for step 215 shown in FIG. 2A, where one or more paths 703 from the exterior of the patient's body to the SI joint are established, as shown in FIG. 18A and FIG. 18B. In certain embodiments, methods, actions, and instruments associated with an expand joint space step 276 and the decortication step 277, shown in FIG. 2B are similar to as described for steps 216 and 217 shown in FIG. 2A. In such steps 276 and 277, an SI joint space is expanded, and fibrocartilage and hyaline cartilage located in the SI joint are removed. In certain embodiments, methods, actions, and instruments associated with a pack graft material step 279, shown in FIG. 2B is similar to as described for step 219 shown in FIG. 2A. In such step, graft material is placed into the SI joint space. In certain embodiments, methods, actions, and instruments associated with a repeat fusion approach step 280 shown in FIG. 2B is similar to step 220 shown in FIG. 2A.

Steps Associated with Securing an SI Joint with a Stabilizer Device

It will be appreciated that the procedure, methods, instruments, and techniques used in step 203 shown in FIG. 2A may also be used for step 254 shown in FIG. 2B to perform certain embodiments of a transsacral bilateral sacroiliac fusion approach. In certain embodiments, such step 254 includes, but not is not limited to the following sub-steps: 1) drill step 281; 2) insert stabilizer device step 282; and 3) verify position step 283.

Steps Associated with Securing SI Joints with a Bilateral Device

Referring to FIG. 2B, in certain embodiments, a secure SI joints with bilateral device step 255 includes, but is not limited to the following sub-steps: 1) insert bilateral device step 284; and 2) verify bilateral device position step 285. In certain embodiments, step 284 uses a number of processes, methods, instruments, and techniques, to secure a bilateral device across two SI joints. Such processes may incorporate, for example, opening, drilling, penetrating, piercing, boring, expanding, an opening across the pelvis. In certain embodiments, step 285 incorporates using a imaging a bilateral device on a patient as to ensure proper placement. Radiographic images taken during such step 285 may include, but is not limited to an oblique view, lateral view, inlet view, and outlet views.

Advantages

In the case of a bilateral sacroiliac fusion approach, there are benefits of approaching an SI joint from three approaches, including, such as a "stabilizer device approach," "bilateral device approach," and the "decortication approach." Typical procedures found in the prior art, such as that described in U.S. Pat. No. 8,734,462 B2, rely solely on the use of one general approach for the purposes of securing the ilium to the sacrum with leading to a variety of suboptimal results. While a singular stabilizer device may be used in association with alternative embodiments of the inventive subject matter, embodiments of the transsacral bilateral sacroiliac fusion approach further incorporates the use of one or more stabilizer devices and one or more bilateral devices. By using one or more stabilizer device in combination with a bilateral device in certain embodiment, the surgical procedure ensures that both a left SI joint and a right SI joint are completely stabilized after surgery. In certain situations, patients may require stabilization of both SI joints. Certain embodiments of a transsacral bilateral sacroiliac fusion approach allows securing both SI joints in a single procedure.

Moreover, access to the SI joint using on or more oblique paths, in certain embodiments of the invention allows effective decortication of articular surfaces associated with an ilium and sacrum at an SI joint, and further allows placement of bone fusion material to such space. Bone fusion material, or graft material, as referred to herein, may include morselized autograft or allograft bone matter that facilitates bone fusion. Bone fusion material may include one or more of other biological substances that aid in bone fusion, including, but not limited to bone marrow, plasma, bone cement, calcium phosphate, xenograft bone, stem cells, and human growth factors.

Unlike several prior art procedures and methods, which may fall short in terms of sufficient placement of bone fusion material in an SI joint, certain embodiments of the invention facilitate the deep placement of bone fusion material within the SI joint. Certain embodiments of the invention provides access to a SI joint space through one or more oblique paths, allowing articular surfaces to be cleaned and/or decorticated by a medical practitioner using a variety of decortication tools and mechanisms. Effective decortication is an important aspect of the preferred embodiment of the invention, as decortication prepares a large bone surface area within the SI joint space to allow bone fusion. The large surface area facilitates the increased stability of the SI joint area once the bone is fused and healed, further minimizing the risks of destabilization of an SI joint, or destabilization of a stabilization device and/or bilateral device located in an SI joint after healing. In certain cases, risk of pseudarthrosis and other complications may be decreased by accessing an SI joint space. A number of benefits derive from the combination of the filling of the SI joint space with graft material, and the compression of the SI joint with screws, as described herein. The compression of an ilium and sacrum using stabilizer devices and/or bilateral devices facilitates bone fusion, while the stabilizer devices and/or bilateral devices mitigates movement of the ilia in relation to the sacrum while the bone graft heals. The combined approach described herein, therefore, maximizes bone fusion, reduces risk of breakage of instrumentation, and reduces the risk of pseudarthrosis and other related complications, solving a number of problems associated with some prior art methods.

Apparatuses Associated with Certain Embodiments of the Methods

It will be appreciated that certain embodiments of the devices disclosed herein are used for embodiments of a sacroiliac fusion approach and/or a transsacral bilateral sacroiliac fusion approach, for example, as shown in FIG. 2A and FIG. 2B. It will be appreciated that certain methods, steps, techniques, and approaches described here use a stabilizer device, or both a stabilizer device and a bilateral device. It will also be appreciated that certain methods, steps, techniques, and approaches are not limited to using a device as described here, and a device generally traversing bone to join such bone, for example, facet screws, pedicle screws, or rods, of various sizes and shapes that can span between an ilium and sacrum may be useful, or used with a bilateral device.

Stabilizer (Unilateral) Device

Generally, in certain embodiments of the invention, a stabilizer device 2101 follows one or more stabilizer device paths 701 as determined during steps 201, 251, as shown in FIG. 2A and FIG. 2B, for example. One or more stabilizer devices are inserted across an SI joint during steps 222, 282, as shown in FIG. 2A and FIG. 2B. In general, certain embodiments of a stabilizer device compress an SI joint to stabilize the joint, and so that bone growth is promoted in graft material packed into the SI joint.

Figure 13A:
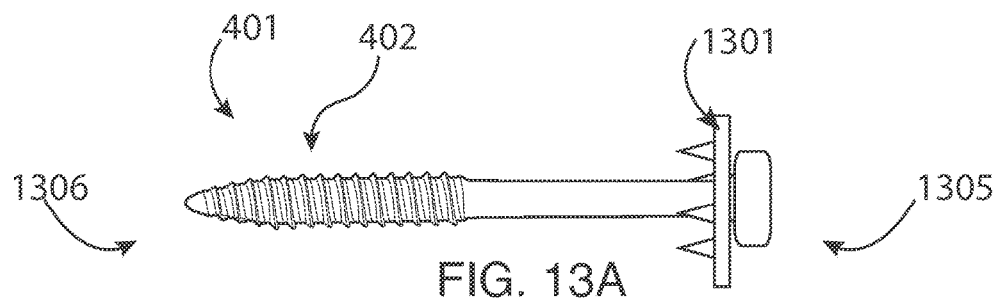
FIG. 13A. A side view of an embodiment of a stabilizer device with a washer.
Figure 13B:
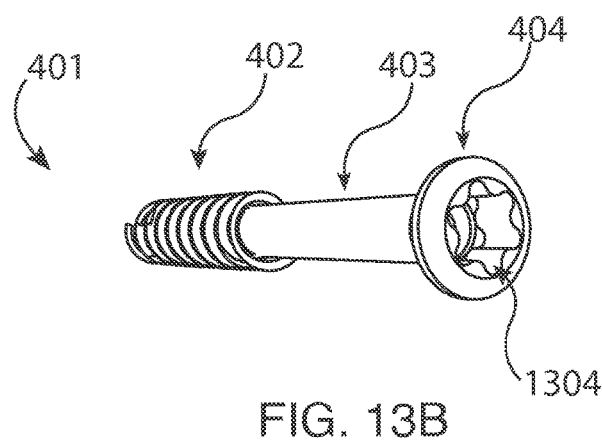
FIG. 13B. A perspective view of an embodiment of a stabilizer device.
Figure 13C:
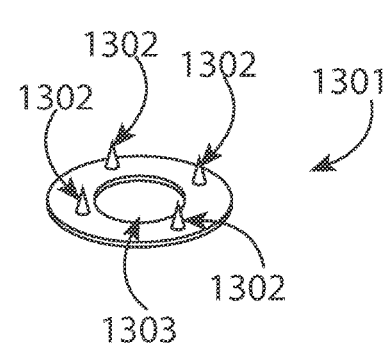
FIG. 13C. A perspective view of an embodiment of a washer.
Figure 13D:
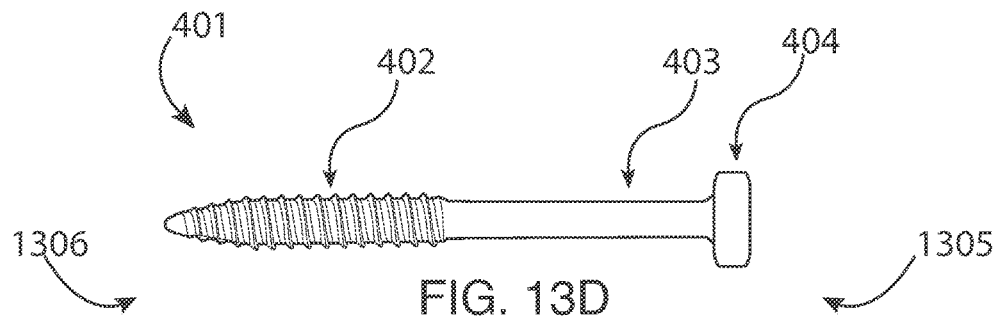
FIG. 13D. A side view of an embodiment of a stabilizer device.

In certain embodiments of the invention, a stabilizer device 2101, as shown in examples FIG. 21A and FIG. 13D may be used for the sacroiliac fusion approach. An embodiment of the stabilizer device 2101 has a thread 2102, as shown in an example in FIG. 21A, where the thread 2102 is a helical ridge to advance such stabilizer device 2101 through anatomical and cellular structures including, but not limited to bone, tissue, and cartilage, by rotating such stabilizer device around its longitudinal axis. One embodiment of a stabilizer device 2101 or 1306 as shown in examples FIG. 21A FIG. 13B, and FIG. 13D, has a shank 2103, 403 lacking a thread feature. It will be appreciated that in certain embodiments, a stabilizer device lacks a shank region. In certain embodiments, a stabilizer device has more than one shank. An embodiment of a stabilizer device 2101, 1306 has a head 2104, 404 as shown in examples FIG. 21A, FIG. 21B, and FIG. 13D such head having a drive 1304 as shown in example FIG. 13B. A user may use a driver having a mating portion to a drive 1304 to apply axial rotation to a stabilizer device 2101, 1306 to advance through bone. An embodiment of a stabilizer device 2101, 1306 further has an opening 2105 located along its longitudinal axis, as illustrated in the cross-sectional view of a stabilizer device embodiment shown in example FIG. 21B.

As shown in example FIG. 20C of a cross-sectional view of a left SI joint region for securing the a left SI joint, a stabilizer device 2101 secures the left ilium 102 and the sacrum 101 by entering through the left ilium 102 into the left sacral ala 122. As shown in example FIG. 20C, certain embodiments of a stabilizer device 2101 may be secured with a sheath 2201. A sheath 2201, in certain embodiments, is a cylindrical form that has an opening 2205 and accommodates a diameter of a stabilizer device 2101, as shown in example FIG. 22A. Certain embodiments of a sheath has a lip 2202 having a wider opening at one end of such sheath, that accommodates a head 2104 of the stabilizer device 2101, as illustrated in the embodiment in FIG. 20C. In certain embodiments, a sheath 2201 is placed within the bony structure of the left ilium 102, which may further include cortical bone 2002 and cancellous bone 2003 as illustrated in FIG. 20C. A stabilizer device 2101 is placed through an opening 2205 of the sheath 2201, as shown in FIG. 20C, where a thread 2102 of a stabilizer device 2101 may engage with bony structures including cortical bone 2005, cancellous bone 2004, and/or graft material 2005, such graft material 2005 placed between an ilium 102 and sacrum 101 in other steps (202 and 253, as in FIG. 2A and FIG. 2B) in certain embodiments of the invention.

Figure 13E:
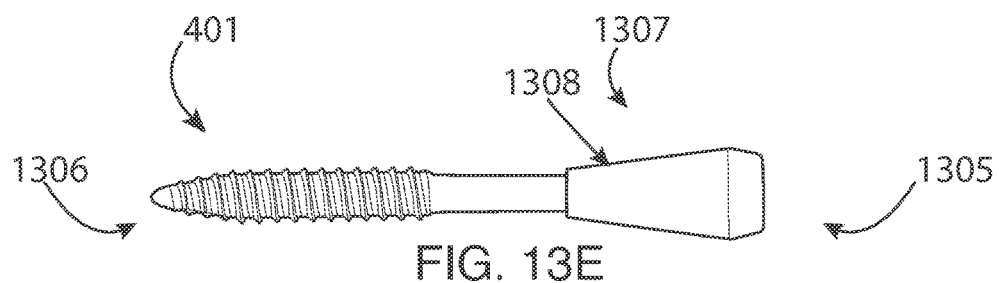
FIG. 13E. A side view of an embodiment of a stabilizer device and a sheath.
Figure 22A:
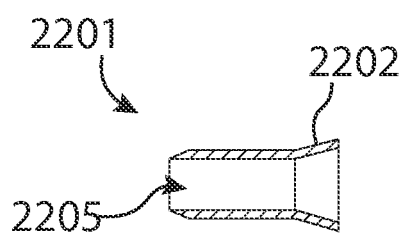
FIG. 22A. A side, cross-sectional view of an embodiment of a sheath.
Figure 22C:
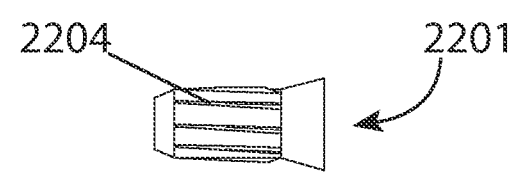
FIG. 22C. A side view of an embodiment of a sheath.
Figure 22B:
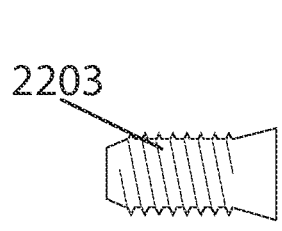
FIG. 22B. A side view of an embodiment of a sheath.
Figure 22D:
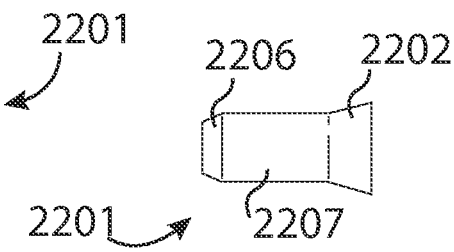
FIG. 22D. A side view of an embodiment of a sheath.

In certain embodiments of the invention, the sheath 2201 further has an external surface that stabilizes such sheath within osseous tissue. For instance, in an embodiment of the invention shown in FIG. 22B, a sheath 2201 has a thread 2203 that engages with bone of the ilium. The direction of such thread 2203 may have a direction that is the same as thread of a stabilizer device, or may be in an opposite direction. In certain embodiments, a thread 2203 may have the same or different pitch as that found on a stabilizer device. In other embodiments of the invention, the sheath 2201 has a wedge feature 2204, as illustrated in FIG. 22C. The wedge feature 2204, for example, includes splined features along a length of a sheath 2201, that allows such sheath to be secured within the bone opening by providing tension between the bone and the sheath as such sheath is pounded or tapped into the bone opening. In certain embodiments, a sheath has a smooth surface 2207, as shown in FIG. 22D. In certain embodiments, a sheath 2201 has a chamfered edge 2206 that allows easier entry into bone, as shown in example FIG. 22D. In certain embodiments, as shown in example FIG. 13E, a sheath 1307 has a bevel 1308.

In general, in certain embodiments, a shank 2103 and thread 2102 of a stabilizer device 2101 are different lengths. The cortical bone 2002 of an ilium 102 where a stabilizer device 2101 enters, as shown in example FIG. 20C, may have a thickness between 3 mm and 8 mm, and the thickness of cancellous bone 2003 may be between 8 mm and 12 mm, depending on a patient. In certain cases, the thickness of the cortical bone 2002 may be less than 3 mm or greater than 8 mm, and cancellous bone 2003 may be less than 8 mm or greater than 12 mm. Again, the thickness of cortical bone or cancellous bone that certain embodiments of the stabilizer device must pass, is typically dependent on the anatomical structure of a patient, and specific entry angle of a stabilizer device path 701. The iliac bone, in which a stabilizer device 2101 traverses through a stabilizer device path 701 has, in general, a total thickness between 15 mm and 25 mm, although it may have a thickness less than 15 mm and greater than 25 mm; generally, such path includes passing two layers of cortical bone 2002 and a layer of cancellous bone 2003. In embodiments of the invention, the length of a shank 2103 of a stabilizer device 2101 corresponds to the thickness of an iliac bone, for example, between 15 and 25 mm in length. In certain embodiments, a shank 2103 is 20 mm in length. It will be appreciated that certain embodiments of a stabilizer device 2101, as shown in example FIG. 20C, has a shank 2103 that corresponds generally to the thickness of an ilium.

In certain embodiments the length of a thread 2102 of a stabilizer device 2101 is dependent on the thickness of the sacral ala at a specific portion of a patient's body. As illustrated in examples FIG. 4A, and FIG. 4B, a plurality of stabilizer device paths 701 may be established to stabilize the ilium and the sacrum in certain embodiments of the invention. Variations in the thickness of the bone of the sacral ala exist within a patient and among different patients. In general, the sacral ala has cortical bone 2005 that is between 3 mm and 8 mm in thickness, and cancellous bone 2004 that is between 10 mm and 35 mm in thickness, as shown in example FIG. 20C. It will be appreciated that in some patients, such cortical bone 2005 may have a thickness less than 3 mm, or greater than 8 mm. It will also be appreciated that such cancellous bone 2004 has a thickness less than 10 mm or greater than 35 mm. Furthermore, the thickness of the SI joint may vary between 0 mm to 2 mm, or 2 to 12 mm, or more. Therefore, a thread 2102 of a stabilizer device 2101, shown in example FIG. 21A having a length that is between 10 and 60 mm is appropriate for screwing into the sacral ala for the purposes of stabilizing the ilium and sacrum, in certain embodiments. In certain embodiments, a stabilizer device 2101 having threads 2102 that are of various lengths, for example, 5 mm, 10 mm, 20 mm, 30 mm, 40 mm, and 50 mm, allows a medical practitioner to select an appropriate screw for specific patients or procedures. It will be appreciated that, a number of other lengths for the thread 2102 or shank 2103 of a stabilizer device 2101 may be used in certain embodiments of the invention.

In certain embodiments, a stabilizer device 401, as illustrated in example FIG. 13A uses a washer 1301, as illustrated in examples FIG. 13A and FIG. 13C. As shown in example FIG. 13C, a washer 1301 has an opening 1303, that accommodates a portion of a stabilizer device 2101. In a certain embodiment, shown in FIG. 13C, such washer has teeth 1302 that interfaces with the external structure of bone, such teeth 1302 having sharpened and/or protruding features that grip bone, so that a proximal end 1305 is stabilized while a distal end 1306 is further screwed into bone.

In certain embodiments of the invention, a stabilizer device (and bilateral device) has a self-harvesting feature designed to harvest bone material as it traverses the ilium and/or sacrum. Such stabilizer device with a self-harvesting feature in the preferred embodiment incorporates a helical groove running along a portion of the length of the screw. An embodiment of such stabilizer device features an angular contact area designed to collect bone. The collected bone occupies a void within the stabilizer device in the preferred embodiment. The bone therefore can fuse directly with bony tissue of the sacrum and ilium after the stabilizer device is implanted during the post surgical healing process. Resultantly, the present inventor has noted that the fused bone in, through and/or around the stabilizer device assists in the long term fixation of the stabilizer device, preventing loosening and/or backing out of the stabilizer device from the sacrum and ilium.

Figure 34:
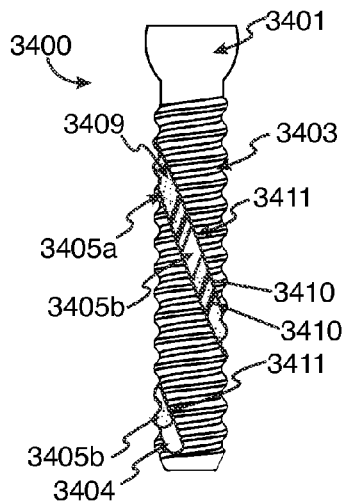
FIG. 34. A side view of a stabilizer device incorporating a self-harvesting feature in certain embodiments.

To further illustrate the embodiment of the stabilizer device featuring a self-harvesting feature, FIG. 34 depicts a stabilizer device 3400 comprising a helical opening, such as helical opening 3405a and 3405b, together creating a double helical groove within a thread 3403 section. In certain embodiments, a head 3401 has a drive that allows axial rotation of the device with a drier. In certain embodiments, a helical opening has a cutting edge 3411, where turning the stabilizer device through bone causes surrounding bone to be cut and/or shaved. Such cut or shaved bone is further incorporated in an cavity 3409, essentially allowing such device to harvest bone while driving. Certain embodiments of the stabilizer device feature threading and grooves that cause the harvested bone to be redirected into the space between the sacrum and ilium to aid in fusion of the sacrum and ilium. In certain embodiments, a spline located along an internal wall for example, a spline 3410 running helically in a device, further assists in acting to redistribute cut bone material. In certain embodiments, a stabilizer device incorporates a groove 3404, such groove found on a distal end of a helical opening 3405b, for example, as shown in FIG. 34. It will be appreciated by those skilled in the art to incorporate a self-harvesting feature can be found on a threaded and/or shaft portion of a bilateral device.

In certain embodiments, a stabilizer device 2400 resembles a shaft. A stabilizer device 2400, as shown in FIG. 24A, FIG. 24C, and FIG. 24D has two threaded features, for example, a distal threaded feature 2402 and a proximal threaded feature 2401. A threaded feature 2402 on a distal end is intended to engage with cortical and/or cancellous bone layers of the sacrum, while a proximally located threaded feature 2401 is intended to engage with cortical and/or cancellous layers of bone of an ilium. In certain embodiments, the proximal threaded feature 2401 and distal threaded feature 2402 exhibit differing thread pitches such that the thread pitch of a threaded feature of the distal end is a coarser pitch than a threaded feature of the proximal end. Such differing thread pitches serves to advance the distal threaded section at a higher distance-advanced per rotation rate than that of the proximal end, causing a compressing effect between the sacrum and ilium and compressing a SI joint. In certain embodiments, it may be preferred to configure the distal threaded feature to exhibit a smaller diameter than that of the proximal threaded feature. The differing thread pitches may vary from embodiment to embodiment to allow compression of a prescribed amount.

In certain embodiments, as shown in FIG. 24A, FIG. 24C, and FIG. 24D a stabilizer device 2400 has a section between the proximal threaded section 2401 and the distal threaded section 2402 devoid of threading, referred to herein as a shank 2403, typically exhibiting a diameter equal to or less than the major thread diameter of a proximal threaded feature. The shank 2403, in such embodiments typically exhibits a diameter less than that of the major diameter of the thread pitch of the proximal threaded feature. Specifically, the shank is configured to be less than the diameter of a tap-drill for the proximal threaded section. Further, it may be preferred to configure a shank to exhibit a diameter such that it provides an engineering fit in the same hole sized for a tap-drill for the proximal threaded section. This engineering fit may be determined by an administering medical practitioner and the tap diameter selected based on engineering fits. It will be appreciated to one skilled in the art that an engineering fit includes, but is not limited to, a location fit, a clearance fit, a sliding fit, transition fit, interference fit and/or a running fit. In a variation of such an embodiment the proximal thread section typically has a major diameter of 15 mm or less.

In an embodiment of a stabilizer device the proximal threaded portion has diameter of 10 mm and minor diameter of 8 mm, shank diameter of 8 mm, and distal threaded section major diameter of 7.75 mm. In this embodiment the proximal thread section has axial length of 10 mm with thread pitch providing 1.8 mm of travel per rotation and the distal threaded section has length of 16 mm with thread pitch of 2.0 mm per revolution and overall device length of 42 mm. In such an embodiment the thread pitch differential would provide compression at a rate of 0.2 mm per revolution. It may be desired to prepare the pathway for a locational clearance fit in relation to the shank diameter. As defined by the International Organization for Standardization (ISO), this would indicate the use of a 8.015 mm tap drill. It will be appreciated that a tap drill is a drill used to prepare a pathway for the installation of a threaded device. The threaded device may be installed with no further preparation of the pathway or following additional steps to prepare the pathway such as the use of a tap, used to cut screw threads into the interior surface of the prepared pathway. A medical practitioner may elect to use such standards as defined by ISO, the American Society of Mechanical Engineers (ASME) or an alternate sizing basis.

It may be further preferred for at least one threaded section to have a taper wherein the proximal end of a threaded section is of larger diameter than that of the distal end of the same threaded section.

Figure 33:
FIG. 33. A side view of a stabilizer device in certain embodiments.

Alternately, it may be preferred that a shank is configured to be less than the diameter of a tap-drill for the distal threaded section. Further, it may be preferred to configure a shank to exhibit a diameter such that it provides a clearance or sliding fit in the same hole sized for a tap-drill for the distal threaded section, for example, as shown in FIG. 33.

Figure 32A:
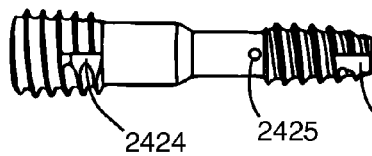
FIG. 32A. A side view of a stabilizer device in certain embodiments.
Figure 32B:
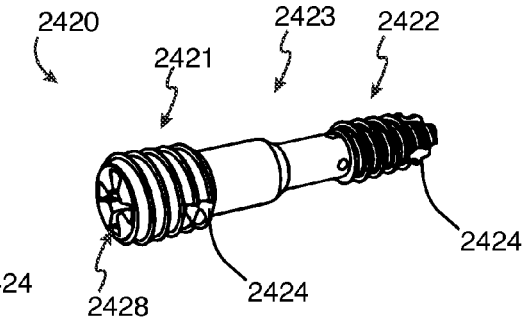
FIG. 32B. A perspective view of a stabilizer device in certain embodiments.
Figure 32C:
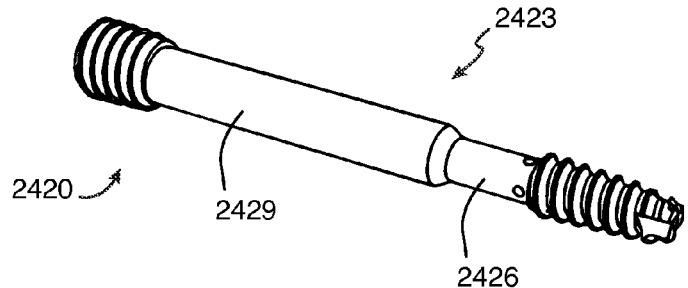
FIG. 32C. A perspective view of a stabilizer device in certain embodiments.

In yet another alternative, it may be preferred that a shank comprises a major diameter section and a minor diameter section. As shown in FIG. 32A, a major diameter section 2429 located toward the proximal end of the shank 2423 and the minor diameter 2426 located toward the distal section of the shank 2423 with the length of the major diameter section typically comprising a longer length of the shank than that of the minor diameter section. This allows a larger distal threaded section to be employed with less impingement within the prepared pathway prior to engagement into the intended bony structure.

The preparation of the joint space for the installation of such an apparatus involves the use of a drill to create a path that follows a guide wire, as in steps 221 or 281 as shown in FIG. 2A or FIG. 2B, wherein a drill uses a step drill with at least two diameters or a series of drills or drill bits to create a pathway with a plurality of diameters for the installation of the stabilizer device.

Certain embodiments of an apparatus 2400 or 2420 as shown in FIG. 24A, FIG. 24C, FIG. 24D, FIG. 32A, FIG. 32B, and FIG. 32C having a distal threaded feature 2402, 2422 and a proximal threaded feature 2401, 2421 separated by a shank 2403, 2423 further has a self-tapping feature 2404, 2424, for instance, on a distal threaded section 2402 as shown for example in FIG. 24C. It will be appreciated that in certain embodiments, a self-tapping feature 2424 may also be found on a proximal threaded section 2421. In certain embodiments, a self-tapping feature on a distal threaded section and/or proximal threaded sections of the screw cut their own threads into bone when rotated to engage the bone structure of the ilium and/or the sacrum.

It will be appreciated by those skilled in the art that a self-tapping feature may comprise features such as, but not limited to, a gimlet, flute or slot. It will be further appreciated that such self-tapping features may be used singularly or in plurality and may be localized to a portion of a screw, such as the tip, may extend through the length of the apparatus or an intermediate length.

In certain embodiments, one or more self-tapping feature 2404 may be located on a section 2401 or section 2402, for example three such self-tapping features on a distal threaded feature 2402 as shown in FIG. 24C.

Certain embodiments an apparatus with differing thread pitches may include features to assist in verifying the stabilizer device position when placed in a patient. These features may include apertures 2405 or 2425 located through a diameter 2406 of such stabilizing apparatus 2400, for example, at a proximal end 2409 of the distal threaded feature 2402 as shown for example in FIG. 24B, as to verify the location of the stabilizer device in relation to the SI joint space, through the use of radiography, or other methods of radio-imaging. In certain embodiments, more than one aperture 2425 may be placed on a minor diameter 2426, as shown in for example FIG. 32A and FIG. 32D, or on a major diameter 2429.

Certain embodiments of this invention include alternative lengths allows for the selection of a desired length of stabilizer apparatus per patient use. To establish the length of device required, the medical professional is required to determine the depth of the proximal cortical bone structure of the ilium from a reference, typically the skin surface. During the process of the preparation of the pathway, for example, during steps 201 or 251, as in FIG. 2A or FIG. 2B an administering medical professional determines the distance between the outer cortical bone at the proximal surface of the ilium and the distal end of a trephine needle or guide wire. Determining such distance provides the maximum depth of a stabilizer device to implant into the prepared pathway, however, typically it is desired to select a device at least 5 mm shorter than the distance between the outer cortical bone and the most proximal sacral foramen. After the pathway for the stabilizer device has been prepared in the drill step 221 or 281, an administering medical professional measures the distance from the proximal surface of the ilium and the distal$_{[1]}$ end of a trephine needle or guide wire, which represents the distal end of the prepared pathway for the apparatus.

Figure 32D:
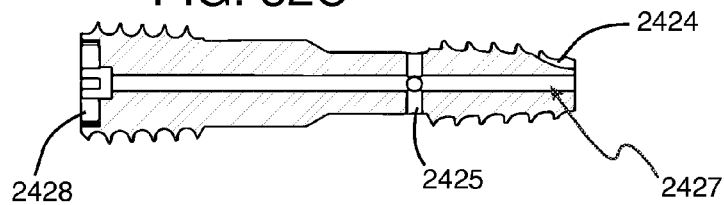
FIG. 32D. A side, cross-sectional view of a stabilizer device in certain embodiments.

When inserting a device, for example as represented by steps 222 or 282 in FIG. 2A and FIG. 2B, a medical professional inserts a device, for example device 2400 or 2420 having a central opening 2407 or 2427 as shown for example in FIG. 24B, or FIG. 32D over a guide wire until the device cannot be advanced further without axial rotation. The medical professional then further advances the device through axial rotation, thereby engaging the threads within the bone structure. In certain embodiments, a device 2400 or 2428 has a drive 2408 or 2428 as shown, for example, in FIG. 24B, FIG. 24D, FIG. 32B, and FIG. 32D that allows such axial rotation with a driver. As shown, for example, in FIG. 24E, the device 2400 is advanced until the proximal threaded feature 2401 is engaged with the outer proximal cortex 2410 of the ilium 102, and a distal threaded feature 2402 is engaged with the sacrum 101, for example, cortical bone 2411, and has provided the desired amount of compression to a joint space 104. Through the use of radiography, a medical professional confirms the distal threaded section is completely within the sacrum and not engaged with the ilium or within the SI joint space.

Bilateral Devices

A bilateral device, or bridging stabilizer device in certain embodiments of the invention is, in general, an oblong shape having a securement means for the purposes of securing the left ilium 102, the right ilium 103, and the sacrum 101, as well as compressing the left SI joint 104 and the right SI joint 105 as to minimize pain associated with sacroiliitis and other afflictions related to a loosened SI joint. In certain embodiments, a bilateral device is inserted into a patient through an access portal. It will be appreciated that an access portal can be established through the transsacral approach, on both the left and right side, during, and after step 252 as shown in FIG. 2B.

It will be appreciated that a number of different sizes can be used to stabilize the sacrum and ilia across a transsacral approach. It will be appreciated that generally, the length of the bilateral device in embodiments of the invention may vary as to accommodate the pelvises found in various patients, where certain embodiments may have length that is between 4 inches and 20 inches across, although other embodiments can be shorter or longer. Furthermore, a width of the bilateral device in embodiments of the invention may vary as to accommodate the varying thickness of the S1 vertebral body found in various patients, where certain embodiments have a width that is between 4 mm and 10 mm, although other embodiments can be smaller or larger.

It will be appreciated that the mechanism of securement for the bilateral device is not limited to the embodiments as discussed herein, where certain embodiments of the bilateral device functions to introduce a compressive force transsacrally. It will be appreciated that a number of different views, particularly an oblique view, lateral view, inlet view, outlet view, or others, may be referenced while performing the examples disclosed, as to for example, determining the location, position, orientation, or degree of compression of certain embodiments of the bilateral devices. In certain embodiments, verifying the position of a bilateral device is performed during step 285, as shown in FIG. 2B. It will also be appreciated that a number of features, components, and other disclosures can be used together, in combination with, or in place of other features disclosed in the examples below. It will be appreciated that certain steps, methods, procedures, and techniques as described in the examples below may be performed during step 284, as shown in FIG. 2B. It will also be appreciated that embodiments of the invention can use a bilateral device in combination with a stabilizer device as to accomplish effective stabilization of the SI joint or SI joints.

Example 1

During the secure SI joint with bilateral device step 255, a medical practitioner inserts a bilateral device into the bilateral device path 702, as to secure a left ilium 102, the right ilium 103, and the sacrum 101, and further compressing the left SI joint 104 and the right SI joint 105 as to minimize pain associated with sacroilitis and other afflictions related to a loosened SI joint or SI joints. In certain embodiments, a bilateral device compresses a left ilium, right ilium, and sacrum to ensure that both ilia are secured simultaneously. In certain embodiments of the invention, stabilizer devices further secure individual ilia to the respective side of a sacrum.

Figure 23A:
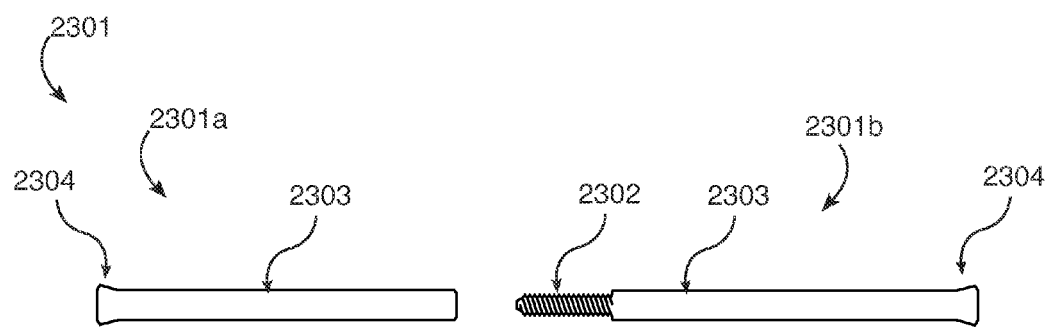
FIG. 23A. An embodiment of a bilateral device.
Figure 23B:
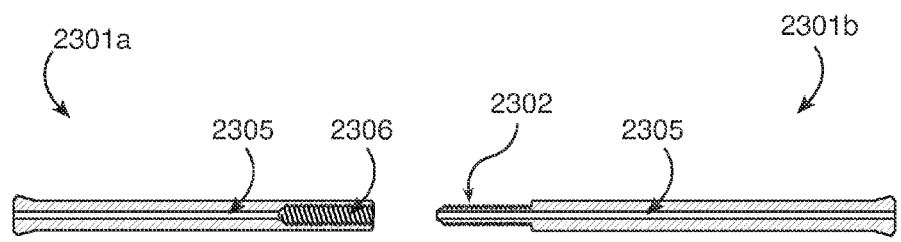
FIG. 23B. Cross-sectional view of an embodiment of a bilateral device.

An embodiment of a bilateral device is shown in FIG. 23A, where the bilateral device 2301 further comprises two components. In certain embodiments, a first component 2301a joins with a second component 2301b. In one embodiment of the invention, the first component 2301a is secured to second component 2301b with a male thread 2302 and a corresponding female thread 2306, wherein axial rotation of a first component 2301a with a female thread 2306 and a second component 2301b with a male thread 2302 allows engagement of the components. Certain embodiments of the bilateral device 2301 further has an axial opening 2305, as shown for example in FIG. 23B, where such opening 2305 may be used to follow a guide wire. Certain embodiments of a bilateral device 2301 additionally have a smooth shank 2303 region. Certain embodiments of the invention may have a shank that is cylindrical, or other shapes, including but not limited to triangular prisms, cuboid.

In general, embodiments of the bilateral device 2301 has a head 2304, where a head 2304 of a first component 2301a and a head 2304 of a second component 2301b has a drive that allows engaging with a driver to allow a medical practitioner to apply an axial rotation. In embodiments of the invention, a head may have, but is not limited to a uni-axial, poly-axial joint, ball joint, or otherwise movable joint, allowing the head to move independently from the axis of the rest of a screw, for example, a first component 2301a and/or the second component 2301b. In certain situations, a movable head, for example, a poly axial joint, allows the head to be adapted to the curvature and/or angles associated with a surface of an ilium.

Example 2

In certain embodiments, a bilateral device may have an oblong component that traverses the sacrum. In certain embodiments, a bilateral device may have an oblong component having a feature at one end. In one example, a bilateral device 2500 comprises a component 2502 or 2516, a floating screw 2501, and an end screw 2509, as shown in examples FIG. 25A, FIG. 25B, FIG. 25E, FIG. 25G, and FIG. 2511. In certain embodiments, a component 2502 further has a threaded head 2506 and a shaft 2507, as shown in the example in FIG. 25B. Certain embodiments of an end screw 2509, as shown in the example in FIG. 25E, fastens a floating screw 2501 to a female thread 2505 located on one end of a component 2502, 2516, as shown in an example in FIG. 25C, FIG. 25D, and FIG. 25G. A floating screw 2501, as shown in FIG. 25F, may also have drive 2514 that can allow axial rotation of such screw 2501 with a driver as well as accommodating a diameter of an end screw head 2512, and further have an smaller diameter axial recess 2515 that can accommodate a diameter of a thread region 2513 of such screw 2509. In certain embodiments, an end screw 2509, as shown in FIG. 25E, has an axial opening 2510 that may be slide over a guide wire. In certain embodiments, a component 2516 has a smooth head 2508 lacking threading.

In an example of securing a bilateral device, a medical practitioner uses a drill bit having a diameter large enough to accommodate a diameter of a component shaft. A guide wire transsacrally established after step 270, as shown in FIG. 2B, may be used to guide a drill. A medical practitioner drills through a first ilium (proximal region), through a sacrum, and through a second ilium (distal region). Following such steps, a drill bit having a diameter large enough to accommodate a floating screw 2501 may be used to drill preferably one, or both cortical bone layers of a distally located ilium. Embodiments of a component 2502 or 2516 have an axial opening 2504, as shown in examples in FIG. 25C and FIG. 25D, as to pass such component over a guide wire, where such guide wire is, for example, established after step 270 as shown in FIG. 2B. In an embodiment, a component 2516 is advanced through a transsacral space over a guide wire until its head 2508 reaches a cortical bone of a proximally located ilium. A floating screw 2501 is then driven into preferably one, or both cortical bone layers of a distally located ilium using a driver. Subsequently, at the distal region, an end screw 2509 is passed over a guide wire through its opening 2510. Using a driver engaging with a drive 2511, such screw 2509 is axially rotates whereby its thread 2513 passes through features 2514 and 2515 of a floating screw 2501, and such thread 2513 further engages with a female threading 2505 located on a component 2516. Such action causes the proximally located ilium pressed against a head 2508 of a component 2516, and a distally located ilium that has a screw 2501 engaged with the distally located ilium, to compress, thereby stabilizing both joints.

In another example of securing a bilateral device, a medical practitioner uses a drill bit having a diameter large enough to accommodate a diameter of a shaft. A guide wire established after step 270, as shown in FIG. 2B, may be used to guide a drill bit. A medical practitioner drills through a first ilium (proximal region), through a sacrum, and through a second ilium (distal region). Following such steps, a drill bit having a diameter large enough to accommodate a floating screw 2501 may be used to drill preferably one, or both cortical bone layers of a distally located ilium, as well as to drill preferably one, or both cortical bone layers of a proximally located ilium. A component 2502 is advanced over a guide wire until its head 2506 reaches a cortical bone of a proximally located ilium. A driver is then engaged with a drive 2517 to axially rotate such component 2502 through a proximally located ilium. A floating screw 2501 is then driven into preferably one, or both cortical bone layers of a distally located ilium using a driver. Subsequently, at the distal region, an end screw 2509 is passed over a guide wire through its opening 2510. Using a driver engaging with a drive 2511, such screw 2509 is axially rotates whereby its thread 2513 passes through features 2514 and 2515 of a floating screw 2501, and such thread 2513 further engages with a female threading 2505 located on a component 2502. Such action causes the proximally located ilium that has a head 2506 driven in, and a distally located ilium that has a screw 2501 driven in, to compress, thereby stabilizing both joints.

In certain embodiments, a component 2502 or 2516 is available in a number of sizes, such as for example variations in a length region of a shaft, allowing a medical practitioner to choose an appropriate size depending on the anatomy of a patient. Certain embodiments of the invention have one or more aperture 2503 located on a shaft of a bilateral device, such aperture having or lacking features that can be detected using an imaging device (for example, such aperture that shows as an indicator in a radiographic image), thereby allowing a medical practitioner to determine the depth or location of such bilateral device using radiography by determining the location of such aperture. In certain embodiments, a trial may be used to gauge the distance between a first ilium to a second ilium, where such trial may also have apertures that allows visualization with an imaging device.

Example 3

In certain embodiments, a bilateral device comprises an oblong component, which can have features fastened, attached, threaded, fitted, on both sides of such component. In certain embodiments, a bilateral device 2520 comprises a component 2521 having an oblong shape, as shown in an example in FIG. 6A, FIG. 26B, further having threads 2523 (shown for example in FIG. 25D) on both ends. In certain embodiments a shaft region, for example, shaft 2527 (also, for example, on component 2541) comprises a spline 2524 running in a longitudinal direction, as shown in for example, FIG. 26C. A plurality of splines 2524 may be arranged circumferentially along such shaft, forming one or more grooves 2525, as shown in example FIG. 26C, FIG. 30C. Certain embodiments of a component has an axial opening 2526 or 2574, as shown in example FIG. 26C or FIG. 31G, that allows a medical practitioner to slide a component over, for example, a guide wire.

In certain embodiments, a wedge end screw 2522, further shown in the examples FIG. 26A, FIG. 27A, FIG. 27B, and FIG. 27C, has an opening 2530 that accommodates a guide wire and parts of a component, for example, a thread 2523 of a component 2521. As shown in an example FIG. 27C, a screw 2522 has a female thread 2532 that engages with a male thread 2523. A drive 2528 located on one end of a screw 2522, as shown in examples FIG. 27A, FIG. 27B, and FIG. 27C, allows a medical practitioner to use a driver to axially rotate the screw. In certain embodiments, a screw 2522 has a recess 2531 that can accommodate a portion of a shaft (for example, shaft 2527) of a component (for example, component 2521). In certain embodiments, a screw 2522 has a wedged surface 2531, as shown in FIG. 27A, where such wedge allows an interference fit with bone as the screw is tightened, allowing for compression between a bilateral device.

Certain embodiments of a screw 2522 has one or more longitudinal through hole 2529, as shown in examples FIG. 27B and FIG. 27C. It will be appreciated that embodiments of a screw may have preferably two through holes, although generally, one or more through holes may be used in certain embodiments. In certain embodiments, the purpose of a through hole is to allow a locking pin, for instance, a locking pin 2534 having two ends 2535 as shown in example FIG. 28A, to pass. As further shown in the example in FIG. 28A, a first end 2535 passes through a through hole 2529 of a screw 2522, and along a groove 2525 (i.e. between two splines 2527), as further shown in FIG. 28B. It is preferable that a screw is engaged with threads of a component, and preferably two screws applying a compressive between two SI joints, before inserting a locking pin. It will be appreciated that in certain embodiments, a screw 2522 may be placed on both ends of a component 2521.

It will be appreciated that one or more splines 2524 located on a component (for example, component 2521, 2541) has at least three advantages. A first advantage is that a groove 2525 formed between two splines can fit an end of a locking pin, thereby preventing unwanted movement of screw, as shown for example in FIG. 28B, FIG. 31A, and FIG. 31I. A second advantage is that the splines, in certain embodiments, prevent unwanted torsional movement of a bilateral device within pelvic bone, for example, by engaging with cortical bone, or cancellous bone found on a left ilium, right ilium, and/or sacrum, and further mitigating certain movements of an ilium relative to a sacrum. A third advantage is that the splines may act as crevice that allows a greater surface area for bone formation, after graft material is placed in the SI joints during embodiments of the invention.

In an example of securing a bilateral device, a medical practitioner uses a drill bit having a diameter that accommodates a shaft (for example, a diameter that is smaller than the diameter comprising a spline). A guide wire established after step 270, as shown in FIG. 2B, may be used to guide a drill bit. A medical practitioner drills through a first ilium (proximal region), through a sacrum, and through a second ilium (distal region). Following such steps, a drill bit having a diameter that accommodates a portion of a wedge end screw 2522 (e.g. FIG. 27A) may be used to drill preferably one, or both cortical bone layers of a distally located ilium, as well as to drill preferably one, or both cortical bone layers of a proximally located ilium. Then, a component 2521 may be inserted through the opening created through a transsacral space following a guide wire, until a thread 2523 of the component reaches the past an SI joint located at the distal region. A medical practitioner may then insert a screw 2522 following a guide wire to a proximal region and distal region of a pelvis, until the threads 2532 of such screws engages with threads 2532 of a component 2521. Using a driver that engages with a drive 2528 on one screw 2522, both screws at a distal region and proximal region may be axially rotated. As the screws are turned, a wedge feature 2531 of a screw creates a compressive force between the proximally located ilium and distally located ilium, further compressing both SI joints between a bilateral device. A locking pin 2534 may further be inserted to lock a screw to a component 2521. In another example of securing a bilateral device, prior to inserting a component 2521 through an opening through a transsacral space, one end of such component 2521 may be pre-installed with a screw 2522.

Example 4

In certain embodiments, a screw placed on both ends of a component 2521 has external threads. As shown in, for example, FIG. 29A, FIG. 29B, and FIG. 29C, a screw 2536 has threads 2537 on an external surface, that engages with portions of bone, for example, cortical bone of an ilium and a sacrum. In certain embodiments, a screw 2536 has an internal female thread 2532 as shown in FIG. 29B, that engages with a male thread 2523 of a component 2521. In certain embodiments, a screw 2536 has an internal female thread 2532 and an external thread 2537 with the same pitch. In certain embodiments, such female thread 2532 and external thread 2537 have different pitches. Certain embodiments of a screw 2536 has a drive 2528, as shown in example FIG. 29B that fits with a driver so that a medical practitioner can axially rotate the screw 2536 through bone. Certain embodiments of a screw 2536 has one or more through holes 2529 oriented in a longitudinal direction, fitting an end 2535 of a locking pin 2534, as shown in an example in FIG. 29C.

In an example of securing a bilateral device, a medical practitioner uses a drill bit having a diameter that accommodates a shaft (for example, a diameter that is smaller than the diameter comprising a spline). A guide wire established after step 270, as shown in FIG. 2B, may be used to guide a drill bit. A medical practitioner drills through a first ilium (proximal region), through a sacrum, and through a second ilium (distal region). Following such steps, a drill bit having a diameter that accommodates a portion of a screw 2536 may be used to drill preferably one, or both cortical bone layers of a distally located ilium, as well as to drill preferably one, or both cortical bone layers of a proximally located ilium. Then, a component 2521 may be inserted through the opening created through a transsacral space following a guide wire, until a thread 2523 of the component reaches the past an SI joint located at the distal region. A medical practitioner may then insert a screw 2536 following a guide wire to a proximal iliac bone and distal iliac bone. A medical practitioner may use a driver that engages with a drive 2528 of a screw 2536, until the threads 2532 of such screw engages with threads 2532 of a component 2521, and/or as the external thread 2537 of such screw 2536 is driven through cortical bone of an ilium. Using a driver that engages with a drive 2528 on one screw 2522, screws located at both a distal region and proximal region may be axially rotated. As the screws are turned, a compressive force is acted between the proximally located ilium and distally located ilium, further compressing both SI joints between a bilateral device. A locking pin 2534 may further be inserted to lock a screw to a component 2521. In another example of securing a bilateral device, prior to inserting a component 2521 through an opening through a transsacral space, one end of such component 2521 may be pre-installed with a screw 2522.

Example 5

Figures 30A, 30B, 30C:
FIG. 30A. A perspective view of a bilateral device in certain embodiments.
FIG. 30B. A perspective view of a component in certain embodiments.
FIG. 30C. A side view of a bilateral device end in certain embodiments, showing a surface anchor, a screw and a locking pin embodiments.
Figure 31A:
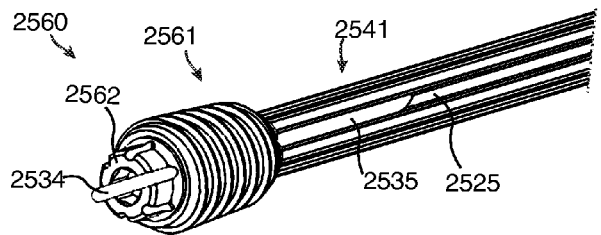
FIG. 31A. A perspective view of a bilateral device end in certain embodiments.
Figure 31B:
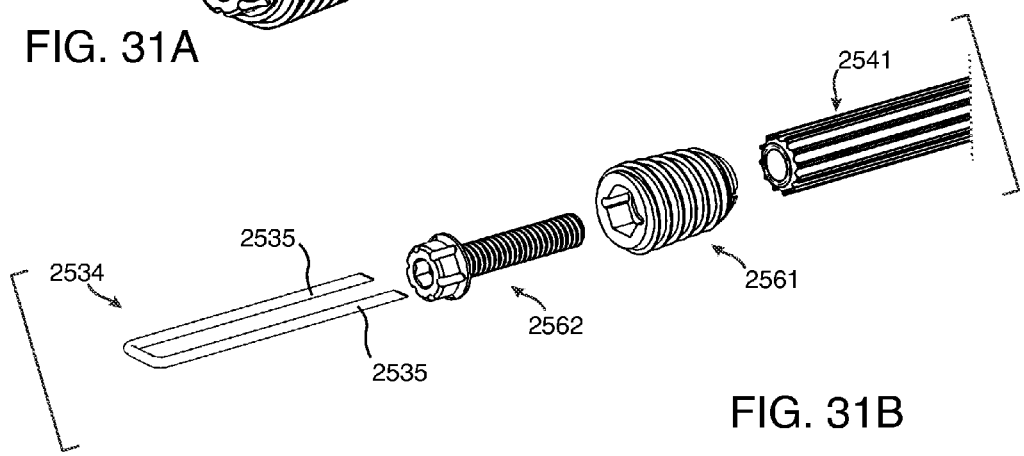
FIG. 31B. An exploded, perspective view of a bilateral device end in certain embodiments, further showing a locking pin, an end screw, a component, and a floating screw embodiment.
Figure 31C:
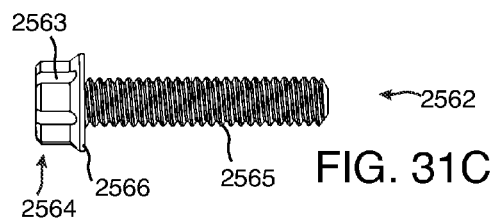
FIG. 31C. A side view of a screw in certain embodiments.
Figure 31E:
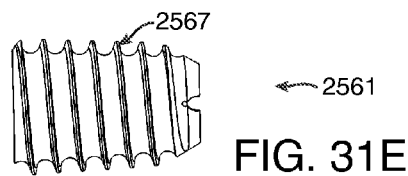
FIG. 31E. A side view of a floating screw in certain embodiments.
Figure 31D:
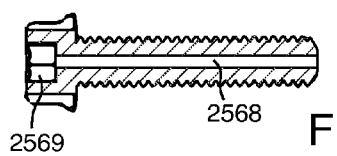
FIG. 31D. A side cross-sectional view of a screw in certain embodiments.
Figure 31F:
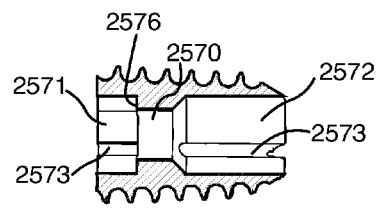
FIG. 31F. A side cross-sectional view of a floating screw in certain embodiments.
Figure 31G:
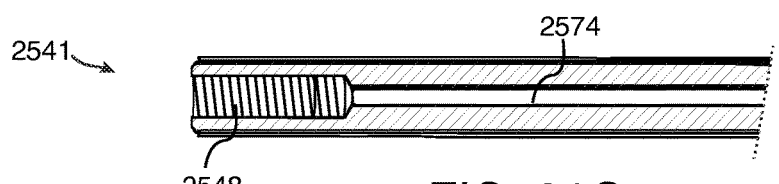
FIG. 31G. A side cross-sectional view of a component end, in certain embodiments FIG. 31H. A side cross-sectional, exploded view of a bilateral device end further showing a locking pin, an end screw, a component, and a floating screw embodiment.

In certain embodiments, a bilateral device has ends that fit with a surface, or surface features of a left ilium and right ilium. For instance, as shown in an embodiment, a bilateral device 2540 comprises a component 2541, and a surface anchor 2542, as shown for example in FIG. 30A. Referring to an example FIG. 30B, in certain embodiments, a component 2541 has a female thread 2548 on one or both ends. Referring to FIG. 31G, a component 2541 also has an axial opening 2574 running across its length as to allow one to slide the component 2541 over a guide wire, in certain embodiments. Referring to FIG. 30B, a component 2541 has a plurality of splines 2524 running longitudinally, and arranged circumferentially around its shaft.

Figures 30D, 30E, 30F:
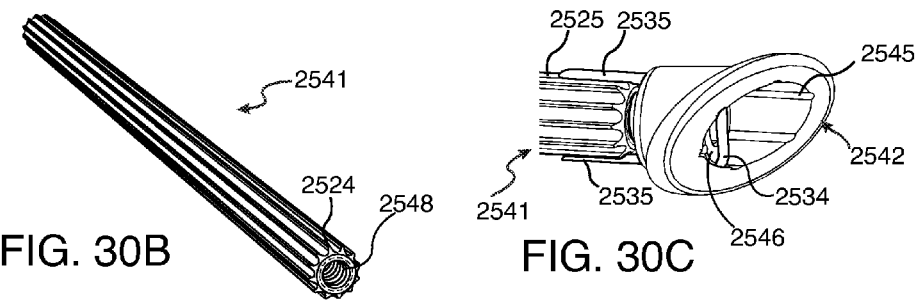
FIG. 30D. A side view of a surface anchor in certain embodiments.
FIG. 30E. A side view of a surface anchor in certain embodiments.
FIG. 30F. A perspective view of a surface anchor in certain embodiments.
Figure 30G:
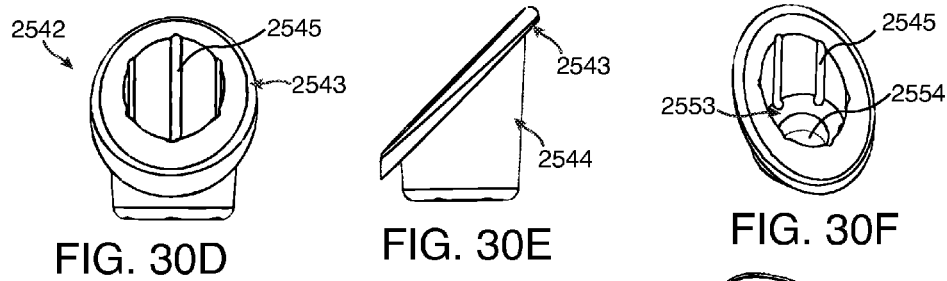
FIG. 30G. A perspective view of a surface anchor in certain embodiments.

Referring to an example in FIG. 30D and FIG. 30E, a surface anchor 2542, in certain embodiments, comprises a flange 2543 and a body 2544. It will be appreciated that the angle at which a flange 2543 is arranged relative to a body may vary according to the anatomy of certain patients. In general, a flange 2543 may be oriented at an angle perpendicular (0°) to a longitudinal axis of a bilateral device, or oriented at an angle, as shown in example figures FIG. 30A, FIG. 30C, FIG. 30D, FIG. 30E, FIG. 30F, and FIG. 30G. In certain embodiments, the angle may be between 0°, 5°, 10°, 15°, 20°, 25°, 30°, 35°, 40°, 45°, and 50°, or more. Referring to exemplary figures FIG. 30F and FIG. 30G, certain embodiments of a surface anchor 2542 have an opening 2554 that can fit a thread portion 2550 of a screw 2546 (further shown for example in FIG. 30H). Still referring to FIG. 30F and FIG. 30G, certain embodiments of a surface anchor 2542 have an annular surface 2553 that can press against a head 2552 of a screw 2546 (further shown for example in FIG. 30I). Referring to exemplary figures FIG. 30D, FIG. 30F and FIG. 30G, an embodiment of an anchor 2542 has one or more through holes 2545. As shown in FIG. 30D and FIG. 30F, a through hole 2545 may form a grooved feature on an internal portion of a body of a screw 2542. A through hole can accommodate, for example, and end 2535 of a locking pin 2534.

Figures 30H, 30I, 30J:
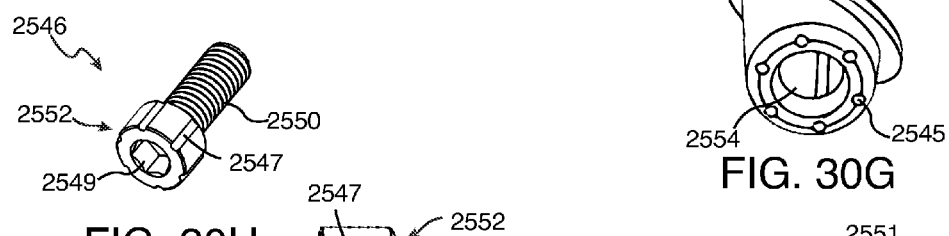
FIG. 30H. A perspective view of a screw in certain embodiments.
FIG. 30I. A side view of a screw in certain embodiments.
FIG. 30J. A side cross-sectional view of a screw in certain embodiments.

In certain embodiments, an end screw is used to further tighten a surface anchor to a component, and introducing compression. In certain embodiments, an end screw 2546 comprises a head 2552 and a thread 2550, as shown in FIG. 30H. Still referring to FIG. 30H, and further referring to FIG. 30J, embodiments of a head 2552 have a drive 2549 that fits a driver so that a medical practitioner can axially rotate an end screw using a driver. Certain embodiments of an end screw 2546, as shown in FIG. 30J, have an axial opening 2551 so that an end screw can be slid over a guide wire. Referring to FIG. 30H and FIG. 30I, a head 2552 may also have grooves 2547, where a portion of a locking pin can slidably pass such groove. For example, as shown in FIG. 30C, an end 2535 of a locking pin 2534 can be slid through a through hole 2545 of an anchor 2542, and further slid past a groove of a screw 2546, and be placed within a groove 2525 of a component 2541.

In an example of securing a bilateral device, a medical practitioner uses a drill bit having a diameter that accommodates a shaft (for example, a diameter that is smaller than the diameter comprising a spline). A guide wire established after step 270, as shown in FIG. 2B, may be used to guide a drill bit. A medical practitioner drills through a first ilium (proximal region), through a sacrum, and through a second ilium (distal region). Following such steps, a drill bit having a diameter that accommodates a body 2544 of an anchor 2542 may be used to drill preferably one, or both cortical bone layers of a distally located ilium, as well as to drill preferably one, or both cortical bone layers of a proximally located ilium. Then, a component 2541 may be inserted through the opening created through a transsacral space following a guide wire. A medical practitioner may then insert an anchor 2542 following a guide wire to a proximal region and distal region of a pelvis, until the body 2544 of such anchor is placed within a drilled hole of an ilium. In certain embodiments, a blunt tool may be used to push such anchor into place. In certain embodiments, a medical practitioner may select an anchor where the angle of its flange 2543 matches, or is roughly similar to the angle of the external surface of the ilium.

Next, using a driver that engages with a drive 2549 on an end screw 2546, screws located at both a distal region and proximal region may be axially rotated, as to further secure an anchor 2542 to a component 2541. As the screw is turned, a thread 2550 of a screw engages with an internal female thread 2548 of a component 2541. A compressive force between the proximally located ilium and distally located ilium, that further compresses both SI joints, is introduced with such embodiment of a bilateral device. A flange 2543 presses against an external surface of an ilium, and two ilia are compressed with the action of the end screws 2546. A locking pin 2534 may further be inserted to lock a screw to a component 2541, as shown in FIG. 30C. In another example of securing a bilateral device, prior to inserting a component 2541 through an opening through a transsacral space, one end of such component 2541 may be pre-installed with an anchor 2542 and a screw 2546.

Example 6

Figure 31H:
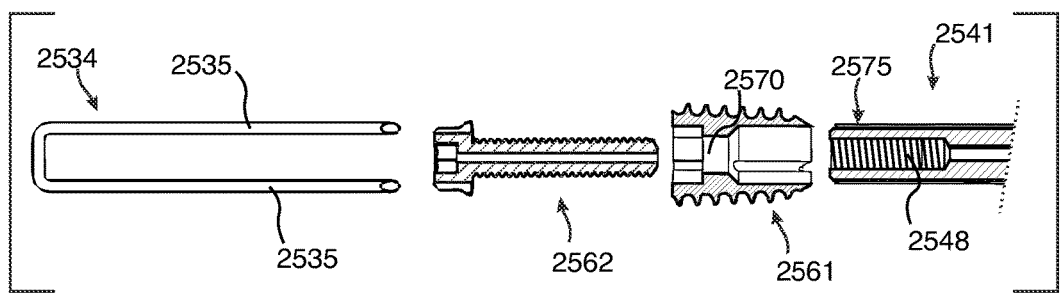
FIG. 31I. A side cross-sectional view of a bilateral device end.

In certain embodiments, a bilateral device has ends that screw into a left ilium and right ilium, and further have a locking feature. In certain embodiments, as shown for example in FIG. 31A, one end of such bilateral device 2560 comprises a floating screw 2561, an end screw 2562, a locking pin 2534, further attached to a component 2541. A screw 2561, as shown in FIG. 31E and FIG. 31F, has an external thread 2567 that engages with bone, for example, cortical or cancellous bone of an ilium. Certain embodiments of a screw 2561 also have a drive 2571, where a medical practitioner can use a driver to apply axial rotation to the screw. Certain embodiments of a screw 2561 have a recess 2572, where such recess can fit certain features of a component, for example, an end 2575 of a component 2541, as shown in FIG. 31H. Certain embodiments of a screw 2561 have smaller diameter opening 2570, where it can be appreciated that while the opening 2570 in certain embodiments may have a smooth surface, other embodiments may have female threading. In general, as shown in a cross-sectional view of a screw 2561 in FIG. 31F, an axially located opening allows one to slide a screw over a guide wire. Additionally, certain embodiments of a screw 2561 have a through hole 2573 that allows a locking pin to pass through.

Figure 31I:
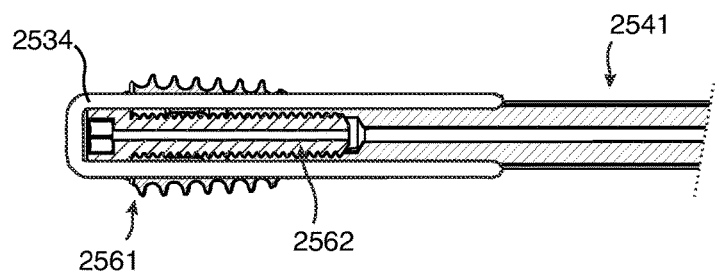

In certain embodiments, an end screw 2562 comprises a head 2564 and a thread 2565. Certain embodiments of an end screw 2562, as shown in FIG. 31D, have an axial opening 2568 so that an end screw 2562 can be slid over a guide wire. Certain embodiments of a screw 2562 also have a drive 2569, where a medical practitioner can use a driver to apply axial rotation to the screw. Referring to FIG. 31C, a head 2552 may also have one or more through holes 2563, where a portion of a locking pin can slidably pass such through hole. For example, as shown in FIG. 31A and FIG. 31I, an end 2535 of a locking pin 2534 can be slid past a through hole of an end screw 2546, and be placed within a groove 2525 of a component 2541.

It can be appreciated that an annular surface 2576 of a floating screw 2561, as shown for example in FIG. 31F, interfaces a head 2564, particularly a flange 2566 portion, of an end screw 2562 as shown in FIG. 31C. As further shown, for example, in FIG. 31C, FIG. 31H and FIG. 31I, when the thread 2565 of an end screw 2562 fits through an opening 2570 of a floating screw 2561, and the end screw 2562 further engages with an internal thread 2548 of a component 2541, the floating screw 2561 is prevented from certain movements due to such interface.

In an example of securing a bilateral device, a medical practitioner uses a drill bit having a diameter that accommodates a shaft (for example, a diameter that is smaller than the diameter comprising a spline). A guide wire established after step 270, as shown in FIG. 2B, may be used to guide a drill bit. A medical practitioner drills through a first ilium (proximal region), through a sacrum, and through a second ilium (distal region). Following such steps, a drill bit having a diameter that accommodates a floating screw 2561 may be used to drill preferably one, or both cortical bone layers of a distally located ilium, as well as to drill preferably one, or both cortical bone layers of a proximally located ilium. Then, a component 2541 may be inserted through the opening created through a transsacral space following a guide wire.

Next, further following a guide wire, two floating screws 2561 may be inserted to the left ilium and right ilium each. Using a driver, a medical practitioner may drive a screw 2561 through the cortical bone and cancellous bone of an ilium, performing such step for both the left ilium and right ilium. Next, further following a guide wire, two end screws 2562 may be inserted to the left ilium and right ilium each. Using a driver, a medical practitioner may screw an end screw 2562 so that its thread 2565 engages with the internal female thread 2548 of a component 2541 as shown in FIG. 31G and FIG. 31H. An end screw 2562 may be then be placed on the opposite side of the pelvis. Because the floating screws 2561 are located in the ilium, tightening of one or both the end screws 2562 can effectively create a compressive force between the two ilia and thus the two SI joints. Finally, a locking pin 2534, as further shown in FIG. 31A, FIG. 31B, FIG. 31H, and FIG. 31I may be used to further secure an assembly, thus, for example, preventing further movement of an end screw 2562 and a floating screw 2561.

Advantages of Embodiments of the Methods and Related Devices

Unlike several prior art procedures and methods, which fail to accomplish the deep placement of bone substances in the SI joint with allograft, autograft, or other bone fusion materials, the certain embodiments of the invention facilitates the deep placement of bone substances within the SI joint. Certain embodiments provide access to the SI joint space through the oblique paths, which enable the SI joint to be accessed and the articular surfaces to be further decorticated by the medical practitioner via a variety of decortication tools and mechanisms. Effective decortication is an important aspect of the preferred embodiment of the invention, as decortication prepares a large bone surface area within the SI joint space to allow bone fusion. The large surface area facilitates the increased stability of the SI joint area once the bone is fused and healed, further minimizing the risks of destabilization of the SI joint and the stabilizer devices within such SI joint after healing. Thus, the risks of pseudoarthrosis and other complications are decreased. A number of benefits derive from the combination of the filling of the SI joint space with graft material, and the compression of the SI joint with screws, as described herein. The compression of an ilium and sacrum using the stabilizer devices facilitates bone fusion, while the bone fusion stabilizes and prevents the movement of such stabilizer devices. The combined approach described herein, therefore, maximizes bone fusion, reduces risk of breakage of instrumentation, and reduces the risk of pseudoarthrosis and other related complications.

General procedures to close the incision previously created during the aforementioned steps are performed, in the preferred embodiment of the invention. Incisions may be closed, for example, using sutures, bandages, staples, and other ways known to those skilled in the art. In certain embodiments, general blood loss may be less compared to other standard procedures due to a relatively smaller incision.

The present inventor recognizes that approximately 20% of patients require a fusion on both sacroiliac joints. An alternative embodiment of the invention features apparatuses and techniques specifically intended to accomplish a bilateral sacral iliac fusion. In such embodiment incorporating methods, procedures and apparatuses related to bilateral sacral iliac fusion, the same guide wire traverses first the proximal ilium, the entirety of the sacrum, and then into and through the distal ilium.

In such embodiment related to bilateral SI fusion, the guide wire may feature a sharp tip at the end of the guide wire to enable the medical practitioner to forego the use of a trephine needle to tunnel through the proximal ilium, sacrum, distal ilium and other tissues and biological structures encountered during the related methods and procedures. To accomplish the traversal of the proximal ilium, the sacrum, the distal ilium, and related tissues, the medical practitioner may attach the guide wire to a drill, to enable the end of the guide wire to function specifically as a drill tip. Alternatively, the medical practitioner may tap or apply pressure to the guide wire to force the guide wire through the proximal ilium, sacrum, distal ilium and other tissues and biological structures encountered during the related methods and procedures.

Upon reaching and traversing the distal ilium, the medical practitioner then accesses the guide wire through an aperture in the skin located near the distal ilium. Such access may take place via an incision and other related steps, such as those disclosed herein. In certain embodiments, the medical practitioner then places a first screw over the guide wire located near the distal ilium. A first screw is placed into and through the distal ilium and into the sacrum to fuse the distal ilium to the sacrum. The placement of a first screw takes place through an aperture in the skin near the distal ilium. The medical practitioner also places a second screw over the guide wire located near the proximal ilium. The medical practitioner places a second screw into and through the proximal ilium and into the sacrum to fuse the proximal ilium to the sacrum. The placement of the second screw takes place through an aperture in the skin near the proximal ilium. In related embodiments of the invention, the placement of the first and second screws need not be placed sequentially, such that the placement of the second screw into and through the proximal ilium into the sacrum can occur prior to the placement of the first screw into and through the distal ilium into the sacrum. As a result of the placement of the screws over the same guide wire, and the tightening of such screws, the guide wire aids in the compression of both sacral iliac joints by pulling both the proximal ilium and distal ilium in to the sacrum, thus compressing both SI joints thereby benefiting the quality of the fusion of both sacral iliac joints, particularly when used in conjunction with the placement of graft material or implant into the space between the sacrum and each ilium. The inventor has recognized benefits associated with the bilateral SI fusion methods, procedures and apparatuses described herein, which include reductions in the time required to accomplish the fusion of both SI joints of a single patient during a single surgery session, and the avoidance of a variety of nerves, blood vessels, soft tissue and other sensitive anatomical features.

In general, various aspects of certain embodiments of the invention are performed by a medical practitioner, such medical practitioner may be a number of entities related to a surgical procedure, including but not limited to surgeons, physician's assistants, nurses, technicians, neurodiagnostic technicians, and anesthesiologists. In general, in the preferred embodiment of the invention, a patient refers to an entity receiving the sacroiliac fusion approach disclosed herein. In certain embodiments of the invention, the sacroiliac fusion approach is performed in conjunction with a number of instruments, including, but not limited to bone-imaging or bone scanning devices such as, for example, biplanar fluoroscopes (also commonly referred to as C-Arm Fluoroscopes), and electrotransmitters and related accessories. In the preferred embodiment of the invention, such bone-imaging or bone scanning devices captures images of the patient through various views, including but not limited to the lateral view, oblique view, anterior-posterior (AP) view, inlet view, and outlet view of such patient.

Embodiments of a stabilizer device, bilateral device, and other devices disclosed here are fabricated from a number of biocompatible materials appropriate for securement of a sacrum and one or more ilium. Such biocompatible materials may be metals, ceramics, synthetic polymers, bone graft, and bone, but is not limited to these materials. Certain embodiments of the stabilizer device, bilateral device, and other devices disclosed preferably be a metal such as pure titanium, grade 5 titanium, titanium alloys including but not limited to, for example, a titanium aluminum vanadium alloy (Ti6Al4V), stainless steel alloys, and nitinol, but is not limited to such metals or metal composites. In certain embodiments of the invention, the stabilizer device is a polymer such as, for example polyetheretherketone (PEEK), polyaryletherketone (PEAK), and polyetherketone (PEK), but is not limited to such polymers. In certain embodiments, such devices may be further coated or have an outer surface comprising a certain material or materials, for example, a rough micro texture Ti6AlV. Although compositions for certain embodiments of the stabilizer device, bilateral device, and other devices disclosed are disclosed, it will be appreciated that certain embodiments of the invention are made of on or materials that include but are not limited to those organic, polymeric, man-made.

The illustrations of arrangements described herein are intended to provide a general understanding of the structure of various embodiments, and they are not intended to serve as a complete description of all the elements and features of apparatus and systems that might make use of the structures described herein. Many other arrangements will be apparent to those of skill in the art upon reviewing the above description. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

The preceding description has been presented with reference to various embodiments. Persons skilled in the art and technology to which this application pertains will appreciate that alterations and changes in the described structures and methods of operation can be practiced without meaningfully departing from the principle, spirit and scope.

The present systems, methods, means, and enablement are not limited to the particular systems, and methodologies described, as there can be multiple possible embodiments, which are not expressly illustrated in the present disclosures. It is also to be understood that the terminology used in the description is for the purpose of describing the particular versions or embodiments only, and is not intended to limit the scope of the present application.

Some embodiments, illustrating its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any methods, and systems similar or equivalent to those

What is claimed is:

1. A surgical method, comprising:
identifying a first approach path through interfacing surfaces of adjacent bone structures;
creating a first incision intersecting said first approach path;
inserting a first needle through said first incision to a first bone structure;
confirming, through imaging, said first needle follows said identified first approach path;
inserting a first guide wire through said first needle; removing said needle;
identifying a second approach path intersecting with a joint space between said interfacing surfaces of said adjacent bone structures;
creating a second incision intersecting said second approach path;
inserting a second needle though said second incision between said first bone structure and said second bone structure;
expanding said second path;
inserting an access portal following said second path;
decorticating surfaces between the first bone structure and the second bone structure through said access portal;
packing graft material between the first bone structure and the second bone structure through said access portal;
a first drilling step, following said first guide wire to create a pathway through said first bone structure through said interfacing surfaces and into said second bone structure;
a second drilling step following said first guide wire to expand said pathway through said first bone structure; and
inserting a stabilizer device through said pathway,
wherein said drilling steps result in said pathway having a first diameter in said first bone structure and a second diameter in said second bone structure with said first diameter larger than said second diameter.

2. The surgical method of claim 1 wherein:
said adjacent bone structures comprise an ilium and a sacrum and said joint-space comprise a sacroiliac joint;
said first approach path comprises a lateral approach to said sacroiliac joint; and
said second approach path comprises an oblique approach to said sacroiliac joint.

3. The surgical method of claim 2 wherein said step of inserting a first needle further comprises said first needle traversing through said ilium, across said sacroiliac joint and into said sacrum.

4. The surgical method of claim 2 wherein said step of inserting stabilizer device further comprises said stabilizer device traversing two cortical layers of said ilium and one cortical layer of said sacrum.

5. The surgical method of claim 2 wherein said step of inserting stabilizer device further comprises said stabilizer device being threadably engaged with at least one cortical layer of said ilium.

6. The surgical method of claim 5 wherein said step of inserting stabilizer device further comprises said stabilizer device being threadably engaged with said sacrum.

7. The surgical method of claim 1 wherein said graft material comprises bone material harvested from said patient.

8. The surgical method of claim 1 wherein said steps beginning with identifying a second approach angle and ending with the step of packing bone graft material are repeated.

9. The surgical method of claim 1 wherein said stabilizer device incorporates a self-harvesting feature.

10. The surgical method of claim 1, wherein said first approach path is substantially orthogonal to the interfacing surfaces of said adjacent bone structures.

11. The surgical method of claim 1, wherein said second approach path is substantially planar with said joint space.

12. The surgical method of claim 1, wherein said needle consists of a trephine needle.

13. The surgical method of claim 1, wherein said stabilizer device is configured to provide a compressive force therebetween said first bone structure and said second bone structure.

14. The surgical method of claim 1, further comprising a third drilling step following expanding a proximal portion of said pathway.

* * * * *